United States Patent
Orlowski et al.

(10) Patent No.: US 11,071,767 B2
(45) Date of Patent: Jul. 27, 2021

(54) DIETARY COMPOSITIONS FOR REDUCING BLOOD GLUCOSE LEVELS AND FOR WEIGHT MANAGEMENT

(71) Applicant: MARMAR INVESTMENT SP. Z O.O., Warsaw (PL)

(72) Inventors: Marek Orlowski, Warsaw (PL); Marcin Krotkiewski, Benitachell (ES); Katarzyna Billing-Marczak, Chyliczki (PL)

(73) Assignee: MARMAR INVESTMENT SP. Z O.O., Warsaw (PL)

( * ) Notice: Subject to any disclaimer, the term of this patent is extended or adjusted under 35 U.S.C. 154(b) by 524 days.

(21) Appl. No.: 15/303,021

(22) PCT Filed: Apr. 12, 2015

(86) PCT No.: PCT/IB2015/052650
§ 371 (c)(1),
(2) Date: Oct. 10, 2016

(87) PCT Pub. No.: WO2015/159195
PCT Pub. Date: Oct. 22, 2015

(65) Prior Publication Data
US 2017/0028011 A1 Feb. 2, 2017

Related U.S. Application Data

(60) Provisional application No. 61/978,900, filed on Apr. 13, 2014.

(51) Int. Cl.
*A23L 2/52* (2006.01)
*A23L 33/00* (2016.01)
*A23L 33/105* (2016.01)
*A23L 33/21* (2016.01)
*A61K 31/7004* (2006.01)
*A61K 31/733* (2006.01)
*A61K 31/736* (2006.01)
*A61K 36/48* (2006.01)
*A61K 36/605* (2006.01)
*A61K 36/74* (2006.01)
*A61K 47/46* (2006.01)
*A61K 9/00* (2006.01)
*A61K 9/08* (2006.01)
*A23L 23/00* (2016.01)
*A23L 7/109* (2016.01)

(52) U.S. Cl.
CPC ............... *A61K 36/74* (2013.01); *A23L 2/52* (2013.01); *A23L 7/109* (2016.08); *A23L 23/00* (2016.08); *A23L 33/105* (2016.08); *A23L 33/21* (2016.08); *A23L 33/30* (2016.08); *A61K 9/0053* (2013.01); *A61K 9/08* (2013.01); *A61K 31/7004* (2013.01); *A61K 31/733* (2013.01); *A61K 31/736* (2013.01); *A61K 36/48* (2013.01); *A61K 36/605* (2013.01); *A61K 47/46* (2013.01); *A23V 2002/00* (2013.01)

(58) Field of Classification Search
CPC ............ A61K 2300/00; A61K 31/7004; A61K 31/733; A61K 31/736; A61K 36/48; A61K 36/605; A61K 36/74; A61K 47/46; A61K 9/0053; A61K 9/08; A23L 23/00; A23L 2/52; A23L 33/105; A23L 33/21; A23L 33/30; A23L 7/109; A23V 2002/00
See application file for complete search history.

(56) References Cited

U.S. PATENT DOCUMENTS

| 7,125,573 | B2 | 10/2006 | Okawa |
| 2007/0009615 | A1 | 1/2007 | Zhong |
| 2007/0166320 | A1 | 7/2007 | Yamazaki |
| 2008/0254153 | A1 | 10/2008 | Wang |
| 2011/0052754 | A1 | 3/2011 | Foley |
| 2013/0177506 | A1 | 7/2013 | Atkins |

FOREIGN PATENT DOCUMENTS

| CN | 102524769 A | 7/2012 |
| CN | 103961395 | 8/2014 |
| EP | 1 923 067 | 5/2008 |
| JP | H11335285 A | 12/1999 |
| JP | 2000219632 A | 8/2000 |
| JP | 2002136272 A | 5/2002 |

(Continued)

OTHER PUBLICATIONS

Schultz, Hank "Tests Turn Up Adulterated Green Coffee Bean Extracts" NUTRA, retreived online Dec. 22, 2018 from <URL:https://www.nutraingredients-usa.com/Article/2012/12/07/Tests-turn-up-adulterated-green-coffee-bean-extracts#>,published Dec. 7, 2012, 2 pages. (Year: 2012).*
Bray & Wadden, (2015) Improving long-term weight loss maintenance: Can we do it?. Obesity, 23(1), 2-3.
Celleno et al ., (2007) A dietary supplement containing standardized Phaseolus vulgaris extract influences body composition of overweight men and women. Int J Med Sci, 4(1), 45-52—A category.
Daum et al., (2010) Arrangement of photosystem II and ATP synthase in chloroplast membranes of spinach and pea. The Plant Cell, 22(4), 1299-1312.

(Continued)

*Primary Examiner* — Aaron J Kosar
(74) *Attorney, Agent, or Firm* — Wenderoth, Lind & Ponack, L.L.P.

(57) ABSTRACT

The present invention provides dietary compositions comprising mulberry extract, coffee extract, bean extract, optionally, dietary fibers, and a nutraceutically acceptable carrier. The present invention further provides methods for preventing the increase in postprandial hyperglycemia and hypoglycemia, hyperinsulinemia and diseases and disorders associated therewith, including, endothelial dysfunction, inflammatory conditions, oxidative stress, hyperlipidemia, and consecutive pathologies like insulin resistance, diabetes, visceral obesity, hypertension and cardiovascular diseases.

18 Claims, 29 Drawing Sheets

(56) References Cited

FOREIGN PATENT DOCUMENTS

| | | |
|---|---|---|
| JP | 2004528050 A | 9/2004 |
| KR | 1020130078144 A | 7/2013 |
| WO | 2006132586 | 12/2006 |
| WO | 2008/115723 | 9/2008 |
| WO | 2010008333 | 1/2010 |
| WO | 2012113918 | 8/2012 |
| WO | 2013/078658 | 6/2013 |

OTHER PUBLICATIONS

Jeszka-Skowron et al., (2014) Mulberry leaf extract intake reduces hyperglycaemia in streptozotocin (STZ)-induced diabetic rats fed high-fat diet. Journal of Functional Foods, 8, 9-17—A category.

International Search Report for PCT/IB2015/052650 Completed Aug. 13, 2015; dated Aug. 25, 2015 4 pages.

Written Opinion for PCT/IB2015/052650 Completed Aug. 13, 2015; dated Aug. 25, 2015 7 pages.

Anno et al., (2004) Maltase, Sucrase and α-Amylase Inhibitory Activity of Morus Leaves Extract. Japan Food Preservation Science Association Journal 30(5): 223-229. Abstract.

Izumi and Takaya (2008) Influence of various of extraction conditions and amount of chlorogenic acid on the taste of coffee. Japan Cooking Association Journal 41(4): 257-261. Abstract.

Nakamura (2006) At present state of food for specified health uses in Japan. Advanced in Medicine 218(5): 351-354. Abstract.

Cai et al., (2014) Simultaneous determination of chlorogenic acid and caffeine in green coffee bean extract by ultra-performance Liquid Chromatography—ultraviolet Detection. China Food Additives 2: 225-228. Abstract.

Chen et al., (2012) The anti-obesity effect on rats of α-amylase inhibitor from kidney bean (*Phaseolus vulgaris*). Food Science and Technology 37(10): 207-210. Abstract.

Zhi Zhang et al., (2013) Effect of Compound Preparation of White Kidney Bean on Blood Glucose in Hyperglycemic Model Mice. Practical Clinical journal of Integrated Traditional Chinese and Western Medicine 13(4): 83-85. English translation of abstract.

* cited by examiner

DIETARY COMPOSITIONS FOR REDUCING BLOOD GLUCOSE LEVELS AND FOR WEIGHT MANAGEMENT

FIELD OF THE INVENTION

The present invention provides dietary compositions comprising mulberry extract, coffee extract, bean extract, optionally, dietary fibers, and a nutraceutically acceptable carrier. The present invention further provides methods for preventing the increase in postprandial hyperglycemia and hypoglycemia, hyperinsulinemia and diseases and disorders associated therewith, including, endothelial dysfunction, inflammatory conditions, oxidative stress, hyperlipidemia, and consecutive pathologies like insulin resistance, diabetes, visceral obesity, hypertension and cardiovascular diseases.

BACKGROUND OF THE INVENTION

The high incidence of metabolic disorders in humans and their related impact on health and mortality represents a significant threat to public health. These include obesity and type II diabetes, among others. However, pharmaceuticals currently used as a measure against disorders associated with abnormal glucose blood level, such as, diabetes, obesity, hypercholesterolemia, hyperglycemia, postprandial hyperglycemia and hyperlipidemia are a serious burden for patients since the alleged satisfactory effectiveness is accompanied with many side effects and the long term effects are not sufficiently convincing (Bray et al., Obesity, 23(1):2-3, 2015).

Hyperglycemia and postprandial hyperglycemia are related to increased generation of inflammation factors and free radicals responsible for the mitochondrial malfunction and oxidative stress of the endothelial reticulum leading to insulin resistance which is the main cause of diabetes, and metabolic syndrome associated with visceral obesity. However, pharmaceuticals used for treating or preventing the aforementioned disorders exhibit side effects and tend to induce development of tolerance in long term use, resulting in a disability to prevent the ongoing deterioration of glucose homeostasis.

Along with a tendency of the last few decades to recognize the importance of complementary therapies, nutraceutical compositions received great attention as advantageous therapy in certain disorders. U.S. Pat. No. 7,125,573 discloses a composition comprising raw coffee bean extract, and, optionally, one or more other additive, including mulberry leaves, and use thereof for reducing hypertension.

US 2011/0052754 discloses a composition comprising one or more of the following components: (1) a component for supporting healthy thyroid function; (2) a component for increasing satiety; (3) a component for inhibiting carbohydrate uptake and usage, such as, green coffee bean extract, white kidney bean extract and mulberry powder extract; (4) a component for increasing caloric expenditure; and (5) a component for increasing fatty acid oxidation therefore improving lean body composition.

US 2008/0254153 discloses a composition of water extractible, lipophilic and non-lipophilic bioactive components that are exclusively of fruit or vegetable or plant origin wherein the profile of the bioactive components is similar or identical to that of the corresponding whole fruit or vegetable, and wherein the fruit, vegetable or plant material comprises mulberry and/or coffee. The composition is used for treating cardiovascular diseases, cancers or diabetes.

US 2007/0166320 discloses a functional food comprising an agent for preventing/ameliorating diabetes mellitus and for suppressing an increase in blood glucose level, the agent comprises dried tea tree mushroom and at least one more component, such us, mulberry leaves and the functional food may be in the form of coffee.

There remains an unmet need for a composition of dietary supplements that exhibit significant therapeutic effect in diseases and disorder associate with abnormal blood glucose levels.

SUMMARY OF THE INVENTION

The present invention provides dietary compositions and use thereof for maintaining balanced glucose and insulin levels, for reducing blood glucose levels in the treatment of diseases associated therewith, including, postprandial hyperglycemia, for reducing glycemic index of foods and for improving glucose homeostasis.

In some embodiments, the composition may ameliorate dyslipidemia, improve atherosclerotic index and ameliorate fatty liver. Accordingly, the methods of the present invention may prevent development of, or attenuate, pathological conditions, such as, diabetes, visceral obesity, endothelial dysfunction, low grade inflammation, oxidative stress and metabolic syndromes. The dietary compositions of the invention encompass a plurality of nutraceutical supplements, including white mulberry extract, green coffee extract, white bean extract and, optionally, fibers.

The present invention is based in part on the unexpected beneficial effect obtained by combining nutraceutical supplements which do not exert the desired effect when used alone. Specifically, the inventors of the present invention have found that each of mulberry extract, green coffee extract and white bean extract reduced glycemia in rats fed on glucose, sucrose or starch in a random, inconsistent, manner (e.g. Example 1). However, administering a combination of all three supplements resulted with a significant reduction in blood glucose in rats fed on sucrose, starch or a high fat diet, and in obese rats (e.g. Examples 2 and 3) and in healthy subjects (e.g. Example 7). Furthermore, it was surprisingly found that the specific combination of mulberry extract, green coffee extract and white bean extract is advantageous over combinations including only two plant extracts and over other combinations of three plant extracts (e.g. Example 5). Surprisingly, the dietary combinations of the invention also induced a significant reduction in fat mass, a significant increase in lean mass and a significant reduction in fat-muscle mass ratio. In addition, the nutraceutical composition of the invention exerted an unexpected reduction in hypoglycemic episodes in healthy subjects following consumption of food products with high glycemic index.

In some embodiments, there is provided a dietary composition comprising mulberry extract, coffee extract, bean extract as the nutraceutically active component and a nutraceutically acceptable carrier.

In some embodiments, the nutraceutically active component is consisting of coffee extract, bean extract and mulberry extract.

In some embodiments, the coffee extract is an extract of green coffee beans. In some embodiments, the mulberry extract is an extract of white mulberry leaves.

In some embodiments, the composition further comprises dietary fiber. In some embodiments, the dietary fiber is selected from the group consisting of glucomannan, insulin, psyllium, oat gum (beta glucan), guar gum, pectin, soybean fiber, oat bran, xanthan, cyclodextran, oligofructose, chitinin, derivatives and combinations thereof. Each possibility represents a separate embodiment of the present invention.

In some embodiments, the nutraceutical acceptable carrier comprises one or more of sweeteners, flavoring agents, diluents, liposome, licosome matrix and binders. Each possibility represents a separate embodiment of the present invention.

In some embodiments, the composition further comprises one or more flavoring agents, such as, cinnamon.

In some embodiments, the composition further comprises gymnema sylvestre.

In some embodiments, the composition is in an oral dosage form. In some embodiments, the composition is a lozenge, a tablet, a capsule, a chewable dosage form, a food bar, a suspension, powder, granulate, syrup or a beverage. Each possibility represents a separate embodiment of the present invention.

In some embodiments, the composition is a powder form or granulate ready for use after being dissolved in a drink, such as, water.

In some embodiments, the composition further comprises a time release coating. In some embodiments, the time release coating comprises lecithin.

In some embodiments, the composition further comprises arabinose.

In some embodiments, there is provided a method for maintaining glucose homeostasis in a subject in need thereof, the method comprising administering to the subject a dietary composition comprising mulberry extract, coffee extract and bean extract as the nutraceutically active component.

In some embodiments, there is provided a method for maintaining insulin homeostasis in a subject in need thereof, the method comprising administering to the subject a dietary composition comprising mulberry extract, coffee extract and bean extract as the nutraceutically active component.

In some embodiments, there is provided use of a dietary composition comprising mulberry extract, coffee extract and bean extract as the nutraceutically active component for maintaining glucose homeostasis.

In some embodiments, there is provided use of a dietary composition comprising mulberry extract, coffee extract and bean extract as the nutraceutically active component for maintaining insulin homeostasis.

In some embodiments, there is provided a method for reducing blood glucose levels in a subject in need thereof, the method comprising administering to the subject a dietary composition comprising mulberry extract, coffee extract and bean extract as the nutraceutically active component.

In some embodiments, the subject is afflicted with a diseases or disorder selected from the group consisting of diabetes, obesity, hypercholesterolemia, hyperglycemia, postprandial hyperglycemia and hyperlipidemia. Each possibility represents a separate embodiment of the present invention.

In some embodiments, reducing blood glucose levels comprises treating prediabetes and diabetes, preventing prediabetes and diabetes, treating obesity, treating hypercholesterolemia, treating hyperlipidemia and treating metabolic syndrome. Each possibility represents a separate embodiment of the present invention.

In some embodiments, reducing blood glucose levels comprises treating prediabetes. In some embodiments, reducing blood glucose levels comprises treating diabetes. In some embodiments, reducing blood glucose levels comprises preventing diabetes. In some embodiments, reducing blood glucose levels comprises preventing prediabetes. In some embodiments, reducing blood glucose levels comprises treating obesity. In some embodiments, reducing blood glucose levels comprises treating hypercholesterolemia. In some embodiments, reducing blood glucose levels comprises treating hyperlipidemia. In some embodiments, reducing blood glucose levels comprises treating metabolic syndrome.

In some embodiments, the method is for preventing progression of prediabetes and diabetes. In some embodiments, the method is for treating prediabetes and diabetes.

In some embodiments, the method is for inducing satiety.

In some embodiments, the composition is administered orally.

In some embodiments, the reduction in blood glucose levels is maintained for at least one hour following administration of the dietary composition. In some embodiments, the reduction in blood glucose levels is maintained for at least two hours following administration of the dietary composition.

In some embodiments, the composition is administered prior to intake of a meal.

In some embodiments, there is provided a method for weight management in a subject in need thereof, comprising administering to the subject a diabetic composition comprising mulberry extract, coffee extract, bean extract as the nutraceutically active component and a nutraceutically acceptable carrier.

In some embodiments, the weight management comprises prevention of weight gain and induction of weight loss.

In some embodiments, the subject is afflicted with at least one disease or disorder selected from the group consisting of diabetes, obesity, hypercholesterolemia and hyperlipidemia and metabolic syndrome. Each possibility represents a separate embodiment of the present invention.

In some embodiments, the method is for preventing progression of obesity. In some embodiments, the method is for treating obesity.

In some embodiments, the composition is administered prior to intake of a meal.

In some embodiments, there is provided a method for preventing and/or treating hypoglycemia or a condition associated with hypoglycemia in a subject in need thereof, the method includes administering to the subject a dietary composition including mulberry extract, coffee extract and bean extract as the nutraceutically active components.

In some embodiments the condition is prediabetes or diabetes. In some embodiments, preventing hypoglycemia includes detaining progression of prediabetes or diabetes.

In some embodiments, said hypoglycemia is reactive hypoglycemia. In some embodiments, said method is for preventing reactive hypoglycemia.

In some embodiments, the condition is insulin resistance. In some embodiments, preventing hypoglycemia includes detaining progression of insulin resistance.

In some embodiments, the method further includes treating prediabetes or diabetes.

In some embodiments, the method further includes treating insulin resistance.

In some embodiments, preventing and/or treating hypoglycemia is maintained for at least one hour following administration of the dietary composition. In some embodiments, preventing and/or treating hypoglycemia is maintained for at least two hours following administration of the dietary composition.

In some embodiments, the subject in need thereof has blood glucose level below 70 mg/dl. In some embodiments, the subject in need thereof has blood glucose level below 65 mg/dl. In some embodiments, the subject in need thereof has blood glucose level below 60 mg/dl.

In some embodiments, the composition is administered before intake of a meal. In some embodiments, the meal includes at least one food product having a high glycemic index.

Further embodiments, features, advantages and the full scope of applicability of the present invention will become apparent from the detailed description and drawings given hereinafter. However, it should be understood that the detailed description, while indicating preferred embodiments of the invention, are given by way of illustration only, since various changes and modifications within the spirit and scope of the invention will become apparent to those skilled in the art from this detailed description.

DETAILED DESCRIPTION

Figure 1:
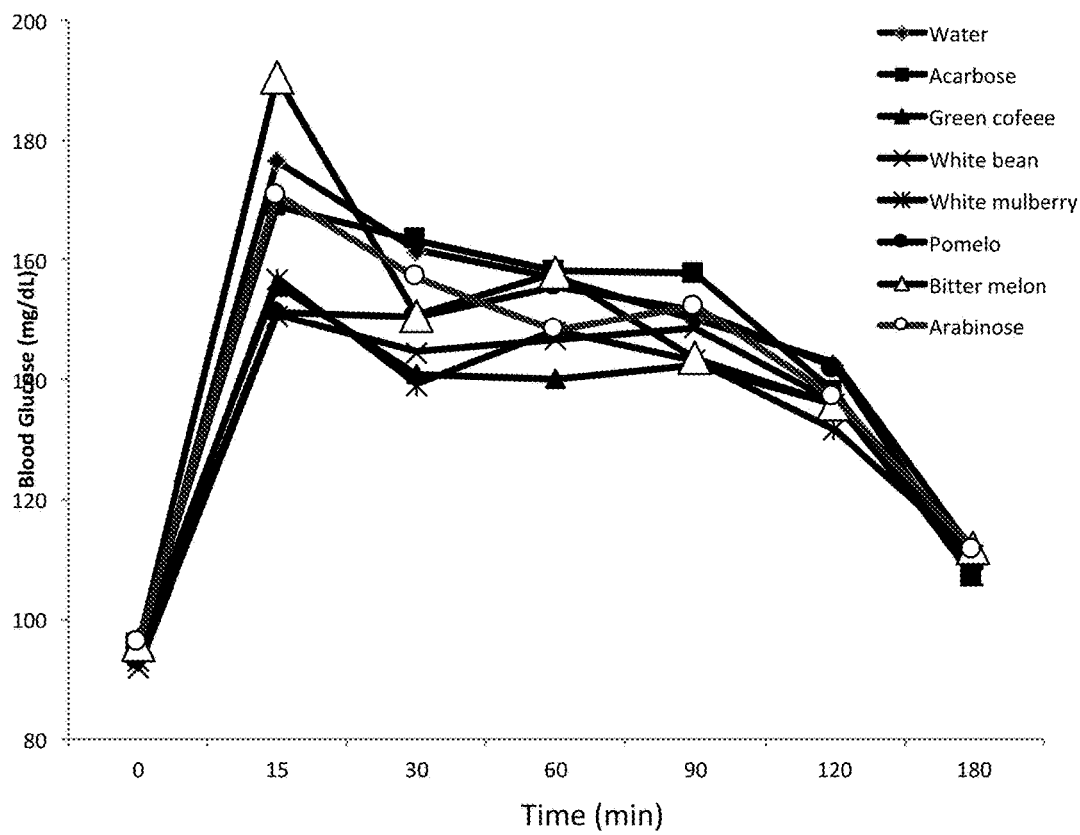
FIG. 1 represents glucose tolerance test following administration of 50% glucose solution in rats receiving a plant extract selected from pomelo (solid circle), bitter melon (empty triangle), white mulberry (asterisk), white bean (X), green coffee (solid triangle), arabinose (empty circle), acarbose (solid square) as a positive control and water (diamond) as a negative control.

The present invention provides a dietary composition comprising mulberry extract, green coffee extract, white bean extract, and a nutraceutically acceptable carrier.

In some embodiments, the dietary composition of the invention is devoid of artificially added sweeteners or sugar. In some embodiments, the dietary composition of the invention comprises artificial sugar substitutes.

The terms "sugar substitutes", "sweeteners", "artificial sweeteners", and "artificial sugar substitutes", as used herein refer to artificially added agents that add sweetness to the composition, including, but not limited to, stevia, sucralose, saccharin and the like.

The term 'mulberry extract' as used herein includes, but is not limited to, white mulberry (also known as *Morus alba*) extract and an extract derived from the leaves, fruits, stem, branches or buds of white mulberry, wherein the mulberry extract is rich in 1-deoxynojirimycin (DNJ).

The term 'coffee extract' as used herein, includes, but is not limited to, raw, optionally, green, coffee bean extract. In some embodiments, the coffee extract is a green coffee extract having a concentration of 30-70% chlorogenic acid. In some embodiments, the coffee extract is obtained from beans of *C. Arabica, C. robusta, C. liberica, C. arabusta* and combinations thereof. Each possibility represents a separate embodiment of the present invention.

In some embodiments, the raw coffee bean extract is produced by solvent extraction of coffee beans. In some embodiments, the raw coffee bean extract is produced by supercritical fluid extraction of coffee beans. In some embodiments, the raw coffee bean extract is obtained by extracting raw coffee beans with a mixture of water and ethanol.

The term 'bean extract' as used herein, refers to white kidney bean extract containing fasolamine. In some embodiments, the amount of white kidney bean extract containing fasolamine is standardized for units of activity for amylase inhibition.

The term 'dietary composition' refers to a composition of nutraceutical as the active ingredients. Nutraceuticals refers to extracts of plants, including herbals, fruits and vegetables.

As detailed herein below, the beneficial effect exerted by the dietary compositions of the present invention was assessed, inter alia, in comparison to the effect of therapeutics known to reduce blood glucose, for example, acarbose.

The term 'arabinose' as used herein, refers to arabinose and primarily L-Arabinose (the most common form of arabinose in nature), which is a natural, poorly absorbed pentose (5-carbon monosaccharide) that was previously described as selectively inhibiting intestinal sucrase activity. The significant increase in lipogenic enzyme activities and triacylglycerol concentrations in the liver as induced by dietary sucrose, has been significantly prevented by arabinose. Arabinose feeding was shown to reduce the weights of epididymal adipose tissue, plasma insulin and triacylglycerol concentrations, suggesting that L-arabinose modulates, typically via inhibition, the intestinal activity of enzymes which are capable of reducing sucrose and starch utilization and consequently attenuate lipogenesis.

Acarbose, also known as Glucobay®, Precose® and Prandase®, is a commercial anti-diabetic drug prescribed, for the treatment of type 2 diabetes mellitus and, in some countries, for the prevention of diabetes. Use of Acarbose is highly associated with side effects, primarily, diarrhea and flatulence.

Any methods for extracting and collecting bioactive ingredient from a fruit or a plant material may be applied for obtaining the claimed extracts, for example, the method disclosed in US 2008/0254153.

In some embodiments, the dietary compositions of the invention further comprise dietary fibers. In some embodiments, the dietary fibers is any one or more of the following glucomannan, insulin, psyllium, oat gum (beta glucan), guar gum, pectin, soybean fiber, polydextran, cyclodextran, oligofructose, chitinin and its derivatives and oat bran. Each possibility represents a separate embodiment of the present invention.

In some embodiments, the dietary compositions of the invention are in a controlled release dosage form. In some embodiments, the dietary compositions of the invention are in a controlled release dosage form selected from the group consisting of: delayed release dosage form, extended release dosage form, sustained release dosage form, slow release dosage form, and combinations thereof. Each possibility represents a separate embodiment of the present invention.

In some embodiments, the dietary compositions of the invention comprise time release coating.

In some embodiments, the dietary compositions of the invention further comprise one or more of lecithin and polyalkylimide polymers, liposome and licosome matrix among others. Each possibility represents a separate embodiment of the present invention.

In some embodiments, the dietary compositions of the invention are in an oral dosage form suitable for oral administration. In some embodiments, the dietary compositions of the invention are in an oral form selected from capsules, gelatin capsules, soft capsules, tablets, sugar-coated tablets, pills, pastes or pastilles, gums, powder, granulates or drinkable solutions or emulsions, such as, soups and shots, nutritional bars, syrup or a gel, with a dose of about 0.1 to 100% of the dietary supplements, i.e. the primary composition, which can then be taken directly with water or by any other known means. Each possibility represents a separate embodiment of the present invention.

In some embodiments, the dietary composition is provided in a form of powder suitable as a supplement to beverages and food products, such as, milk, orange juice, mineral water, yogurt, pudding, salad, soup among others. Each possibility represents a separate embodiment of the present invention.

In some embodiments, the dietary composition of the invention is provided in a powder form suitable for reconstitution in aqueous solutions, including, suitable beverages, wherein the powder form comprises dehydrated mulberry extract, dehydrated coffee extract, dehydrated bean extract and, optionally, dehydrated arabinose. The powder may easily dissolve in the beverage or food products and may, or may not, add flavor thereto.

In some embodiments, the nutraceutical composition is provided in a form of granulate. The granulate may be used as a supplement to beverages and food products, such as, milk, orange juice, mineral water, yogurt, pudding, salad, soup among others. The granulate may easily dissolve in the beverage or food product and may, or may not, add additional flavor thereto.

The dietary compositions may also include a sweetener, a stabilizer, an antioxidant, an additive, a flavoring or a colorant. Each possibility represents a separate embodiment of the present invention.

In some embodiments, the composition further comprises flavoring agents, including, but not limited to, sweeteners (e.g. Aspartame), cinnamon, essential oil extracts, non-alcoholic favoring extracts, non-artificial fruit flavors, artificial extracts and combinations and/or extracts thereof. Each possibility represents a separate embodiment of the present invention.

Methods for preparing the oral forms are common knowledge. Tablets can, if desired, be coated or uncoated. Suitable tableting procedures include those generally described in Perry's Chemical Engineer's Handbook (4th Edition 1963) and in Pharmaceutical Dosage Forms: Tablets, volumes 1 and 2 (Marcel Dekker 1980) among others. The composition can also be administered in capsule form. The size of each dosage and the interval of dosing to the patient effectively determine the size and shape of the tablet or capsule. By present preference, each tablet or capsule contains the active ingredients in predetermined amounts to simplify treatment of the subject.

In some embodiments, there is provided a method for reducing blood glucose levels in a subject in need thereof comprising administering to the subject in need thereof a dietary composition comprising mulberry extract, coffee extract, bean extract as the nutraceutically active component and a nutraceutically acceptable carrier.

In some embodiments, the method of the invention is for ameliorating hyperglycemia. In some embodiments, the method of the invention is for ameliorating postprandial hyperglycemia. In some embodiments, the method of the invention is for maintaining glucose homeostasis.

In some embodiments, the method of the invention is for treating or preventing pathological conditions associated with hyperglycemia, such as, oxidative stress and inflammatory conditions, including, inflammation with pathologies, such as, diabetes (insulin resistance), endothelial dysfunction, hyperlipemia, fatty liver, cardiovascular diseases, visceral obesity, ectopic fat deposition (e.g. in skeletal muscles, liver, epicardial tissue, pericardial tissue) and dysfunction of adipocytes. Each possibility represents a separate embodiment of the present invention.

The term 'diabetes' as used herein encompasses, and is interchangeable with, Type-1 diabetes mellitus and Type-2 diabetes mellitus. Diabetes is a metabolic disorder characterized by high blood glucose levels or low glucose tolerance, and is estimated to affect 8% of the U.S. population. Diabetes is also significantly associated with higher risk of death from vascular disease, cancer, renal disease, infectious diseases, external causes, intentional self-harm, nervous system disorders, and chronic pulmonary disease. Metabolic syndrome, in which subjects present with central obesity and at least two other metabolic disorders (such as high cholesterol, high blood pressure, or diabetes) is estimated to affect 25% of the U.S. population. Obesity increases the likelihood to type II diabetes, hypertension, cardiovascular diseases, cancer, gall-stones, kidney dysfunction, arthrosis and joint-skeleton disorders and neurodegenerative diseases (such as, dementia, age dependent cognitive decline) among other diseases.

The term 'obesity' as used herein includes all forms of abnormal body weight and weight gain, with distinction that overweight refers to BMI 25-30 $kg/m^2$; obesity refers to BMI within the range of 30 to 35 $kg/m^2$, and morbid obesity refers to BMI higher than 35 $kg/m^2$. Obesity and overweight are estimated to affect about 65% of the U.S. adult population.

In some embodiments, the method is for inducing satiety.

The term 'satiety' refers to appetite control that may be induced by certain foods, such as, foods rich with fat. Satiety is associated with the absence of hungers, and/or the sensation of feeling full. Induction of satiety as used herein primarily refers to the sensation of being full after a normal-sized meal.

In some embodiments, the method is for decreasing postprandial insulin level.

In some embodiments, there is provided a method for preventing and/or treating hypoglycemia or a condition associated with hypoglycemia in a subject in need thereof, the method includes administering to the subject a dietary composition including mulberry extract, coffee extract and bean extract as the nutraceutically active components.

In some embodiments, the method of the invention is for ameliorating hypoglycemia. In some embodiments, the method of the invention is for ameliorating postprandial hypoglycemia. In some embodiments, the method of the invention is for treating or preventing pathological conditions associated with hypoglycemia, such as, insulin resistance, diabetes, prediabetes, hyperinsulinemia and dysphoria. Each possibility represents a separate embodiment of the present invention.

In some embodiments, ameliorating hypoglycemia comprises maintaining insulin homeostasis. In some embodiments, ameliorating hypoglycemia comprises reducing insulin level.

It is to be understood that, typically, insulin level is not merely associated with sugar levels, and accordingly, reduction of blood glucose may not necessarily entail reduction in insulin levels. Sugar lowering may be exerted by extra insulin secretion, which is not the case in most of the examples described hereinbelow. Thus, the dietary composition in addition to reducing blood glucose levels, also induces a reduction in insulin level. This effect is clinically highly desired as high levels of insulin are known to induce severe pathologies.

The terms "hypoglycemia", "reactive-hypoglycemia" or "postprandial hypoglycemia" as used herein are interchangeable and refer to a medical condition represented by recurrent episodes of symptomatic low blood sugar occurring after a high carbohydrate meal in non-diabetic subjects. Without being bound by any theory or mechanism, hypoglycemia may be a consequence of excessive insulin release triggered by food which continues past the digestion of glucose derived from the meal. Other causes of hypoglycemia may be excessive insulin produced in the body (hyperinsulinemia), inborn error of metabolism, medications and poisons, alcohol, hormone deficiencies, prolonged starvation, alterations of metabolism associated with infection and organ failure.

The level of blood glucose defining hypoglycemia may be different for different people, in different circumstances, and for different purposes. However most healthy adults maintain fasting glucose levels above, about, 72 mg/dl, and develop symptoms of hypoglycemia when the glucose falls below that level. In some embodiments, hypoglycemia refers to blood glucose levels below 75 mg/dl. In some embodiments, hypoglycemia refers to blood glucose levels below 70 mg/dl. In some embodiments, hypoglycemia refers to blood glucose levels below 65 mg/dl. In some embodiments, hypoglycemia refers to blood glucose levels below 60 mg/dl. In some embodiments, hypoglycemia refers to blood glucose levels below 55 mg/dl. In some embodiments, hypoglycemia refers to blood glucose levels below 50 mg/dl.

In some embodiments, the condition associated with hypoglycemia includes diabetes, prediabetes and insulin resistance.

In some embodiments, preventing hypoglycemia may include detaining progression of prediabetes or diabetes.

In some embodiments, preventing hypoglycemia may include detaining progression of insulin resistance.

In some embodiments, the method may further include treating prediabetes or diabetes.

In some embodiments, the method may further include treating insulin resistance.

In some embodiments, preventing and/or treating hypoglycemia may be maintained for at least one hour following administration of the dietary composition. In some embodiments, preventing and/or treating hypoglycemia is maintained for at least two hours following administration of the dietary composition.

In some embodiments, the composition for treating or prevention hypoglycemia is administered before intake of a meal. In some embodiments, the meal includes at least one food product having a high glycemic index.

In some embodiments, there is provided use of a dietary composition comprising mulberry extract, coffee extract, bean extract as the nutraceutically active component and a nutraceutically acceptable carrier for reducing blood glucose levels.

In some embodiments, there is provided use of a dietary composition comprising mulberry extract, coffee extract, bean extract as the nutraceutically active component and a nutraceutically acceptable carrier for managing weight gain, thereby losing weight and/or maintaining an acceptable body weight.

In some embodiments, there is provided use of a dietary composition comprising mulberry extract, coffee extract and bean extract as the nutraceutically active component and a nutraceutically acceptable carrier for the treatment of hypoglycemia and diseases or disorders associated therewith.

In some embodiments, there is provided use of a dietary composition comprising mulberry extract, coffee extract, bean extract as the nutraceutically active component and a nutraceutically acceptable carrier for maintaining blood glucose homeostasis.

In some embodiments, there is provided use of a dietary composition comprising mulberry extract, coffee extract, bean extract as the nutraceutically active component and a nutraceutically acceptable carrier for maintaining insulin homeostasis.

The term 'glucose homeostasis' as used herein refers primarily to postprandial glucose homeostasis, stated otherwise, blood glucose levels that are balanced and do not reach extremely high or extremely low glucose levels which are associated with hyperglycemia or hypoglycemia, respectively. Typically, glucose homeostasis in humans refers to blood glucose levels within the range of 70 to 130 mg/dL before meals and no more than 180 mg/dL after meals. In non-diabetic, postprandial glucose usually does not exceed 140 mg/dL and is typically maintained around 100 mg/dL.

The term 'insulin homeostasis' as used herein refers primarily to insulin levels that are balanced and do not reach extremely high or extremely low levels which are associated with pathologies. Typically, balanced insulin levels are within the range of 55 to 80 pmol/L and no more than 100 IU/ml.

In some embodiments, there is provided a method for managing weight gain, preventing gain of excess weight and/or inducing weight loss in a subject in need thereof, comprising administering to the subject in need thereof a dietary composition comprising mulberry extract, coffee extract, bean extract as the nutraceutically active component and a nutraceutically acceptable carrier.

The term 'weight gain' as used herein refers to weight gain normally incurred in a mammal subsequent to malnutrition, abnormal metabolism, post menopause, use of antipsychotics, castration, testosterone decline in men, ovariectomy and ovariohysterectomy among others.

The term 'excess weight' may refer to body mass exceeding the required BMI.

The dietary compositions of the invention are adapted for administration on a regular basis, including, but not limited to, on daily basis, weekly basis and biweekly basis.

The following examples are presented in order to more fully illustrate some embodiments of the invention. They should, in no way be construed, however, as limiting the broad scope of the invention.

EXAMPLES

Example 1: Effect of Single Plant Extracts on Postprandial Blood Glucose Levels In Vivo An experiment was conducted on 96 male Wistar rats with mean body weight of 381.2±16.6 g, bred at IARFR PAS in Olsztyn. Each study group consisted of 12 rats. The animals were kept in individual cages in a ventilated room at a constant temperature of about 22° C., controlled relative humidity of about 60% and appropriate lighting (day/night, 12/12 hours). During the experimental period, the animals were fed a standard laboratory rodent mix. Rats were deprived of food 12 hours prior to the first measurement of blood glucose levels, while constant access to water was maintained. On the day of the experiment, the rats were weighed and fasting blood glucose measurements were taken, via a scalpel incision at the tip of the tail. Next, the animals received aqueous solutions of plant extracts, Acarbose, which served as a positive control (PC) or water, which served as a negative control (NC) at pre-defined quantities via a gastric tube. All the plant extracts were provided by MarMar Investment in a solution form, and were administered according to the following doses:

white mulberry extract (mulberry): 120 mg per 1 kg body weight
bean extract: 100 mg per 1 kg body weight
green coffee extract (coffee): 20 mg per 1 kg body weight
bitter melon extract (melon): 150 mg per 1 kg body weight
pomelo extract: 100 mg per 1 kg body weight
acarbose preparation: 35 mg per 1 kg body weight
arabinose preparation: 25 mg per 1 kg body weight The extract solutions were prepared so as the amount of liquid administered to a sample animal weighing 350 g was 1 mL. Water was administered to the control group in the same manner/volume. Five minutes after the administration of the extracts each rat received a 50% aqueous solution of sucrose in the amount of 2 g/kg body weight via a gastric tube. Subsequent blood glucose levels measurements were taken after 15, 30, 60, 90, 120 and 180 minutes (counting from administration of the glucose solution) using Accu-Chek Go (Roche Diagnostics GmbH, Mannheim, Germany) glucometer and test strips.

Statistical analysis using Student's t-test was performed for proper interpretation of results. Each result obtained for a particular product was compared to the analogous result obtained in the negative control (water) group. Results are presented in Table 1, below.

TABLE 1

The effect of individual plant extracts on glucose tolerance tests

| Time (min) | 0 | 15 | 30 | 60 | 90 | 120 | 180 |
|---|---|---|---|---|---|---|---|
| GLUCOSE | | | | | | | |
| Water | 94.1 ± 7.33 | 176.4 ± 26.62 | 161.6 ± 16.54 | 157.1 ± 8.24 | 149.9 ± 9.87 | 142.7 ± 15.63 | 111.0 ± 13.00 |
| Acarbose | 95.6 ± 6.37 | 168.9 ± 16.33 | 163.3 ± 22.35 | 158.0 ± 12.91 | 157.6 ± 10.20 | 137.7 ± 10.07 | 106.8 ± 8.59 |
| Coffee | 95.0 ± 6.71 | 155.8 ± 15.08 | 140.9 ± 16.25 | 140.2 ± 11.58 | 142.5 ± 10.44 | 135.6 ± 9.63 | 110.0 ± 8.68 |
| Bean | 91.9 ± 5.66 | 150.8 ± 15.59 | 144.5 ± 17.21 | 146.6 ± 9.16 | 148.7 ± 9.51 | 136.0 ± 7.68 | 107.5 ± 9.71 |
| Mulberry | 93.2 ± 4.91 | 157.0 ± 26.39 | 139.2 ± 12.98 | 148.0 ± 12.37 | 143.2 ± 14.09 | 131.7 ± 11.69 | 110.7 ± 11.50 |
| Pomelo | 93.2 ± 6.90 | 151.2 ± 16.56 | 150.5 ± 18.67 | 155.5 ± 7.34 | 151.6 ± 8.17 | 141.9 ± 7.49 | 107.6 ± 6.65 |
| Melon | 95.7 ± 6.37 | 190.3 ± 17.80 | 150.7 ± 20.75 | 157.8 ± 10.16 | 143.6 ± 10.52 | 135.9 ± 14.56 | 111.8 ± 13.67 |
| Arabinose | 96.0 ± 3.62 | 170.9 ± 19.55 | 157.1 ± 20.27 | 148.2 ± 18.33 | 152.2 ± 11.19 | 137.0 ± 8.96 | 111.6 ± 14.42 |
| SUCROSE | | | | | | | |
| Water | 94.1 ± 6.19 | 157.6 ± 21.74 | 141.2 ± 15.27 | 136.5 ± 7.49 | 130.1 ± 8.83 | 121.5 ± 9.06 | 112.2 ± 6.81 |
| Acarbose | 94.2 ± 7.43 | 120.0 ± 15.80 | 114.9 ± 14.48 | 100.1 ± 7.28 | 95.5 ± 6.17 | 94.6 ± 6.02 | 90.0 ± 6.21 |
| Coffee | 93.7 ± 5.82 | 138.9 ± 11.29 | 123.6 ± 5.93 | 124.4 ± 5.93 | 125.9 ± 7.50 | 121.1 ± 7.06 | 115.2 ± 8.13 |
| Bean | 93.5 ± 6.52 | 135.2 ± 15.21 | 129.8 ± 11.20 | 126.5 ± 7.42 | 121.0 ± 7.16 | 118.8 ± 7.41 | 107.6 ± 4.50 |
| Mulberry | 96.2 ± 6.57 | 128.8 ± 16.08 | 133.8 ± 12.69 | 121.3 ± 4.19 | 116.5 ± 5.13 | 113.7 ± 5.85 | 108.5 ± 5.28 |
| Pomelo | 92.7 ± 3.94 | 143.7 ± 15.18 | 131.5 ± 11.12 | 128.2 ± 12.04 | 123.7 ± 9.49 | 119.2 ± 6.26 | 106.7 ± 5.19 |
| Melon | 95.8 ± 3.94 | 140.9 ± 15.83 | 132.8 ± 6.85 | 129.7 ± 8.96 | 127.3 ± 8.60 | 120.0 ± 7.19 | 115.8 ± 6.73 |
| Arabinose | 94.7 ± 7.31 | 135.4 ± 14.68 | 132.9 ± 15.65 | 132.9 ± 9.06 | 131.7 ± 7.55 | 125.4 ± 6.52 | 123.0 ± 7.25 |

TABLE 1-continued

The effect of individual plant extracts on glucose tolerance tests

| Time (min) | 0 | 15 | 30 | 60 | 90 | 120 | 180 |
|---|---|---|---|---|---|---|---|
| STARCH | | | | | | | |
| Water | 91.2 ± 2.82 | 128.7 ± 7.64 | 130.6 ± 6.67 | 124.5 ± 9.22 | 118.5 ± 7.68 | 114.0 ± 6.74 | 105.2 ± 7.27 |
| Acarbose | 93.5 ± 6.36 | 120.0 ± 14.97 | 114.9 ± 14.48 | 100.1 ± 7.28 | 95.5 ± 6.17 | 94.6 ± 6.02 | 90.0 ± 7.03 |
| Coffee | 93.4 ± 4.74 | 125.1 ± 11.16 | 123.7 ± 9.84 | 118.8 ± 8.96 | 111.5 ± 7.33 | 113.2 ± 5.12 | 105.5 ± 4.78 |
| Bean | 90.9 ± 5.92 | 141.2 ± 18.84 | 130.4 ± 9.14 | 123.0 ± 9.05 | 119.3 ± 6.91 | 115.6 ± 5.74 | 105.1 ± 6.37 |
| Mulberry | 91.1 ± 5.20 | 119.2 ± 8.75 | 120.5 ± 7.66 | 116.7 ± 10.36 | 111.4 ± 5.40 | 108.1 ± 5.68 | 98.5 ± 4.12 |
| Pomelo | 92.0 ± 5.51 | 120.8 ± 10.04 | 124.7 ± 8.57 | 117.7 ± 7.44 | 115.8 ± 6.06 | 110.7 ± 5.67 | 103.8 ± 7.31 |
| Melon | 92.9 ± 5.84 | 124.8 ± 8.97 | 130.7 ± 10.91 | 117.9 ± 8.59 | 113.8 ± 9.68 | 107.5 ± 8.09 | 106.4 ± 6.64 |
| Arabinose | 90.9 ± 5.92 | 116.3 ± 8.88 | 123.5 ± 12.49 | 110.9 ± 7.28 | 111.5 ± 4.19 | 106.3 ± 6.54 | 100.1 ± 6.33 |

Figure 2:
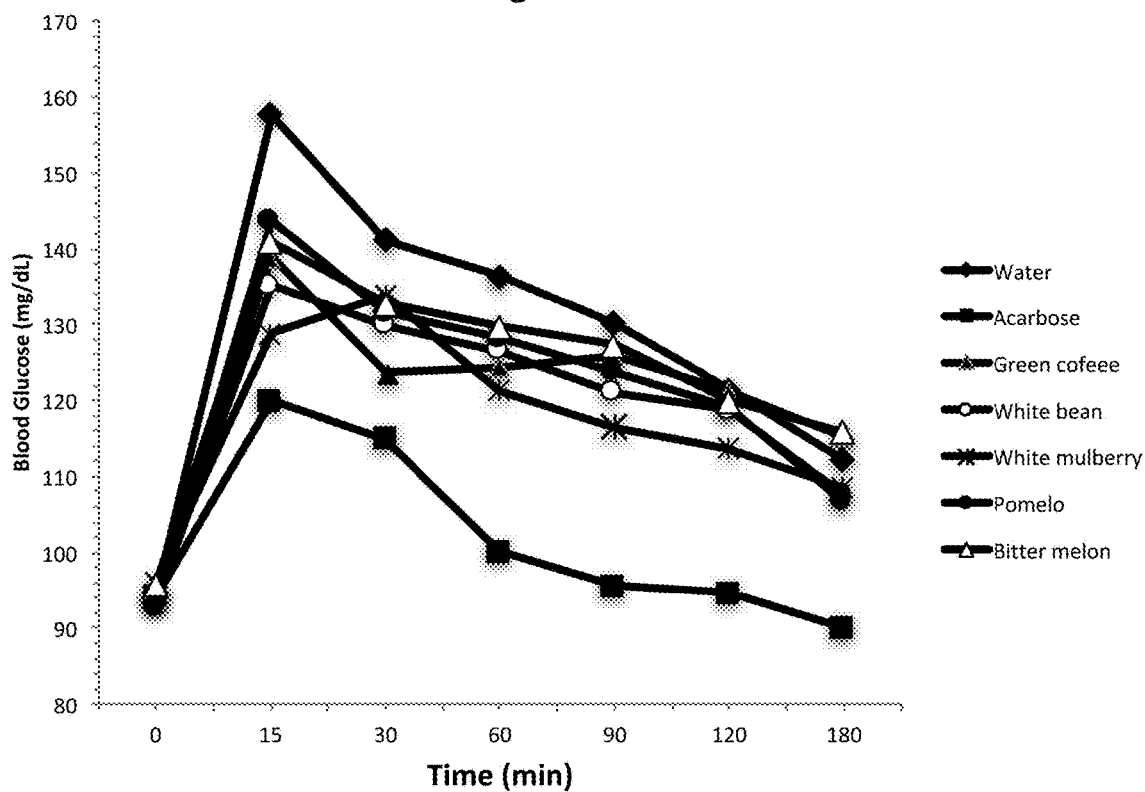
FIG. 2 represents glucose tolerance test following administration of 50% sucrose solution in rats receiving plant extract selected from pomelo, bitter melon, white mulberry, white bean, green coffee, arabinose, acarbose as a positive control and water as a negative control.
Figure 3:
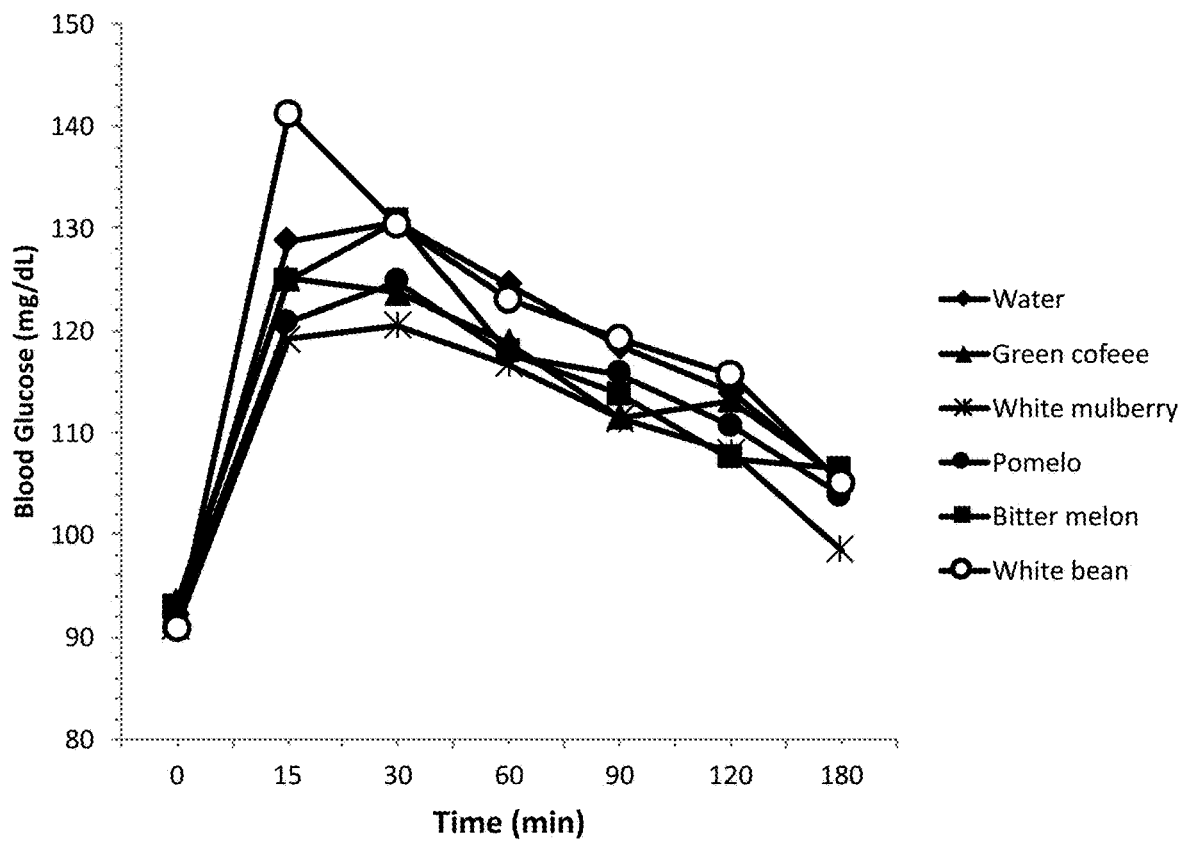
FIG. 3 represents glucose tolerance test following administration of 40% starch solution in rats receiving a plant extract selected from pomelo, white mulberry, white bean, green coffee, bitter melon and water as a negative control.

FIGS. 1 to 3 exhibit all glucose tolerance tests, expressing blood glucose levels at different time points after administration of 50% glucose solution (FIG. 1), 50% sucrose solution (FIG. 2) and 40% starch solution (FIG. 3), as measured in rats fed on a diet supplemented with individual plant extracts: pomelo, bitter melon, white mulberry, green coffee, arabinose, acarbose (positive control). Water without any supplements served as negative control. Fasting blood glucose levels in all groups of rats subjected to the tolerance tests ranged between 90.9 and 96.2 mg/dL.

Figure 4:
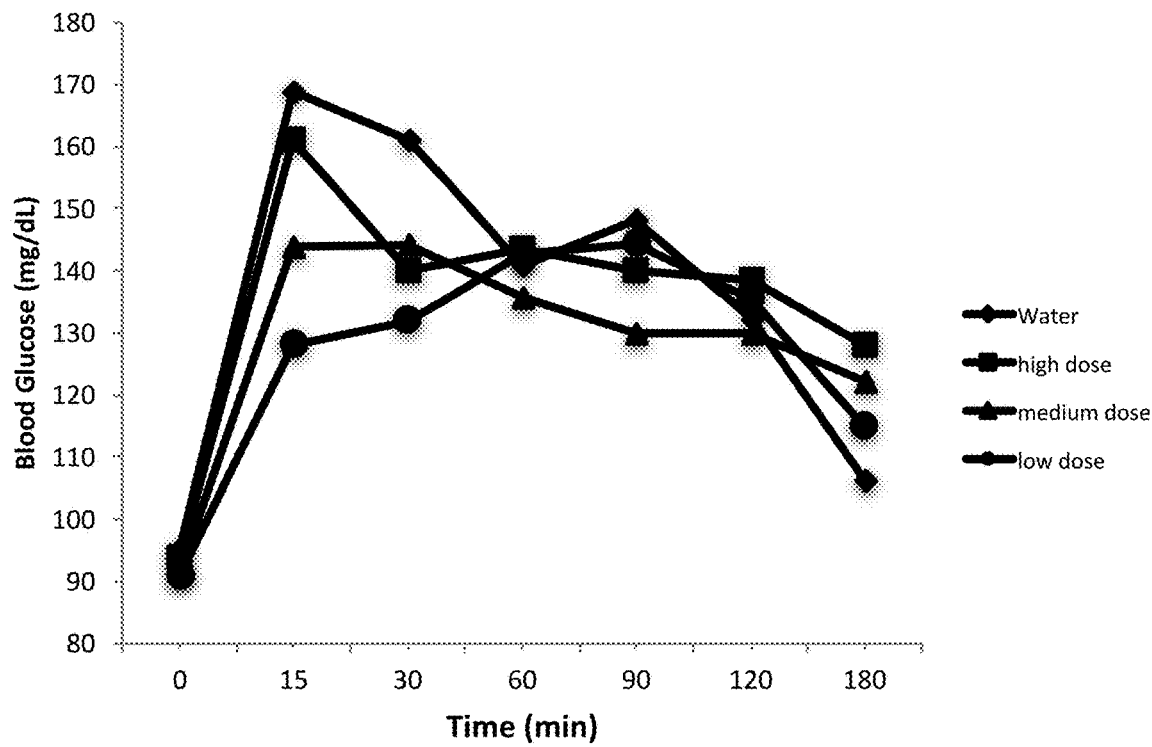
FIG. 4 represents glucose tolerance test following administration of 50% glucose solution in rats receiving spinach (thylakoids) at high dose (1,000 mg/kg body weight), medium dose (500 mg/kg body weight; triangle) and low dose (250 mg/kg body weight), and water as a negative control.

FIG. 4 exhibits glucose tolerance tests, expressing blood glucose levels at different time points after administration of 50% glucose solution in rats receiving spinach thylakoids) at high, medium and low doses (1000, 500 and 250 mg/kg body weight, respectively). Water without any supplements served as negative control. Fasting blood glucose levels in all groups of rats subjected to the tolerance tests ranged around 90 to 95 mg/dL.

Altogether the results indicate that each of the plant extracts, when administered alone, exerts an inconsistent, and to some extent random, effect on glucose levels. At most, the tested plant extracts reduced blood glucose levels merely at early time points (compared to the acarbose). However, blood glucose levels following administration of individual plant extracts was well above blood glucose levels in rats receiving acarbose.

Example 2: Plant Extract Combinations Reduce Blood Glucose Levels In Vivo

The effect of plant extract combinations was tested in an experiment conducted with 50 male Wistar rats having mean body weight of 294.9±21.0 g, bred at IARFR PAS in Olsztyn. Each study group consisted of 10 rats. Rats were kept in individual cages in a ventilated at a constant temperature of about 22° C., controlled relative humidity of about 60% and appropriate lighting (day/night, 12/12 hours). During the experimental period, rats were fed the standard laboratory rodent mix. Rats were deprived of food 12 hours prior to the first measurement of blood glucose levels, while constant access to water was maintained. On the day of the experiment, rats were weighed and fasting blood glucose measurements were taken, via a scalpel incision at the tip of the tail. Next, rats were administered water (negative control), acarbose (positive control) or aqueous solutions of pre-defined combinations of plant extracts, as follows:

acarbose preparation: 35 mg per 1 kg body weight combination I: white mulberry extract (120 mg per 1 kg body weight)+ bean extract (100 mg per 1 kg body weight)+ green coffee extract (20 mg per 1 kg body weight).

combination II: white mulberry extract (120 mg per 1 kg body weight)+ green coffee extract (20 mg per 1 kg body weight)+ arabinose preparation (25 mg per 1 kg body weight).

combination III: white mulberry extract (120 mg per 1 kg body weight)+ bean extract (100 mg per 1 kg body weight)+ green coffee extract (20 mg per 1 kg body weight)+ arabinose preparation (25 mg per 1 kg body weight).

The solutions of the extracts were prepared so that the volume of liquid administered to an animal weighing 350 g was 1 mL. Water was administered to the control group in a similar manner. Five minutes after administration of the extracts each rat received 50% aqueous solution of sucrose in the amount of 2 g/kg body weight (A) or 40% aqueous solution of starch in the amount of 2 g/kg body weight (B). Subsequent blood glucose levels measurements were taken after 15, 30, 60, 90, 120 and 180 minutes (counting from administration of the sucrose solution) using Accu-Chek Go (Roche Diagnostics GmbH, Mannheim, Germany) glucometer and test strips.

Statistical analysis using Student's t-test was performed for proper interpretation of results. Each result obtained for a particular product was compared to the analogous result obtained in the negative control (water) group. Results are presented in Table 2, below and in FIGS. 5A-5B.

TABLE 2

The effect of plant extract combinations on blood glucose in rats

| Time (min) | 0 | 15 | 30 | 60 | 90 | 120 | 180 |
|---|---|---|---|---|---|---|---|
| SUCROSE | | | | | | | |
| Water | 82.7 ± 4.32 | 155.6 ± 10.4 | 152.1 ± 12.1 | 151.4 ± 6.46 | 142.2 ± 5.18 | 128.0 ± 7.71 | 113.1 ± 6.08 |
| Acarbose | 84.7 ± 4.81 | 112.2 ± 8.58 | 121.1 ± 8.93 | 116.0 ± 6.87 | 110.2 ± 6.51 | 109.0 ± 4.66 | 101.1 ± 5.34 |
| Comb. I | 87.4 ± 9.55 | 113.0 ± 9.70 | 130.8 ± 6.40 | 123.7 ± 7.07 | 121.0 ± 7.51 | 116.6 ± 7.91 | 113.5 ± 6.70 |
| Comb. II | 89.3 ± 9.29 | 123.8 ± 7.59 | 128.3 ± 8.06 | 122.4 ± 5.62 | 120.2 ± 6.49 | 115.5 ± 6.68 | 110.6 ± 6.11 |
| Comb. III | 83.9 ± 6.72 | 121.4 ± 9.65 | 132.0 ± 8.89 | 127.5 ± 5.89 | 122.0 ± 5.45 | 119.9 ± 6.83 | 111.6 ± 9.13 |

TABLE 2-continued

The effect of plant extract combinations on blood glucose in rats

| Time (min) | 0 | 15 | 30 | 60 | 90 | 120 | 180 |
|---|---|---|---|---|---|---|---|
| STARCH | | | | | | | |
| Water | 89.2 ± 7.68 | 118.5 ± 7.96 | 125.5 ± 8.26 | 121.7 ± 4.85 | 120.3 ± 6.46 | 118.3 ± 6.11 | 109.8 ± 7.71 |
| Acarbose | 89.7 ± 6.09 | 105.5 ± 9.74 | 104.6 ± 4.24 | 97.3 ± 7.18 | 98.3 ± 6.09 | 94.8 ± 6.01 | 88.7 ± 4.87 |
| Comb. I | 89.0 ± 5.33 | 113.2 ± 8.29 | 117.9 ± 6.47 | 113.8 ± 4.59 | 110.7 ± 5.49 | 106.2 ± 7.14 | 94.1 ± 6.24 |
| Comb. II | 92.2 ± 4.31 | 115.5 ± 6.94 | 117.0 ± 6.46 | 112.4 ± 6.16 | 110.9 ± 9.20 | 108.3 ± 8.60 | 96.5 ± 5.56 |
| Comb. III | 87.8 ± 3.70 | 112.1 ± 8.18 | 115.2 ± 7.72 | 113.7 ± 10.5 | 107.1 ± 6.41 | 107.3 ± 7.76 | 92.5 ± 11.3 |

Fasting blood glucose levels in all groups of rats subjected to the sucrose tolerance test ranged between 82.7 to 89.3 mg/dL.

Figure 5A:
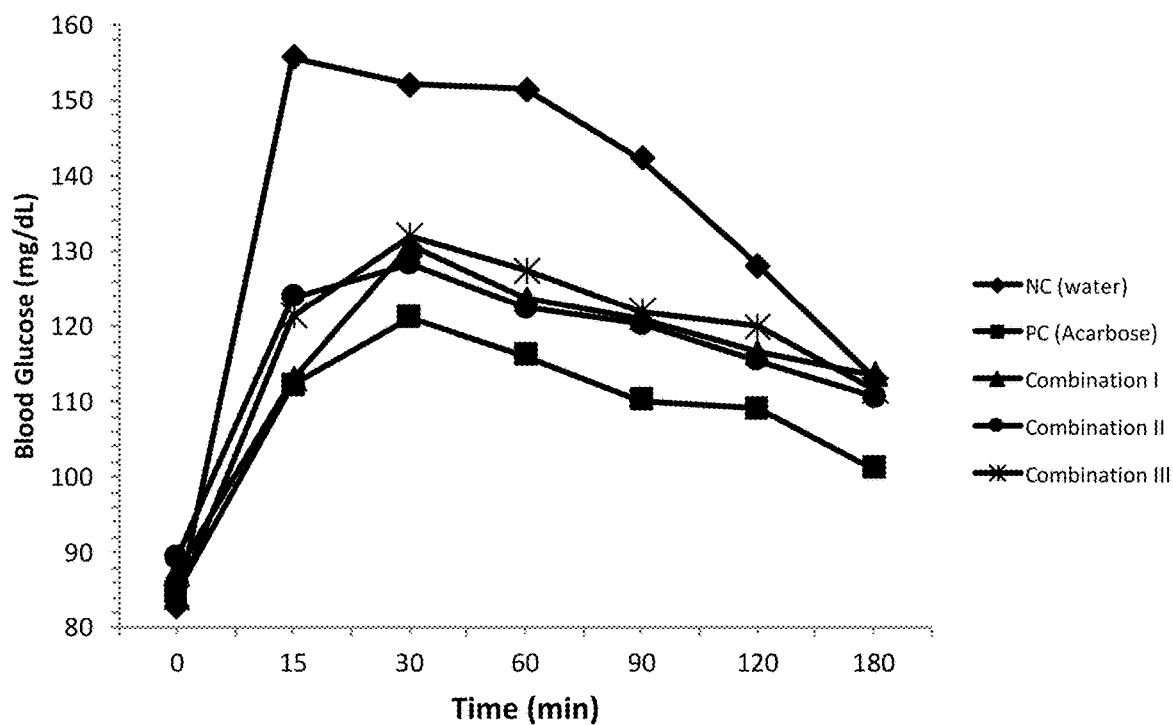
FIG. 5 exhibits glucose tolerance test following administration of 50% sucrose solution (A) or 40% starch solution (B), in rats receiving plant extract combination I, combination II, combination III, acarbose as a positive control and water as a negative control.
Figure 5B:
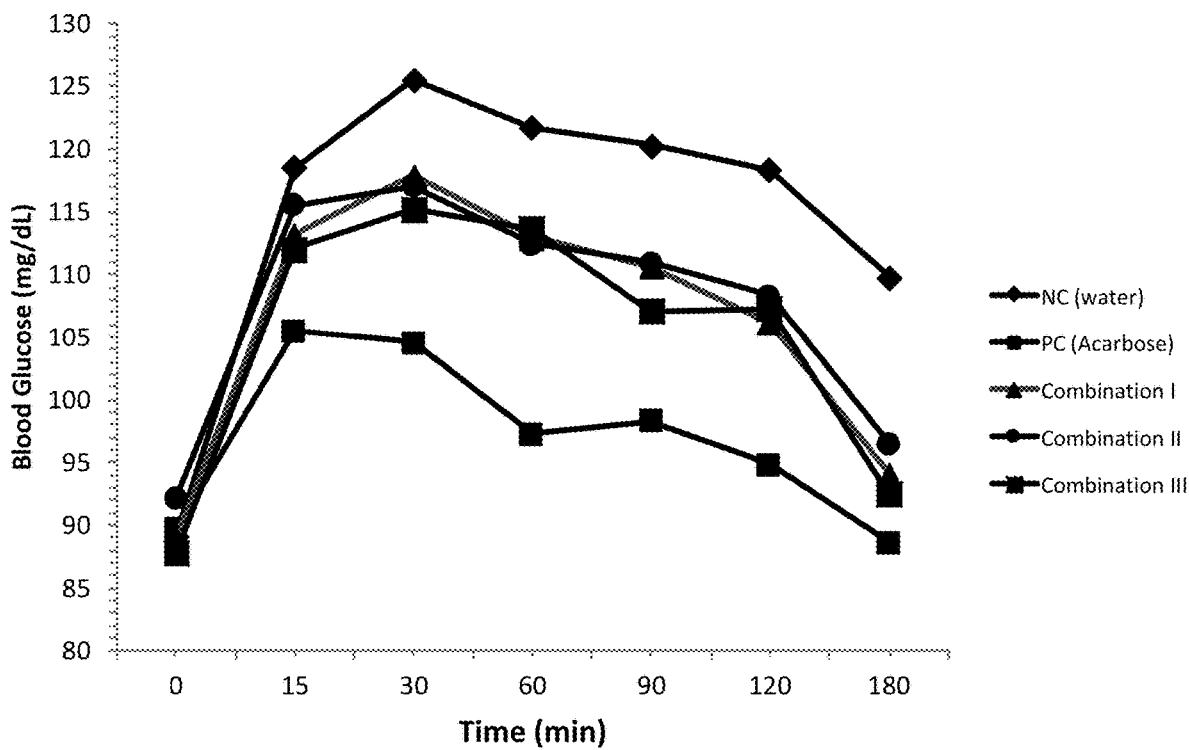

As shown in FIGS. 5A and 5B, it was surprisingly found that upon administration of each of the plant extract combinations a significantly milder surge in blood glucose levels was observed, which lasted more than two hours after administration of a solution of 50% sucrose (FIG. 5A) or 40% starch (FIG. 5B). In fact, blood glucose levels in rats receiving the plant extract combinations were comparable to blood glucose levels in rats receiving the anti-diabetic drug acarbose. Moreover, blood glucose levels in rats receiving the plant extract combinations were significantly lower than blood glucose levels in the control group (water).

Unexpectedly, combination I (triangles) including white mulberry extract (120 mg per 1 kg body weight), bean extract (100 mg per 1 kg body weight) and green coffee extract (20 mg per 1 kg body weight) inhibited the initial burst in blood glucose, measured 15 min after commencement of the test, to the same level as acarbose, whereas combination III (asterisk) containing 25 mg per 1 kg body weight arabinose in addition to the components of combination I had a somewhat relegated initial effect.

Figure 6:
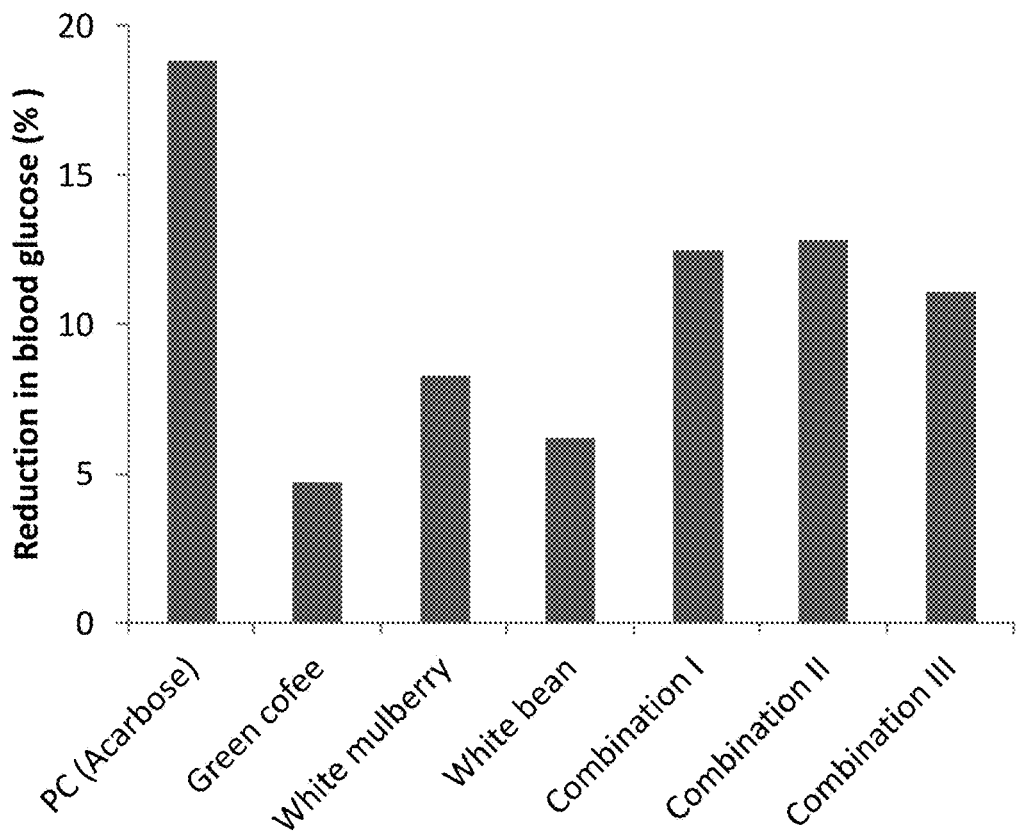
FIG. 6 shows blood glucose levels (AUC) exerted by acarbose (positive control), extracts of green coffee, white bean and white mulberry, and plant extract combinations no. I, II and III relative to negative control (water; 100%) in rats fed on 50% sucrose.
Figure 7:
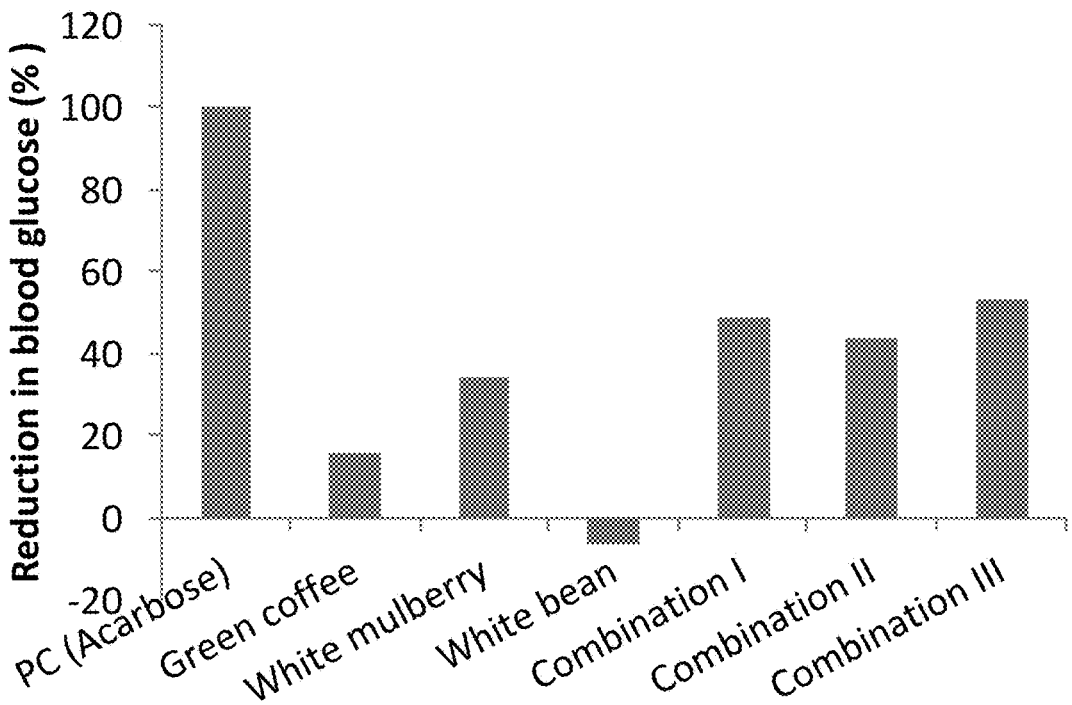
FIG. 7 shows blood glucose levels (AUC) exerted by acarbose (positive control), extracts of green coffee, white bean and white mulberry, and plant extract combination no. I, II and III relative to negative control (water; 100%) in rats fed on 40% starch.

Furthermore, overall reduction in blood glucose levels during the entire test, represented by %-reduction in the area under the curve (AUC) as compared to control (water), is significantly improved when combinations of plant extracts are administered to rats fed on 50% sucrose (FIG. 6) or 40% starch (FIG. 7) as compared to single extracts of green coffee and white mulberry and resemble the AUC obtained following acarbose administration.

Example 3: Plant Extract Combinations Reduce Blood Glucose Levels in Obese Rats In order to assess whether administration of plant extracts as dietary supplements can positively affect blood glucose levels in animals fed on a high-fat diet an in vivo experiment was performed in two stages: a preliminary stage and a test stage, each lasting 10 weeks. During the preliminary stage, a group of 40 Wistar rats aged about 35 days, originating from a single pack of the IARFR animal house were fed a commercial high fat diet C 1090-45 (Altromin GmbH, Lage, Germany) consisting of 21% crude protein, 22% crude fat, 3.95% crude fiber and 5.1% crude ash. A second group of 10 rats from the same pack and of the same age were fed a commercial low fat diet C 1090-10 (Altromin GmbH, Lage, Germany) consisting of 21% crude protein, 3.9% crude fat, 4.0% crude fiber and 4.7% crude ash. The above diets were significantly different in metabolic energies (ME) obtained from individual components. The details of the diets used in the current experiment are presented in Table 3 below.

TABLE 3

Dietary compositions (%)

| Ingredient | K | HF | T | P | TP |
|---|---|---|---|---|---|
| Casein | 22.5 | 22.5 | 22.5 | 22.5 | 22.5 |
| Cellulose | 5 | 5 | 5 | 5 | 5 |
| Oil | 5 | — | — | — | — |
| Lard | — | 24 | 24 | 24 | 24 |
| Vitamin mix[1] | 1 | 1 | 1 | 1 | 1 |
| Mineral mix[1] | 3.5 | 3.5 | 3.5 | 3.5 | 3.5 |
| Choline chloride | 0.2 | 0.2 | 0.2 | 0.2 | 0.2 |
| DL-methionine | 0.2 | 0.2 | 0.2 | 0.2 | 0.2 |
| Maize starch | 62.6 | 43.6 | 41.95 | 42.808 | 41.158 |
| Thylacoids | — | — | 1.65 | — | 1.65 |
| White mulberry extract | — | — | — | 0.396 | 0.396 |
| Bean extract | — | — | — | 0.330 | 0.330 |
| Green coffee extract | — | — | — | 0.066 | 0.066 |

| Dietary Energy (%) | | | | | |
|---|---|---|---|---|---|
| Protein | 23 | 19 | 19 | 19 | 19 |
| Carbohydrates | 65 | 36 | 36 | 36 | 36 |
| Fat | 12 | 45 | 45 | 45 | 45 |

[1]AIN-93MX and AIN-93VM, composition consistent with the recommendations of the American Institute of Nutrition (Reeves, 1997)

Following the 10-week preliminary nutrition period (first period), rats fed the low fat diet served as a control group (K; n=10), while the animals fed with the high-fat diet were divided into 4 study groups (10 rats per group). Group HF continued to receive the high fat diet, group T received the high fat diet supplemented with thylacoids (500 mg/kg body mass), group P received the high fat diet supplemented with plant extract combination I (white mulberry 120 mg/kg body mass, bean 100 mg/kg body mass, green coffee 20 mg/kg body mass) and group TP received the high fat diet supplemented with both thylacoids and plant extract combination I. During the 10 weeks test stage (second period) the animals were fed with diets prepared by the DBFoF team.

Rats were deprived of food for 10-12 hours prior to concluding the experiment. On the day of the experiment ended, animals were sacrificed by an intraperitoneal injection of a mixture of xylazine and ketamine, in line with the institutional procedures of the DBFoF and appropriate recommendations on laboratory animals. Blood samples were collected from the caudal caval vein into heparinized tubes. Heparinized blood was centrifuged (350× g, 10 min, 4° C.), and plasma was separated and stored at −20° C. until the analyses. Colorimetric methods were used to determine the levels of glucose (GL).

Body mass and dietary intake were evaluated during the second period and the results are summarized in Table 4 below and in FIGS. 8-9. Statistical analysis was carried out using STATISTICA v. 8.0 package (StatSoft Corp., Kraków). One-factor ANOVA analysis was used to assess the effect of the dietary composition on the analyzed parameters. Results are presented as means with the overall standard error of means (SEM) as a measure of variability.

The overall SEM was calculated by dividing the standard deviation of the means in all groups by the square root of the total number of animals involved in the experiment. The significance level of P<0.05 was assumed for the statistical significance analysis.

TABLE 4

Body mass (BM), and dietary intake (D.I.) during the second period

| Parameter | Diet | | | | | SEM | P |
|---|---|---|---|---|---|---|---|
| | K | HF | T | P | TP | | |
| Week 1 | | | | | | | |
| BM (g) | 360.9$^b$ | 391.6$^a$ | 390.3$^a$ | 386.3$^{ab}$ | 385.4$^{ab}$ | 4.074 | 0.029 |
| D.I. (g/rat/day) | 125.8 | 116.7 | 117.1 | 123.5 | 126.4 | 1.674 | 0.100 |
| Week 2 | | | | | | | |
| BM (g) | 371.3$^b$ | 402.3$^a$ | 404.2$^a$ | 399.6$^a$ | 398.8$^a$ | 4.216 | 0.022 |
| D.I. (g/rat/day) | 129.9$^a$ | 104.7$^b$ | 106.0$^b$ | 108.1$^b$ | 104.7$^b$ | 1.990 | 0.000 |
| Week 3 | | | | | | | |
| BM (g) | 381.0$^b$ | 414.6$^a$ | 415.4$^a$ | 410.5$^a$ | 412.5$^a$ | 4.333 | 0.019 |
| D.I. (g/rat/day) | 136.2$^a$ | 111.7$^b$ | 107.3$^b$ | 108.7$^b$ | 106.5$^b$ | 1.931 | 0.000 |
| Week 4 | | | | | | | |
| BM (g) | 392.9$^b$ | 426.4$^a$ | 427.3$^a$ | 420.4$^a$ | 425.0$^a$ | 4.445 | 0.023 |
| D.I. (g/rat/day) | 128.9$^a$ | 112.1$^b$ | 106.7$^b$ | 104.6$^b$ | 105.9$^b$ | 1.672 | 0.000 |
| Week 5 | | | | | | | |
| BM (g) | 395.2$^b$ | 436.3$^a$ | 435.0$^a$ | 426.9$^a$ | 435.5$^a$ | 4.793 | 0.008 |
| D.I. (g/rat/day) | 122.0$^a$ | 108.8$^b$ | 101.3$^{bc}$ | 100.4$^c$ | 104.7$^{bc}$ | 1.590 | 0.000 |
| Week 6 | | | | | | | |
| BM (g) | 396.9$^b$ | 439.9$^a$ | 440.0$^a$ | 430.2$^a$ | 441.2$^a$ | 4.851 | 0.004 |
| D.I. (g/rat/day) | 123.1$^a$ | 104.4$^b$ | 99.4$^b$ | 97.2$^b$ | 102.6$^b$ | 1.711 | 0.000 |
| Week 7 | | | | | | | |
| BM (g) | 403.6$^b$ | 449.5$^a$ | 447.9$^a$ | 437.9$^a$ | 449.2$^a$ | 4.754 | 0.002 |
| D.I. (g/rat/day) | 127.6$^a$ | 106.4$^b$ | 100.2$^b$ | 99.9$^b$ | 102.7$^b$ | 1.797 | 0.000 |
| Week 8 | | | | | | | |
| BM (g) | 411.3$^b$ | 456.0$^a$ | 456.5$^a$ | 447.2$^a$ | 460.0$^a$ | 4.919 | 0.002 |
| D.I. (g/rat/day) | 129.3$^a$ | 108.9$^b$ | 105.5$^b$ | 105.4$^b$ | 105.4$^b$ | 1.692 | 0.000 |
| Week 9 | | | | | | | |
| BM (g) | 419.9$^b$ | 473.1$^a$ | 467.8$^a$ | 458.8$^a$ | 468.0$^a$ | 5.131 | 0.001 |
| D.I. (g/rat/day) | 128.3$^a$ | 115.9$^b$ | 101.5$^c$ | 105.1$^c$ | 98.6$^c$ | 1.877 | 0.000 |
| Week 10 | | | | | | | |
| BM (g) | 426.9$^b$ | 484.4$^a$ | 476.2$^a$ | 468.9$^a$ | 475.4$^a$ | 5.220 | 0.002 |
| D.I. (g/rat/day) | 119.1$^a$ | 101.7$^b$ | 94.4$^b$ | 96.2$^b$ | 93.9$^b$ | 2.182 | 0.000 |
| Intake weeks 1-10 | 1270$^a$ | 1091$^b$ | 1039$^b$ | 1050$^b$ | 1051$^b$ | 15.71 | 0.000 |

$^a$SEM: standard error of the mean, SD for all rats divided by the square root of the total number of rats, n = 50.
$^b$Means with different superscript index letters within the same rows are different at P ≤ 0.05.

Figure 8:
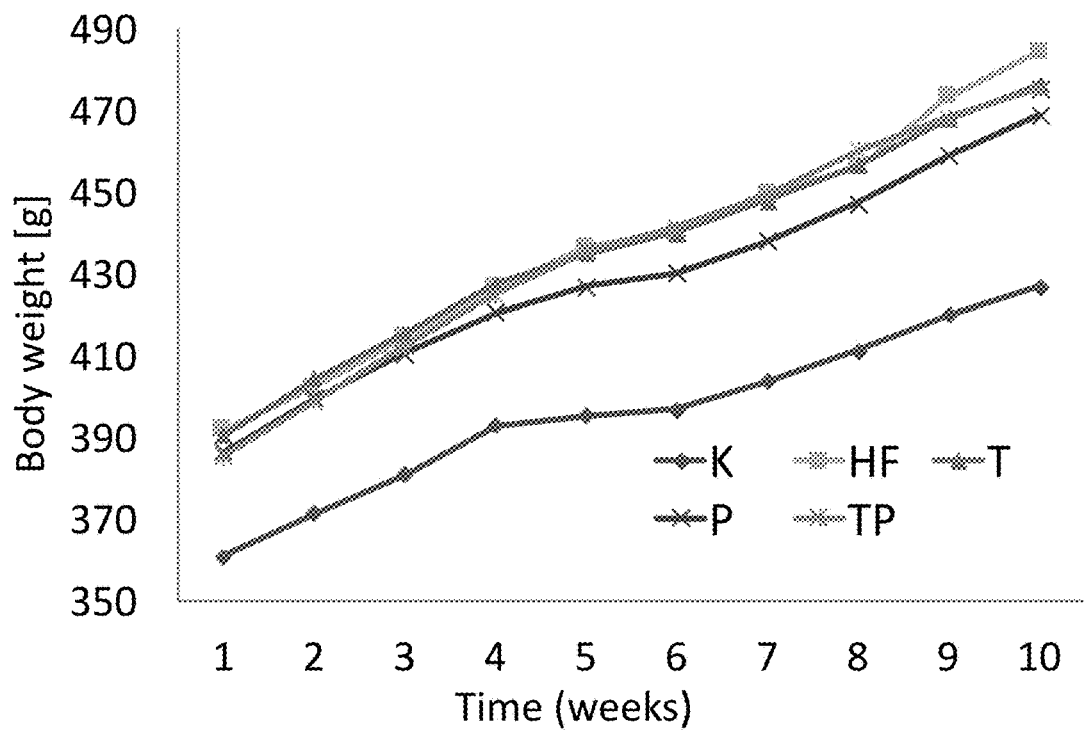
FIG. 8 exhibits body mass in rats having diet induced obesity, during 10 weeks of feeding on high-fat diet (HF) supplemented with thylakoids (T), plant extract combination no. I (P) and the combination of thylakoids with plant extract combination no. I (TP).
Figure 9:
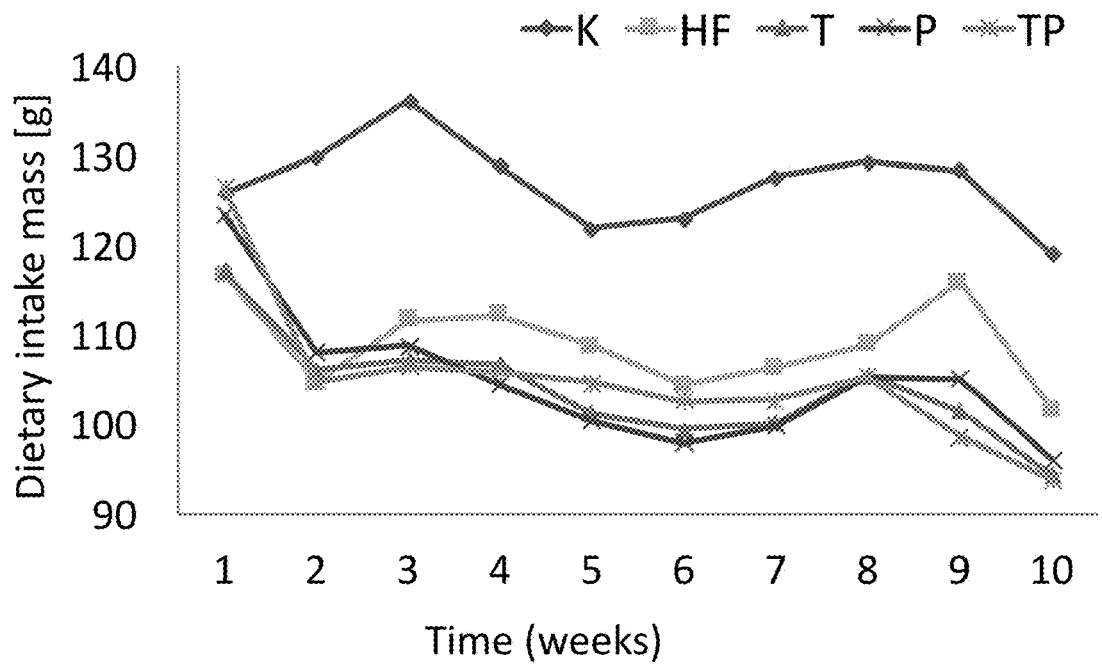
FIG. 9 exhibits dietary intake in rats having diet induced obesity, during 10 weeks of feeding on high-fat diet (HF) supplemented with thylakoids (T), plant extract combination no. I (P) and the combination of thylakoids with plant extract combination no. I (TP).

As indicated by the data presented in Table 4, and in corresponding FIGS. 8 and 9, among the high-fat groups, the highest final body mass was observed in group HF (484.4 g), namely, the group having a diet devoid of plant extracts supplements. Moreover, the lowest final body mass was observed in group P (468.9 g) which received a high-fat diet supplemented with plant extract combination no. I. Furthermore, dietary intake in all diets supplemented with plant extracts (P, T and PT) was significantly lower compared to the non-supplemented high-fat diet (HF), suggesting that supplementing the diet with the plant extract combinations of the invention induces satiety.

Figure 10:
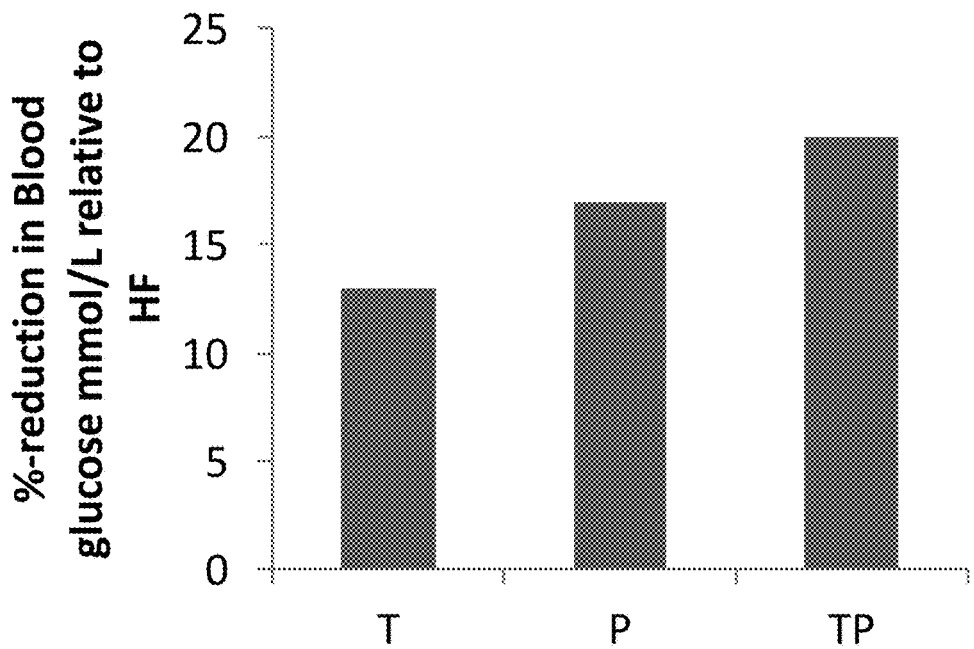
FIG. 10 shows reduction in blood glucose level in rats fed on high fat diet supplemented with thylakoids (T), plant extract combination no. I (P) and the combination of thylakoids with plant extract combination no. I (TP), relative to rats fed on high-fat diet devoid of supplements.

Moreover, in rats receiving the high fat diet supplemented with combination no. I of the plant extracts (P) a 17% reduction in blood glucose levels was observed (FIG. 10). Similarly, rats receiving high fat diet supplemented with thylakoids (T) showed a 13% reduction in blood glucose levels (FIG. 10). Surprisingly, high-fat diet supplemented with both thylakoids and plant extracts (TP) resulted in a significant 20% reduction in the blood glucose levels (FIG. 10).

Example 4: The Effect of Plant Extract Combinations and/or Dietary Fibers on Blood Glucose Levels, Body Mass and Dietary Intake in Diet-Induced Obese Rats In order to assess whether administration of plant extracts and/or dietary fibers can positively affect blood glucose levels in rats fed on a high-fat diet an in vivo assay was performed essentially as described in Example 3. The compositions of the diets are presented in Table 5 below.

TABLE 5

Diet composition (%)

| Ingredient | K | HF | G | GP |
|---|---|---|---|---|
| Casein | 22.5 | 22.5 | 22.5 | 22.5 |
| Cellulose | 5 | 5 | 5 | 5 |
| Oil | 5 | — | — | — |
| Lard | — | 24 | 24 | 24 |
| Vitamin mix | 1 | 1 | 1 | 1 |
| Mineral mix | 3.5 | 3.5 | 3.5 | 3.5 |
| Choline chloride | 0.2 | 0.2 | 0.2 | 0.2 |
| DL-methionine | 0.2 | 0.2 | 0.2 | 0.2 |
| Maize starch | 62.6 | 43.6 | 42.01 | 41.268 |
| Glucomannan | — | — | 0.954 | 0.954 |
| Inulin | — | — | 0.636 | 0.636 |
| White mulberry extract | — | — | — | 0.371 |
| Bean extract | — | — | — | 0.309 |
| Green coffee extract | — | — | — | 0.062 |

Dietary Energy (%)

| | K | HF | G | GP |
|---|---|---|---|---|
| Protein | 23 | 19 | 19 | 19 |
| Carbohydrates | 65 | 36 | 36 | 36 |
| Fat | 12 | 45 | 45 | 45 |

Following the 10-week preliminary nutrition period (first period), rats fed the low fat diet served as a control group (K; n=10), while the animals fed with the high-fat diet were divided into 3 study groups (10 rats per group). Group HF continued to receive the high fat diet, group G received the high fat diet supplemented with dietary fibers (60% w/w glucomannan, 40% w/w inulin, 514 mg/kg body mass), and group GP received the high fat diet supplemented with plant extract combination I (white mulberry 120 mg/kg body mass, bean 100 mg/kg body mass, green coffee 20 mg/kg body mass) and dietary fibers (second period). Body mass and dietary intake were evaluated during the second period and the results are summarized in Table 6 below.

TABLE 6

Body mass (BM), and dietary intake (D.I.) during the second period

| Parameter | K | HF | G | GP | SEM | P |
|---|---|---|---|---|---|---|
| Week 1 | | | | | | |
| BM (g) | $385.9^b$ | $412.9^a$ | $412.8^a$ | $411.4^a$ | 3.901 | 0.015 |
| D.I. (g/rat/day) | 113.1 | 102.5 | 105.5 | 107.9 | 2.808 | 0.238 |
| Week 2 | | | | | | |
| BM (g) | $391.7^b$ | $416.7^a$ | $419.8^a$ | $416.4^a$ | 4.004 | 0.017 |
| D.I | $117.8^a$ | $94.9^b$ | $96.8^b$ | $96.2^b$ | 2.087 | 0.000 |
| Week 3 | | | | | | |
| BM | $400.2^b$ | $425.0^a$ | $429.5^a$ | $424.6^a$ | 4.160 | 0.018 |
| D.I. (g/rat/day) | $122.6^a$ | $96.6^b$ | $100.1^b$ | $98.6^b$ | 2.183 | 0.000 |
| Week 4 | | | | | | |
| BM (g) | $408.6^b$ | $437.7^a$ | $438.2^a$ | $434.1^a$ | 4.463 | 0.024 |
| D.I. (g/rat/day) | $125.9^a$ | $104.0^b$ | $97.3^b$ | $98.2^b$ | 2.392 | 0.000 |
| Week 5 | | | | | | |
| BM (g) | $413.1^b$ | $444.9^a$ | $445.4^a$ | $440.1^a$ | 4.738 | 0.019 |
| D.I. (g/rat/day) | $130.3^a$ | $105.1^b$ | $101.5^b$ | $101.6^b$ | 2.377 | 0.000 |
| Week 6 | | | | | | |
| BM (g) | $418.4^b$ | $454.2^a$ | $453.1^a$ | $447.6^a$ | 4.924 | 0.013 |
| D.I. (g/rat/day) | $121.1^a$ | $100.7^b$ | $97.8^b$ | $97.1^b$ | 2.180 | 0.000 |
| Week 7 | | | | | | |
| BM (g) | $420.2^a$ | $458.8^b$ | $457.2^a$ | $451.7^a$ | 4.974 | 0.007 |
| D.I. (g/rat/day) | $118.4^a$ | $99.8^b$ | $95.6^b$ | $98.3^b$ | 1.862 | 0.000 |
| Week 8 | | | | | | |
| BM (g) | $423.7^a$ | $466.8^b$ | $461.6^a$ | $457.0^a$ | 5.037 | 0.002 |
| D.I. (g/rat/day) | $118.9^a$ | $100.3^b$ | $94.0^b$ | $95.6^b$ | 1.993 | 0.000 |
| Week 9 | | | | | | |
| BM (g) | $429.6^b$ | $474.8^a$ | $469.7^a$ | $464.6^a$ | 5.172 | 0.001 |
| D.I. (g/rat/day) | $123.6^a$ | $101.1^b$ | $97.8^b$ | $100.7^b$ | 2.278 | 0.000 |
| Dietary intake, days 64-66 | $53.9^a$ | $44.3^b$ | $41.2^b$ | $42.7^b$ | 1.031 | 0.000 |
| Intake, days 1-66 | $1146^a$ | $949^b$ | $927^b$ | $937^b$ | 17.801 | 0.000 |

[a]SEM: standard error of the mean, SD for all rats divided by the square root of the total number of rats, n = 40.
[b]Means with different superscript index letters within the same rows are different at P ≤ 0.05.

The animals were deprived of food 10-12 hours before the conclusion of the experiment. On the day the experiment ended, animals were sacrificed by an intraperitoneal injection of a mixture of xylazine and ketamine, in line with the institutional procedures of the DBFoF and appropriate recommendations on laboratory animals. Blood samples were collected from the caudal caval vein into heparinized tubes. Heparinized blood was centrifuged (350× g, 10 min, 4° C.), and plasma was separated and stored at −20° C. until the analyses. Colorimetric methods were used to determine the levels of glucose (GL). Statistical analysis was performed as described in Example 3.

Figure 11:
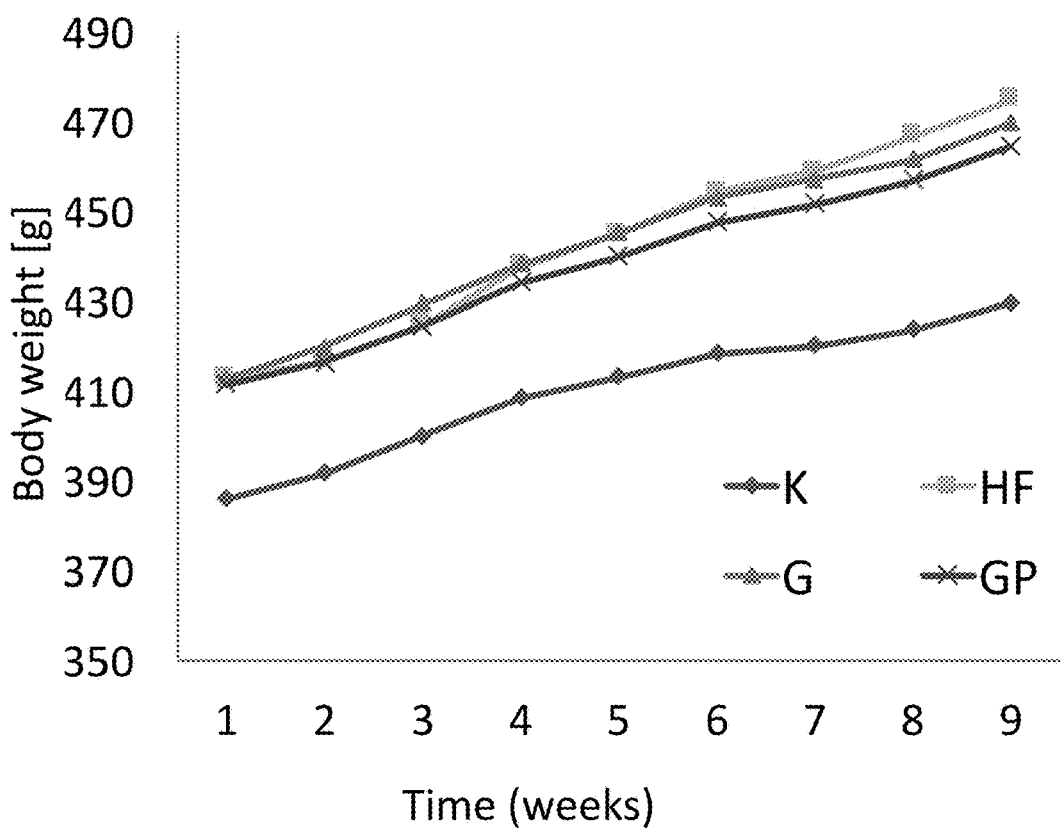
FIG. 11 presents rat body mass during in groups fed on high-fat diet (HF), high fat diet supplemented with fibers (G), and high fat diet supplemented with fibers and plant extract combination no. I (GP).

As indicated by the data presented in Table 6, and in FIG. 11, among the high-fat groups, the highest final body mass was observed in group HF (464.6 g), namely, the group having a diet devoid of plant extracts or fiber supplements.

Figure 12:
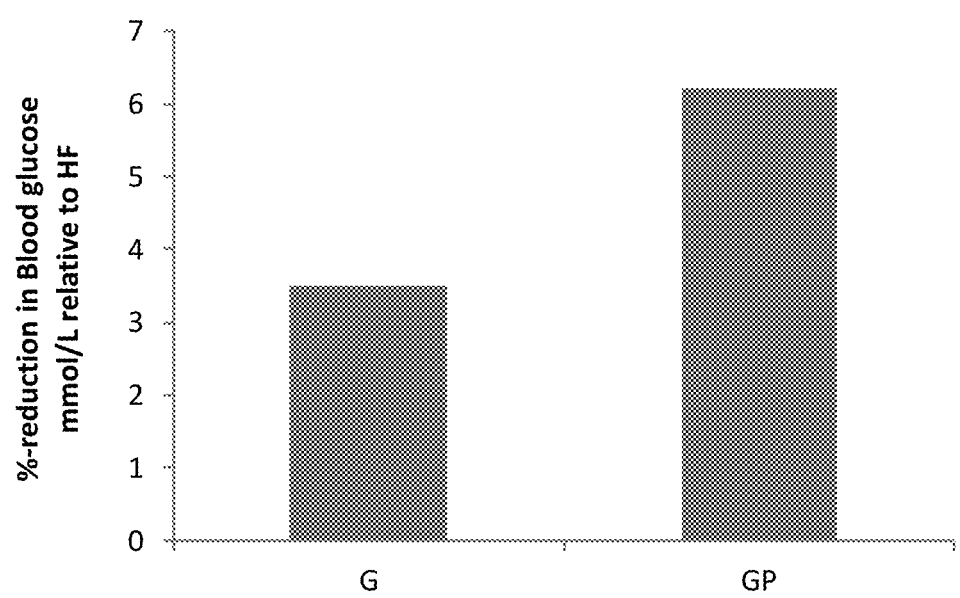
FIG. 12 presents reduction in blood glucose level in rats fed on high fat diet supplemented with fiber (G), or with a combination of fiber and plant extract combination no. I (GP), relative to rats fed on high-fat diet devoid of supplements.

Furthermore, as shown in FIG. 12, rats receiving high fat diet supplemented with dietary fibers have a 3.5% reduction in blood glucose levels. Surprisingly, by supplementing the high-fat diet with both dietary fibers and plant extracts, the reduction in the blood glucose levels reached 6.5%.

Example 5: Plant Extract Combinations that do not Reduce Blood Glucose Levels

A comparative experiment, testing the relative effect of different plant extract combinations, was performed on 120 male Wistar rats having mean body weight of 329.7±26.5 g, bred at IRZiBZ PAN in Olsztyn. Each study group consisted of 10 rats. Rats were kept in individual cages in a ventilated at a constant temperature of about 22° C., controlled relative humidity of about 60% and appropriate lighting (day/night, 12/12 hours). During the experimental period, rats were fed the standard laboratory rodent mix. Rats were deprived of food 12 hours prior to the first measurement of blood glucose levels, while constant access to water was maintained. On the day of the experiment, rats were weighed and fasting blood glucose measurements were taken, via a scalpel incision at the tip of the tail. Next, rats were administered water (negative control), or aqueous solutions of pre-defined combinations of plant extracts, as follows:

combination I: white mulberry extract (120 mg per 1 kg body weight)+ bean extract (100 mg per 1 kg body weight)+ green coffee extract (20 mg per 1 kg body weight).

combination IV: white mulberry extract (120 mg per 1 kg body weight)+ green coffee extract (20 mg per 1 kg body weight).

combination V: green coffee extract (20 mg per 1 kg body weight)+ bitter melon extract (150 mg per 1 kg body weight).

combination VI: green coffee extract (20 mg per 1 kg body weight)+ bitter melon extract (150 mg per 1 kg body weight)+ bean extract (100 mg per 1 kg body weight).

combination VII: green coffee extract (20 mg per 1 kg body weight)+ bitter melon extract (150 mg per 1 kg body weight)+ pomelo extract (100 mg per 1 kg body weight).

The solutions of the extracts were prepared so that the amount of liquid administered to an animal weighing 350 g was 1 mL. Water was administered to the control group in a similar manner. Five minutes after administration of the extracts each rat intragastrically received 50% aqueous solution of sucrose in the amount of 2 g/kg body weight (A) or 40% starch solution in the amount of 2 g/kg body weight (B). Subsequent blood glucose levels measurements were taken after 15, 30, 60, 90, 120 and 180 minutes (counting from administration of the sucrose/starch solution) using Accu-Chek Go (Roche Diagnostics GmbH, Mannheim, Germany) glucometer and test strips.

Statistical analysis using Student's t-test was performed for proper interpretation of results. Each result obtained for a particular product was compared to the analogous result obtained in the negative control (water) group. Results are presented in Table 7, below and in FIGS. 13A-13B.

extracts (such as combination IV including white mulberry extract and green coffee extract (squares) and combination V including green coffee extract and bitter melon extract (cross). Furthermore, the results clearly show that not all combinations of three plant extracts provide optimal results. In fact, combination I caused a significantly advantageous reduction in the measured blood glucose levels when compared to alternative combinations of three plant extracts (such as combination VI including white mulberry extract, green coffee extract and bitter melon (asterisk) and combination VII including green coffee extract, bitter melon extract and pomelo extract (circles)).

Figure 14A:
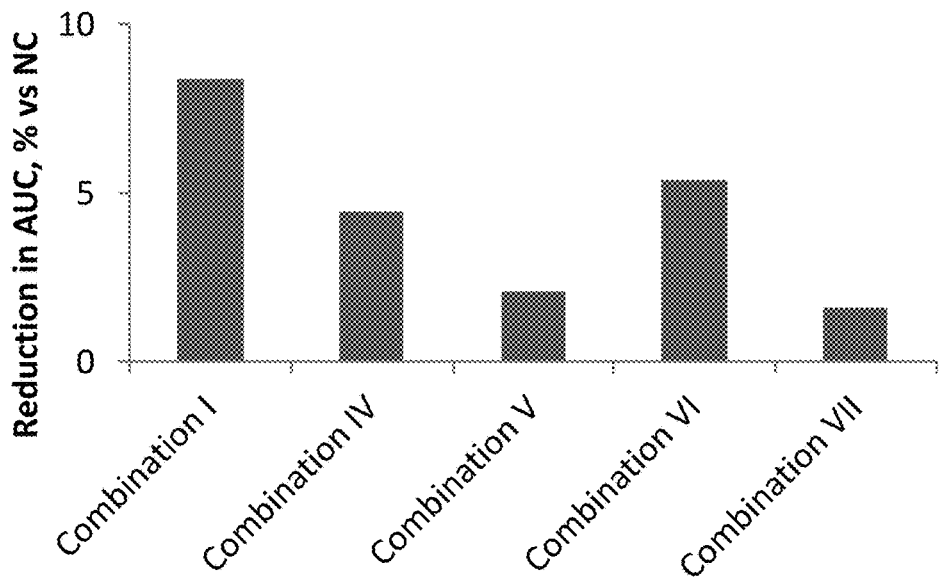
FIG. 14 shows blood glucose levels (AUC) exerted by plant extract combinations no. I and IV-VII relative to negative control (water; 100%) in rats fed on 50% sucrose (A) or starch (B).
Figure 14B:
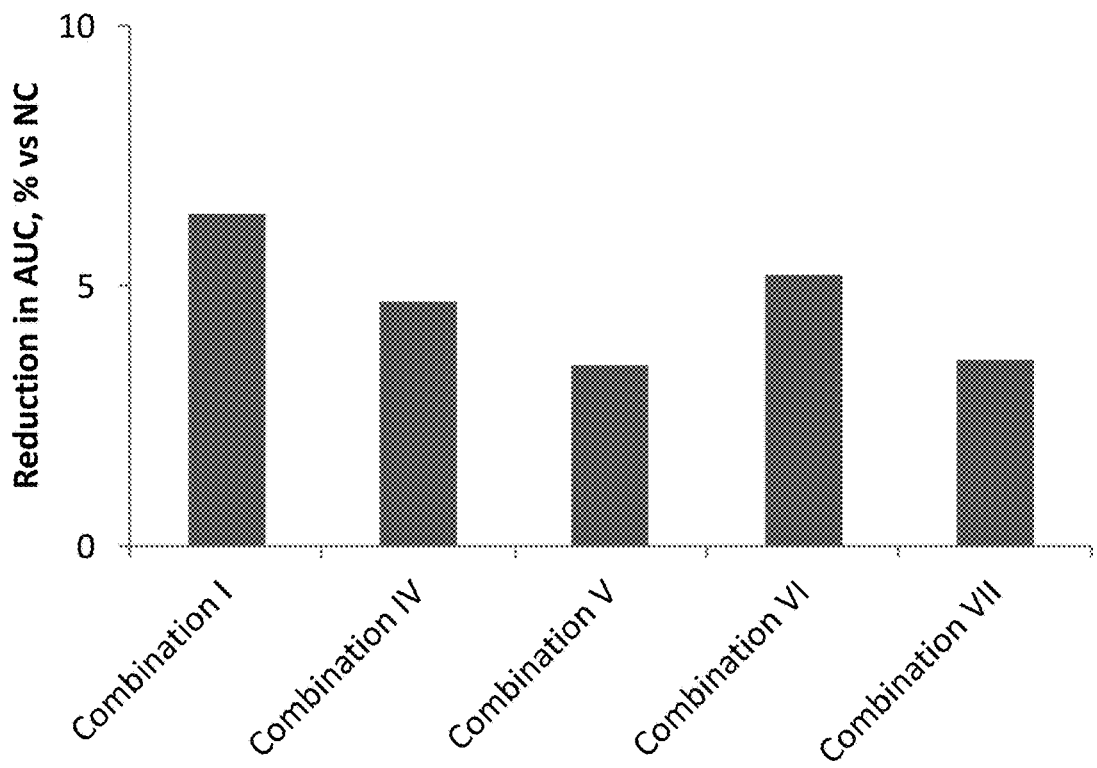

Furthermore, overall reduction in blood glucose levels during the entire test, represented by %-reduction in the area under the curve (AUC) as compared to control (water), is significantly better when combinations I is administered to rats fed on 50% sucrose (FIG. 14A) or 40% starch (FIG. 14B) as compared to combinations IV-VII.

Example 6: The Effect of Individual Extracts/Fibers on Blood Glucose—Clinical Studies The effects of white mulberry extract, white kidney bean extract, green coffee extract, insulin, glucomannan and thylakoids in different amounts on human blood glucose levels were tested in an experiment conducted with 64 volunteers with BMI at 22.99 29.99 kg/m$^2$. Each study group consisted of 16 healthy subjects. During the experimental period, the subjects were administered a study test product according to the composition and doses mentioned in each substudy, as detailed below, and 15 minutes later the subject received a meal consisting of 100 g (substudy 1) or 150 g (substudies 2-4) wheat bread. In substudy 1, blood was drawn intravenously 15, 30, 45, 60, 75, 90 and 120 minutes after the beginning of the study meal, whereas in substudies

TABLE 7

The effect of plant extract combinations on blood glucose in rats

| Time (min) | 0 | 15 | 30 | 60 | 90 | 120 | 180 |
|---|---|---|---|---|---|---|---|
| SUCROSE | | | | | | | |
| Water | 90.1 ± 3.41 | 155.7 ± 8.19 | 142.0 ± 9.12 | 133.6 ± 6.72 | 128.0 ± 4.76 | 121.3 ± 3.83 | 110.3 ± 3.8 |
| Comb. I | 90.9 ± 1.66 | 125.4 ± 6.47 | 128.1 ± 3.7 | 117.3 ± 5.93 | 117.2 ± 4.78 | 114.2 ± 6.44 | 109.8 ± 5.2 |
| Comb. IV | 89.0 ± 3.65 | 138.9 ± 7.29 | 129.4 ± 3.37 | 128.9 ± 8.67 | 123.6 ± 6.59 | 117.2 ± 4.57 | 110.4 ± 3.3 |
| Comb. V | 89.3 ± 4.76 | 142.5 ± 10.0 | 131.7 ± 6.82 | 130.3 ± 2.45 | 126.6 ± 5.23 | 122.8 ± 5.71 | 111.4 ± 3.0 |
| Comb. VI | 89.5 ± 2.84 | 132.8 ± 15.2 | 127.5 ± 5.87 | 127.8 ± 5.51 | 123.6 ± 3.86 | 117.1 ± 6.44 | 108.1 ± 4.4 |
| Comb. VII | 90.1 ± 3.28 | 145.5 ± 8.11 | 137.3 ± 11.5 | 130.0 ± 8.16 | 125.3 ± 7.21 | 122.1 ± 4.12 | 111.4 ± 4.2 |
| STARCH | | | | | | | |
| Water | 90.5 ± 4.20 | 122.3 ± 3.92 | 123.4 ± 4.35 | 117.9 ± 2.81 | 115.6 ± 3.53 | 111.1 ± 4.51 | 102.5 ± 4.4 |
| Comb. I | 90.4 ± 3.75 | 119.6 ± 3.06 | 118.4 ± 4.97 | 110.4 ± 5.78 | 107.4 ± 3.69 | 102.0 ± 4.94 | 93.1 ± 3.96 |
| Comb. IV | 88.8 ± 4.64 | 118.5 ± 6.67 | 123.7 ± 6.09 | 112.8 ± 5.79 | 110.4 ± 7.65 | 102.2 ± 6.65 | 96.2 ± 4.92 |
| Comb. V | 89.2 ± 2.82 | 118.7 ± 5.85 | 119.6 ± 6.96 | 114.7 ± 7.01 | 109.6 ± 9.08 | 105.9 ± 8.52 | 100.5 ± 8.7 |
| Comb. VI | 88.9 ± 5.59 | 118.5 ± 18.9 | 122.6 ± 13.1 | 114.0 ± 9.50 | 107.5 ± 7.92 | 101.4 ± 5.42 | 96.3 ± 7.15 |
| Comb. VII | 91.1 ± 2.73 | 121.7 ± 10.3 | 121.5 ± 9.22 | 115.1 ± 7.98 | 108.7 ± 6.80 | 106.5 ± 8.59 | 96.0 ± 6.62 |

Fasting blood glucose levels in all groups of rats subjected to the test ranged between 89.0 to 90.9 mg/dL.

Figure 13A:
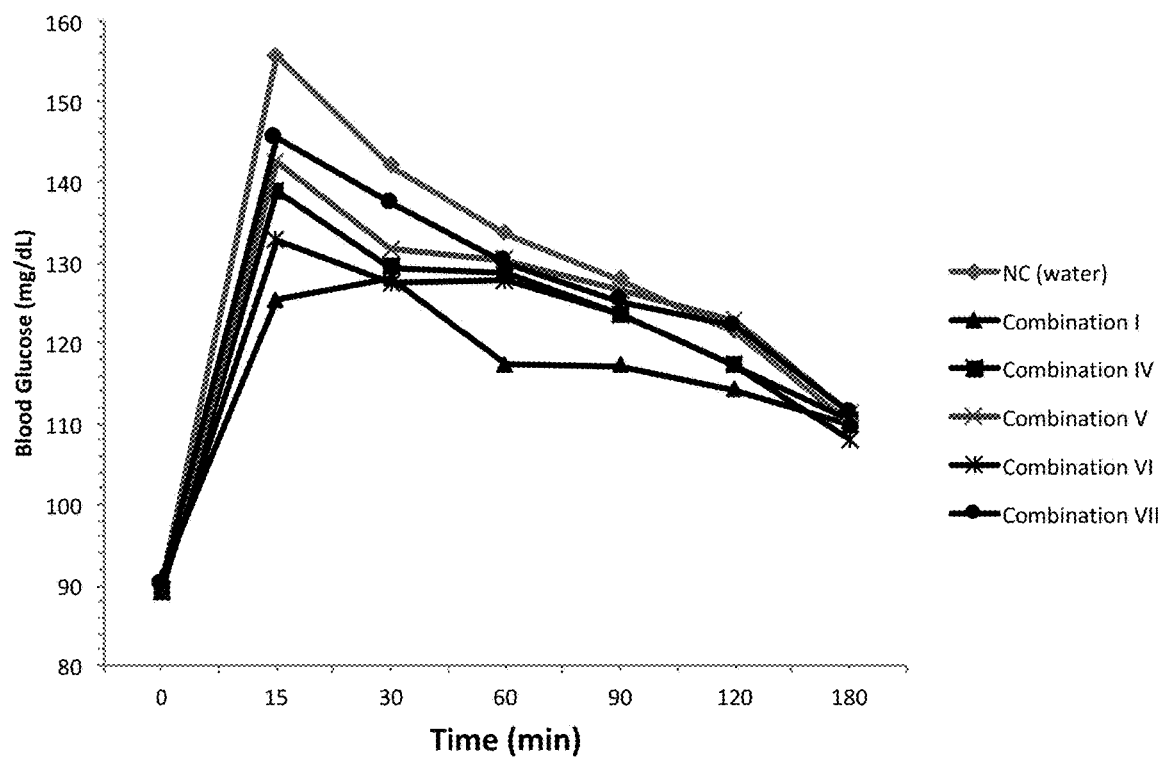
FIG. 13 exhibits glucose tolerance test following administration of a 50% sucrose solution (A) or 40% starch solution (B), in rats receiving plant extract combination I, combination IV, combination V, combination VI, combination VII and water as a negative control.
Figure 13B:
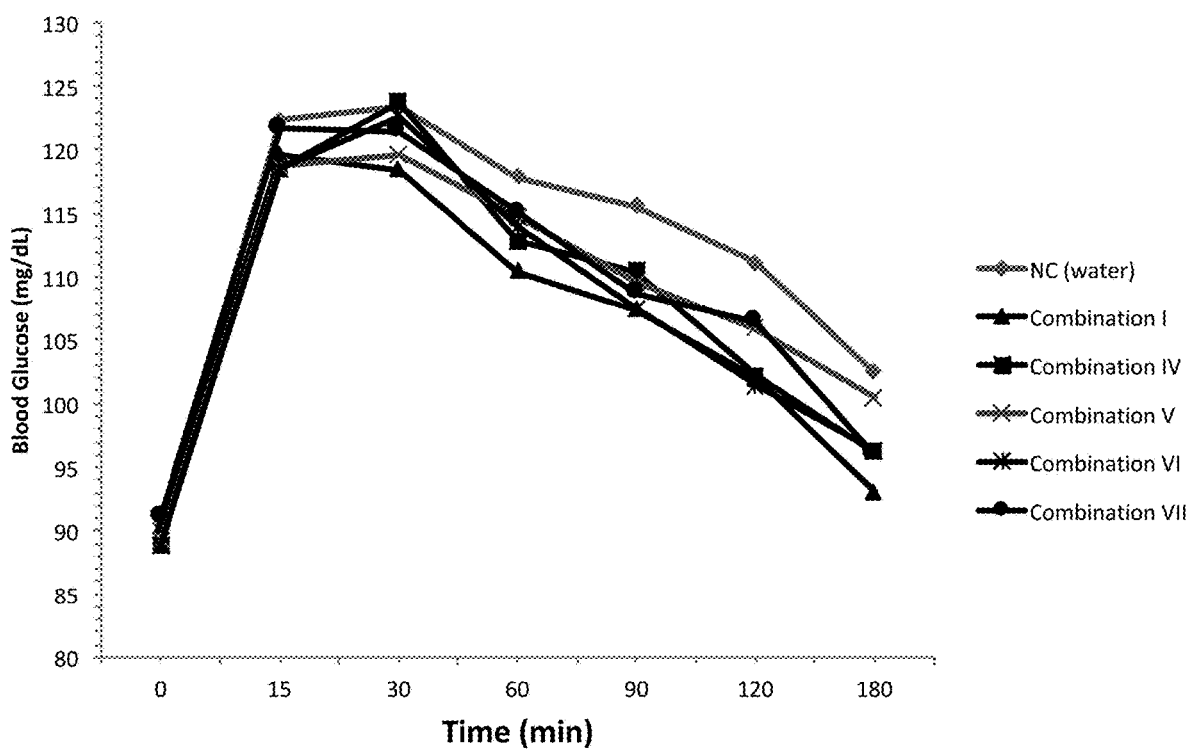

As shown in FIGS. 13A and 13B, administration of plant extracts combination I (triangles) resulted in a significantly milder surge in blood glucose levels, as also shown in example 2. Although combinations IV-VII also reduced the surge in blood glucose levels, the reduction was much less pronounced compared to combination I. This clearly shows that combination I including white mulberry extract, bean extract and green coffee extract is more efficient in reducing blood glucose than combinations including only two plant 2-4 bread consumption time was extended by 5 minutes and blood was drawn 20, 35, 50, 65, 80, 95 and 125 minutes after the beginning of the study meal and glucose levels were measured.

Substudies 1-3 tested the effects of high, middle and low doses (respectively) of white mulberry extract, white kidney bean extract and green coffee extract separately on postprandial blood glucose and insulin levels. Sub study 4 tested the effects of insulin+glucomannan, insulin alone and thylakoids separately on postprandial blood glucose and insulin levels.

SUBSTUDY 1—High Doses of Extracts

Products: I-white mulberry extract (600 mg), II-white kidney bean extract (2,000 mg), III-green coffee extract (800 mg), IV-placebo.

In order to detect significant differences in glucose and insulin levels between groups of patients receiving particular preparations (I-IV) the following methods were applied: adaptation of the variance analysis model by making a linear model for each of the groups (approach P1), and Kruskal-Wallis non-parametric test (approach P2). Which approach was selected depended on fulfillment of the following conditions: (1) consistency of the variable's distribution with the normal distribution in both analyzed groups (Shapiro-Wilk test), (2) homoscedasticity (Levene's test). If at least one of the conditions was not fulfilled, approach P2 was selected. In other cases approach P1 was selected. Apart from the variables describing levels at particular minutes from the beginning of the test, percentage changes of levels (compared to fasting state) and areas under curves (AUC) were also measured. AUC was determined using the trapezoidal rule. If the conducted test was significant (p-value<0.05) post-hoc analysis was carried out. Similarly to the first phase of the analysis, if conditions (1) and (2) were fulfilled, the t-test was carried out comparing both groups and if at least one of these conditions was not fulfilled, the non-parametric Wilcoxon's rank sum test was carried out. Statistical significance was set at alpha=0.05. In order to compare the levels at specific minutes between two selected substudies, the t-test or the Wilcoxon's rank sum test were used, at presuppositions described above. All calculations were made using the R programming environment.

Figure 15A:
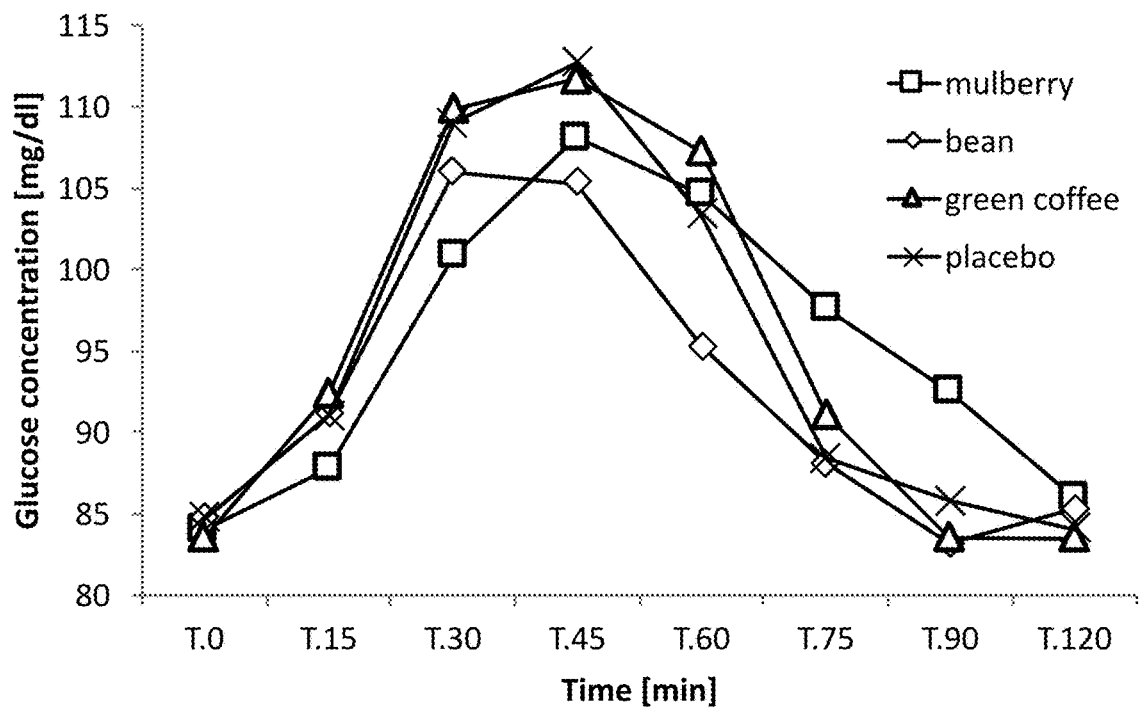
FIGS. 15A-15D show blood glucose concentrations in healthy subjects following a meal preceded with consumption of individual extracts of: white mulberry extract (600 mg), white kidney bean extract (2,000 mg), green coffee extract (800 mg) and placebo (15A); white mulberry extract (400 mg), white kidney bean extract (1,200 mg), green coffee extract (400 mg) and placebo (15B); white mulberry extract (200 mg), white kidney bean extract (800 mg), green coffee extract (200 mg) and placebo (15C); and insulin+glucomannan (2+3 g), insulin (5 g), thylakoids (200 mg), and placebo (15D).

A tendency towards lower glucose levels (p=0.07) after taking mulberry product I, compared to control IV, was observed at minute 30 of the test (100.9±2.5 vs. 109.0±3.3 mg/dL, respectively). At minute 75 of the test an opposite tendency (p=0.09) was observed, (97.6±4.3 vs. 88.4±5.1 mg/dL for I and IV products respectively), which at minute 90 of the test reached statistical significance (p=0.04, 92.6±2.8 vs. 85.8±4.6 mg/dL for I and IV respectively). Analysis of percentage changes of blood glucose levels showed a tendency towards lower increase of glucose levels after taking product I vs. placebo IV at minute 15: 104.5±1.7 (product I) vs. 107.6±1.8 mg/dL (placebo IV), p=0.12; and at minute 30: 120.2±2.8 (product I) vs. 128.6±3.4 mg/dL (placebo IV), p=0.07. In later stages of the test, the percentage increase of glucose levels was higher after taking product I vs. control IV: 116.1±4.5 vs. 104.3±5.8 mg/dL respectively (p=0.06, min. 80) and 110.3±3.0 vs. 101.2±5.2 mg/dL respectively (p=0.03, min. 95). This proves that the intended effect of delayed carbohydrate absorption was achieved. There were no significant differences found either in glucose levels, changes in glucose levels or AUC of glucose levels after taking the products II and III vs. placebo IV. There were no statistically significant differences found in insulin levels in this substudy (FIG. 15A)

SUBSTUDY 2—Middle Doses of Extracts

Products: V-white mulberry extract (400 mg), VI-white kidney bean extract (1,200 mg), VII-green coffee extract (400 mg), VIII-placebo A tendency (p=0.10) towards less increase in glucose level was observed at minute 20 after taking mulberry V vs. control VIII-109.1±2.2 vs. 116.1±2.8 mg/dL, respectively. A significant reduction of blood glucose levels was witnessed upon taking product VII (green coffee extract), compared to control: at minute 80 of the test, glucose levels were 77.6±3.2 (product VII) vs. 94.0±4.3 mg/dL (placebo VIII), p=0.007, and at minute 95 of the test, glucose levels were 81.2±3.2 (product VII) vs. 91.8±3.8 mg/dL (placebo VIII), p=0.04.

Figure 15B:
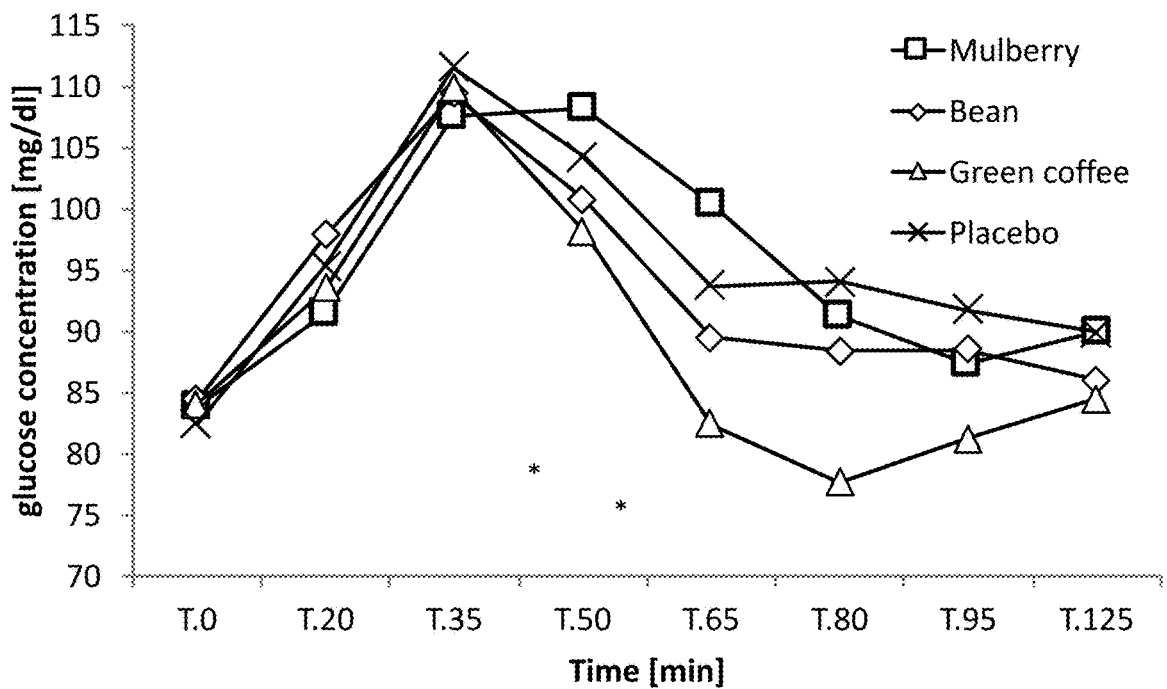

Analysis of percentage changes in levels showed that after taking product VII the increase of glucose levels is significantly lower compared to control. A tendency towards lower increase of glucose levels after taking coffee extract VII vs. control was observed as early as at minute 50 of the test: 116.7±4.1 (product VII) vs. 126.4±4.8% (placebo VIII), (p=0.12). After 65, 80 and 95 minutes, the differences were statistically significant and amounted to: 98.1±4.6 (VII) vs. 113.8±5.9% (VIII) (p=0.03, 65 min.); 92.7±4.0 (VII) vs. 114.2±5.0% (VIII) (p=0.002, 80 min.); and 96.8±3.6 (VII) vs. 111.2±3.8% (VIII) (p=0.01, 95 min.). This tendency (p=0.095) remained unchanged also at minute 125 of the test (100.6±3.3 vs. 109.1±3.3% for VII and VIII respectively). Also, a tendency (p=0.08) towards lower AUC of glucose levels was observed: 11089±325 vs. 11956±365 mg*min/dL, for coffee extract VII and placebo VIII respectively. Moreover, significantly lower (p=0.01) AUC for percentage changes in glucose levels were observed after taking product VII vs. placebo VIII (11091±303 vs. 12355±370, respectively) (FIG. 15B).

Further, a tendency (p=0.15) towards lower AUC for percentage changes in glucose levels was witnessed after taking bean extract VI vs. control, which amounted to 11726±447 vs. 12355±370, respectively. This, despite no significant differences in particular time points, percentage changes in glucose levels or AUC of glucose levels. There were no significant differences or tendencies observed for other analyzed parameters including insulin levels.

SUBSTUDY 3—Low Doses of Extracts

Products: IX-white mulberry extract (200 mg), X-white kidney bean extract (800 mg), XI-green coffee extract (200 mg), XII-placebo.

Figure 15C:
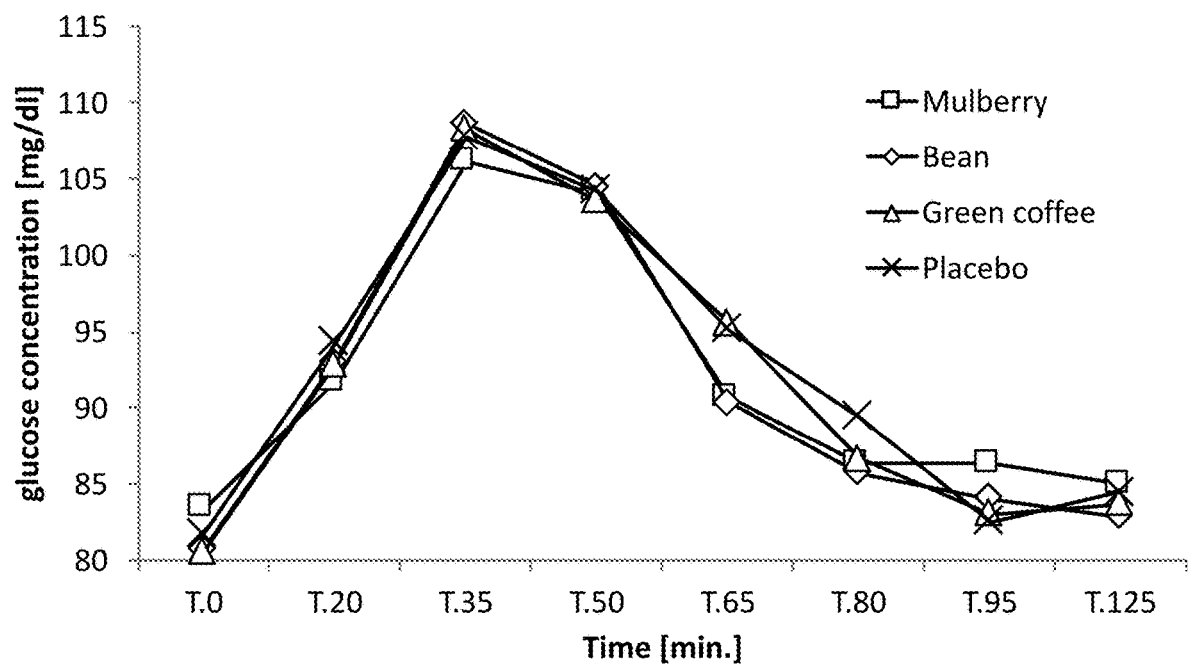

There were no significant differences observed between the analyzed parameters relating to blood glucose levels (FIG. 15C). However, substudy 3 was the only one in which a tendency (p=0.15) towards lower insulin levels was observed, as exemplified in minute 125 after taking product XI vs. placebo XII (31.0±3.3 vs. 39.7±4.2 IU/ml, respectively). Analysis of percentage changes in levels also showed a tendency (p=0.09) towards lower increase in insulin levels after taking product XI vs. placebo XII (279.8±22.7 vs. 358.6±33.3%, respectively). Moreover, a tendency (p=0.14) towards lower value of AUC of insulin levels was observed after taking product XI vs. placebo XII.

SUBSTUDY 4—Products: XIII-Insulin+Glucomannan (2+3 g), XIV-insulin (5 g), XV-thylakoids (200 mg), XVI-placebo.

Figure 15D:
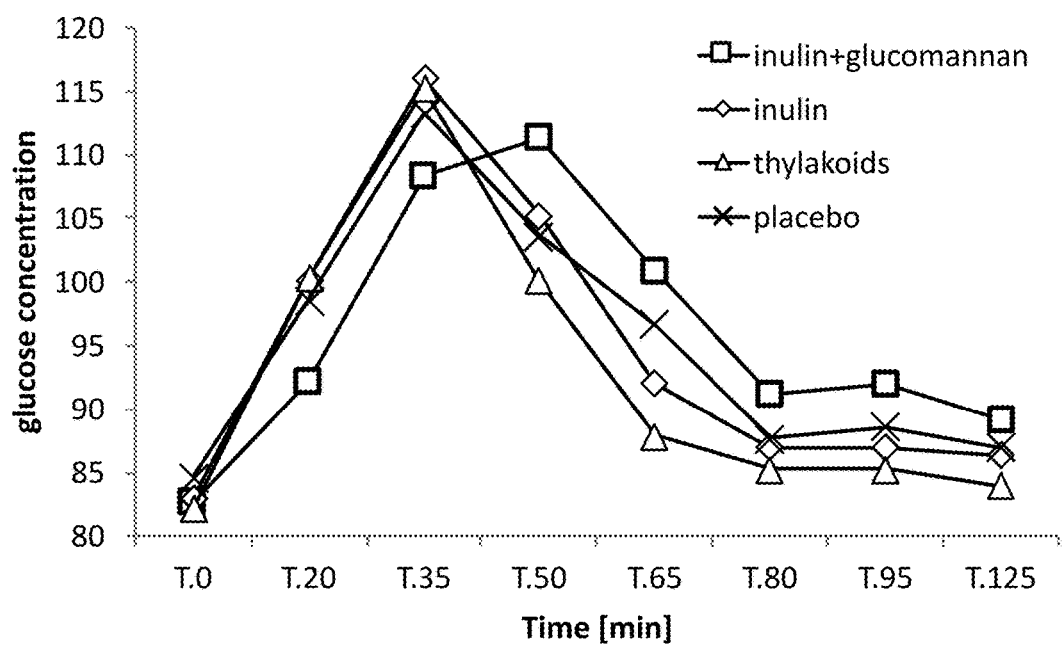

A tendency (p=0.06) towards lower glucose levels after taking product XIII (insulin+glucomannan) vs. XVI (placebo) was observed at minute 20 of the test (92.2±2.8 vs. 98.6±2.5 mg/dL, respectively). At minute 65 of the test after taking product XV (thylakoids) a tendency (p=0.12) towards lower glucose levels vs. placebo (87.9±3.4 vs. 96.7±3.7 mg/dL, respectively) was also witnessed (FIG. 15D). No significant differences or tendencies were observed for other analyzed parameters including levels of insulin.

The conducted tests presented in substudies 1-4 and analyses thereof indicate that the investigated test products affect postprandial glucose levels in sera of healthy subjects. The white mulberry extract at a dose of 600 mg (substudy 1, product I) is associated with lower glucose level and lower increase of glucose level during the first 15-30 minutes after food intake. Carbohydrate absorption seems to be delayed, thus resulting in a significant increase of glucose level within 75-90 minutes after intake of a meal. Therefore, using just white mulberry extract may not show any effect on the decrease of the glycemic index of the food during the entire 120-minute-long postprandial period.

No significant differences were observed at various time points after administrations of white kidney bean extracts (phaseolamin) alone. However, when administered at a dose of 1,200 mg (substudy 2, product VI), a trend towards lower AUC of glucose levels was observed.

The lowest doses of the aforementioned individual extracts (applied in substudy 3) did not seem to exert any effect on postprandial glucose level in healthy people.

Analysis of the results obtained in substudy 4 showed a tendency towards lower glucose levels at minute 20 after taking the insulin+glucomannan preparation (XIII) and at minute 65 after taking thylakoids (XV) at the doses applied.

The above tests exhibit non-sufficient reduction in AUC values of glucose levels throughout the entire postprandial period (2 hours).

Example 7: The Effect of Extracts/Dietary Fibers on Human Blood Glucose Levels

The effects of two combinations of dietary fibers and/or extracts (substudies 5 and 6) on postprandial blood glucose and insulin level were tested based on the protocol described in Example 6, substudies 2-4, hereinabove. In substudy 5 the combination included white mulberry extract, white kidney bean extract and green coffee extract and in substudy 6 the combination includes the same extracts as in substudy 5, in combination with insulin and glucomannan.

SUBSTUDY 5—Products: XVII-white mulberry extract (600 mg)+ green coffee extract (400 mg)+ white kidney bean extract (1,200 mg), XVIII-placebo.

Figure 16A:
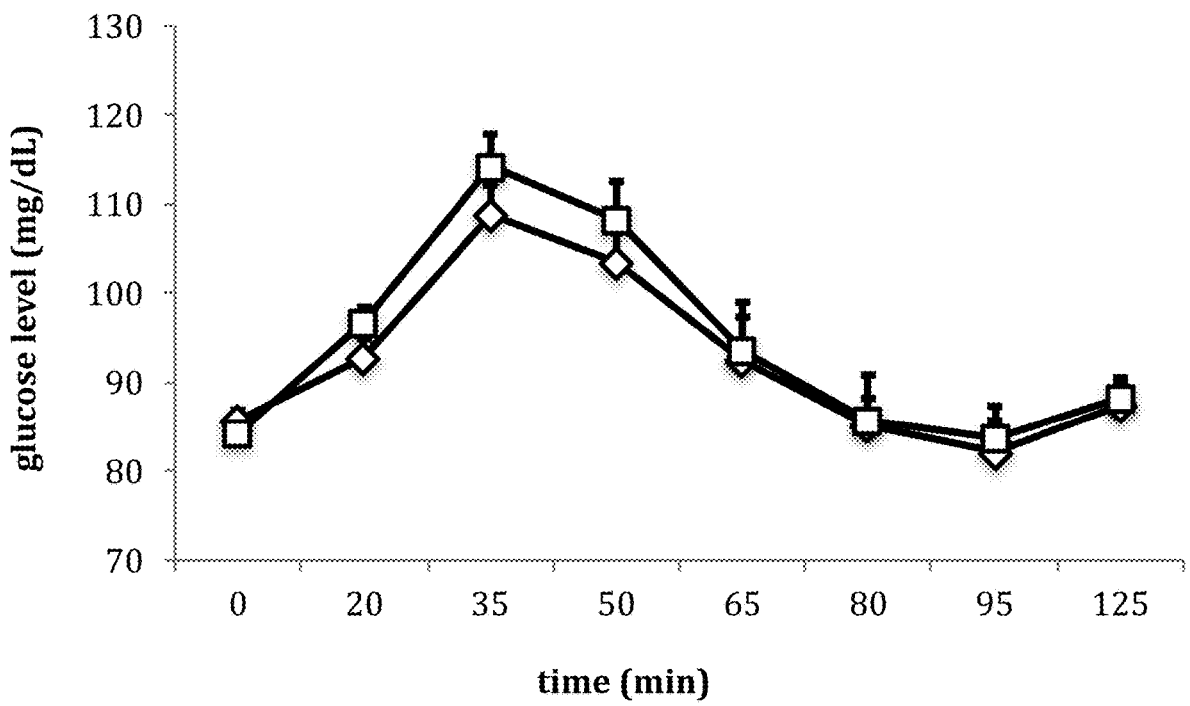
FIGS. 16A and 16B show blood glucose concentrations (16A) and insulin levels (16B) in healthy subjects following a meal preceded with consumption of a combination (diamonds) of white mulberry extract (600 mg), green coffee extract (400 mg) and white kidney bean extract (1,200 mg), or placebo (squares).

Glucose levels throughout the study are presented in FIG. 16A (diamonds: combination product XVII; squares—placebo product XVIII). Glucose levels at 20 and 35 minutes after meal upon ingestion of test preparation XVII were as follows: 92.8±1.8 (product XVII) vs. 96.6±2.1 mg/dL (placebo XVIII) (p=0.07, 20 min); and 108.8±3.6 (XVII) vs. 114.3±3.3 mg/dL (XVIII) (p=0.039, 35 min), indicating lower glucose levels at these time points. Furthermore, the percentage change in glucose levels was less pronounced after taking the test preparation XVII vs. control XVIII after 20 minutes of the study (108.4±1.6 vs. 114.6±2.0% for products XVII and XVIII respectively, p=0.005) and after 35 minutes of the study (126.9±3.7 vs. 135.7±4.0% for products XVII and XVIII respectively, p=0.005).

Figure 16B:
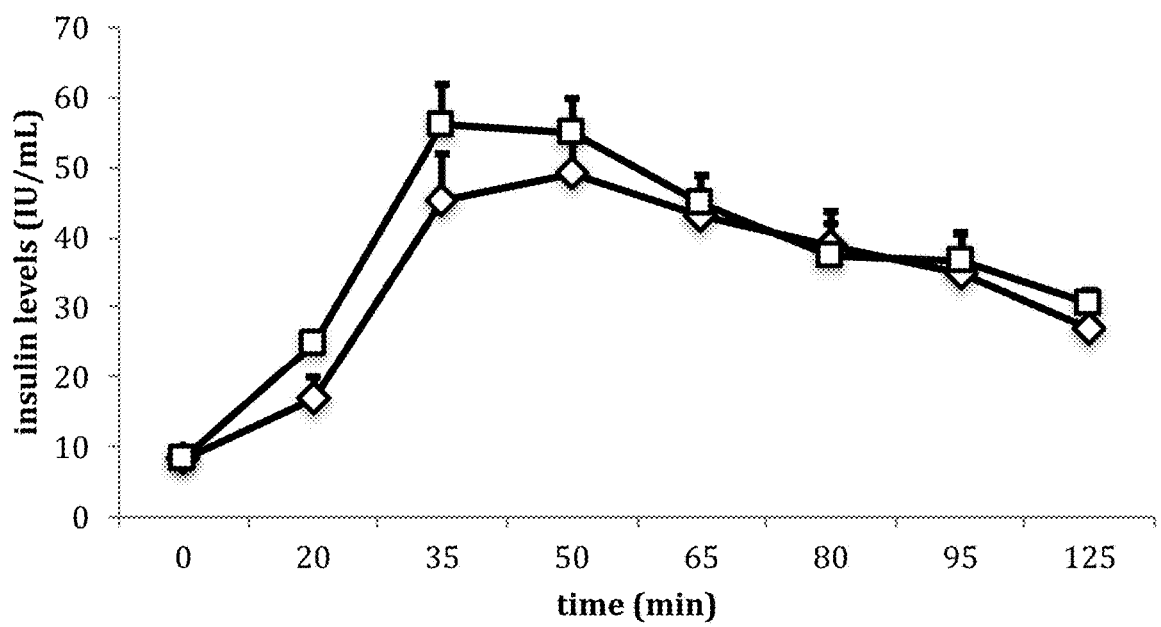

The corresponding insulin levels (FIG. 16B) were significantly lower 20 minutes after taking test preparation XVII and a trend towards lower insulin levels 35 minutes after a meal was also observed. After 20 minutes average insulin levels were 16.9±15 IU/mL following the ingestion of test preparation XVII, and 24.9±3.1 IU/mL following the ingestion of placebo XVIII. After 35 minutes, insulin levels were lower after taking the test preparation XVII vs. control XVIII and amounted to 45.1±5.7 vs. 56.1±6.8 IU/mL respectively (p=0.07). Furthermore, after 20 minutes of the study the percentage change in insulin levels was less pronounced after taking combination XVII vs. control XVIII (214.1±22.7 vs. 318.1±39.8% p=0.006). The trend remained unchanged after 35 minutes of the study (582.9±95.9 vs. 726.1±95.4% for combination XVII and placebo XVIII respectively, p=0.10). Average insulin levels and the percentage changes in insulin levels were not significantly different for the remaining experimental time points. The areas under the curves (AUC) of the insulin levels were not significantly different either.

SUBSTUDY 6—Products: XIX-white mulberry extract (600 mg)+ green coffee extract (400 mg)+ white kidney bean extract (1,200 mg)+ insulin (2000 mg)+ glucomannan (3000 mg), XX-placebo.

Figure 16C:
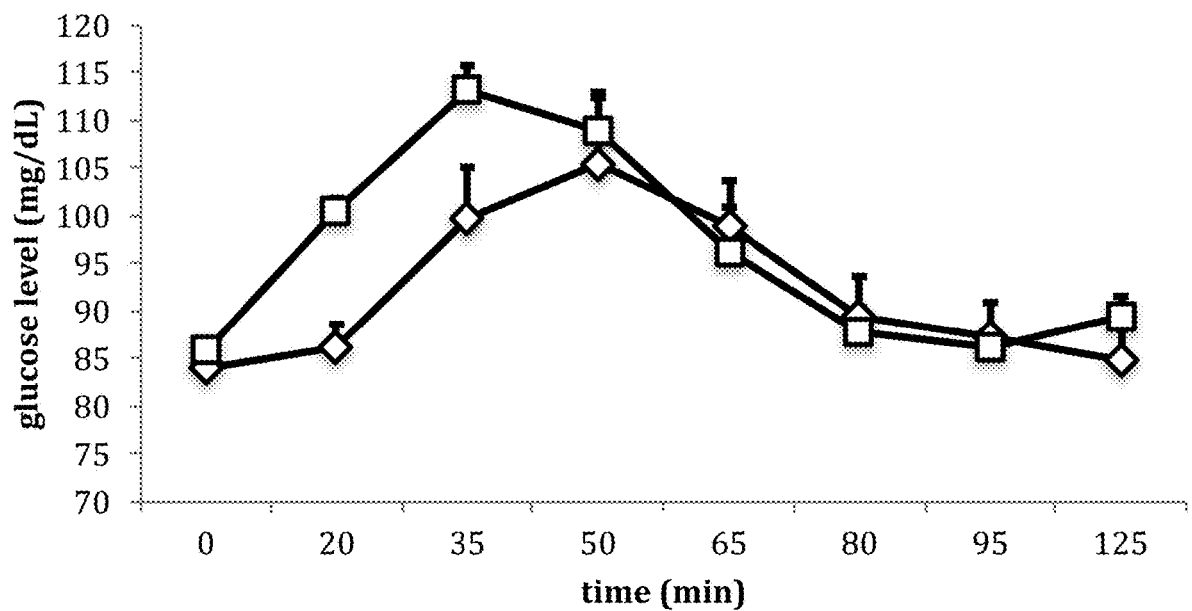
FIGS. 16C and 16D show blood glucose concentrations (16C) and insulin levels (16D) in healthy subjects following a meal preceded with consumption of a combination (diamonds) of white mulberry extract (600 mg), green coffee extract (400 mg), white kidney bean extract (1,200 mg) and glucomannan (3000 mg), or placebo (squares).

Glucose levels throughout the study are presented in FIG. 16C (diamonds: combination product XIX; squares—placebo product XX). As shown in FIG. 16C, the overall glucose level and the maximum glucose blood level where lower in subjects consuming the combination product. Specifically, average blood glucose levels after 20 minutes were 86.3±1.3 mg/dL following the ingestion of the test preparation XIX, and 100.6±2.3 mg/dL following the ingestion of the placebo XX (p=0.000005). At minute 35, average glucose levels amounted to 99.8±3.6 mg/dL vs. 113.2±3.3 mg/dL for product XIX and placebo XX respectively (p=0.01). Moreover, the percentage change in glucose levels was less pronounced after taking combination XIX vs. control (XX) after 20 minutes of the study (102.9±1.4 vs. 117.3±2.0%, for product XIX and placebo XX respectively, p=0.00001) and after 30 minutes of the study (119.2±3.5 vs. 131.5±5.1% for XIX and XX respectively, p=0.037).

Figure 16D:
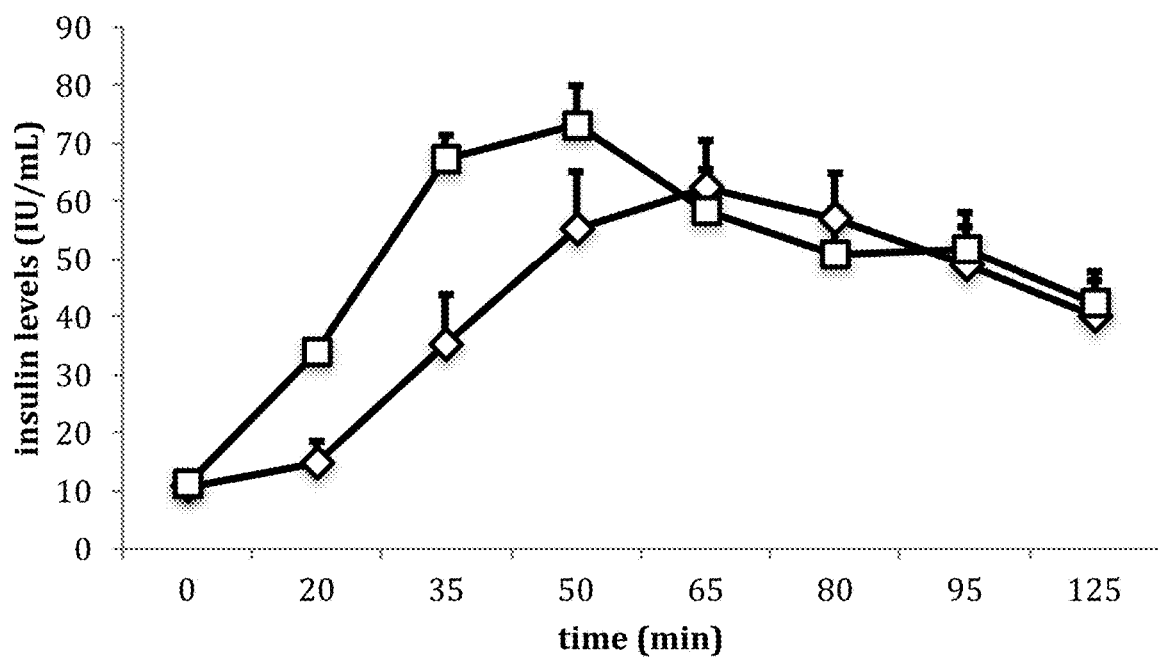

A similar trend was shown for the corresponding insulin levels (FIG. 16D). For example, significantly lower average insulin levels upon ingestion of test product XIX after 20 minutes (14.9±1.2 IU/mL) vs. placebo XX (34.1±3.7 IU/mL) (p=0.00001). After 35 minutes, average insulin levels were likewise significantly lower after taking test preparation XIX vs. control XX: 35.1±4.2 vs. 67.2±8.7 IU/mL respectively (p=0.0003). At min. 50 of the study a further strong trend towards lower insulin levels was witnessed after taking product XIX vs. control XX: 55.3±6.7 vs. 73.2±9.9 IU/mL respectively (p=0.05). The corresponding percentage changes were as follows: after 20 minutes—143.8±6.2 vs. 315.6±28.4% for XIX vs. control XX, respectively, (p=0.00001) and after 35 minutes—348.1±44.2 vs. 623.7±76.7% for XIX vs. control XX, respectively (p=0.00003). A substantially reduced average area under the curve (AUC) for the insulin levels after taking preparation XVII vs. XX was also observed: 5,213.4±575.6 vs. 6,258.7±747.8 respectively (p=0.02).

Substudies 5 and 6 were cross-examined in order to inspect the influence of test preparations XVII and XIX on blood glucose levels in different periods of the experiment. It was seen that 20 minutes after a meal the average glucose levels were lower when test product XIX (extracts+fiber) was taken compared to the levels after taking product XVII (extracts only): 86.1±1.5 vs. 92.7±2.1 mg/dL respectively (p=0.0057). After 35 minutes of the study the average glucose levels were again lower for test product XIX compared to test product XVII: 98.2±2.7 vs. 109.3±4.4 mg/dL, respectively (p=0.0088). The corresponding percentages for test product XIX vs. test product XVII were as follows: after 20 minutes: 102.6±1.7 vs. 109.1±1.8%, respectively (p=0.008); after 35 minutes: 117.3±3.7 vs. 128.5±4.4%, respectively (p=0.013).

Statistical analyses were also undertaken to compare preparations XVII and XIX and matching placebos in substudies 5 and 6.

After 20 minutes of the study a significantly smaller percentage increase in glucose levels related to the fasting values and compared to the placebo was observed after taking product XIX when compared to a decrease in the percentage increase of glucose levels after taking product XVII related to the placebo (−13.7±2.5 vs. −4.5±1.9, respectively, p=0.03).

After 95 minutes an opposite trend was observed (p=0.06): a smaller increase in the relative change (%) of glucose levels with respect to the fasting values (t=0), and compared to placebo, was recorded for test product XVII (−3.1±4.2), while test product XIX resulted in a greater increase (5.7±5.6). Such phenomenon could be attributed to the delay in carbohydrate absorption.

In summary, substudies 5 and 6 show that combinations XVII and XIX exhibit a potential to suppress an increase in glucose levels after meals in healthy subjects, especially within 20-35 minutes after a high glycemic index meal.

Substudies 5 and 6 were further cross-examined in order to inspect the influence of test combinations XVII and XIX on insulin levels in different periods of the experiment. It was found that both XVII and XIX exhibit the potential to suppress postprandial increase in insulin levels in healthy subjects, especially within 20-35 minutes after a high glycemic index meal. More favourable results were seen after taking test product XIX, in particular, 50 minutes after a meal. Also, the ingestion of test product XIX correlated with reduced AUC for the postprandial period compared to the control values.

Example 8: Comparison Between Combinations and Individual Components

The following substudies present a comparison between the results disclosed in Examples 6 and 7 above was conducted in order to determine the influence of individual products (Example 6) and combinations (Example 7) on blood glucose concentrations and insulin levels. The quantities of carbohydrates was elevated from 100 g to 150 g of wheat bread since the tested subjects were healthy (i.e. without carbohydrate metabolism disorders) and in order to emphasize the observed changes in blood glucose levels.

SUBSTUDY 7—Products: IV-placebo, XVIII-placebo.

Figure 17:
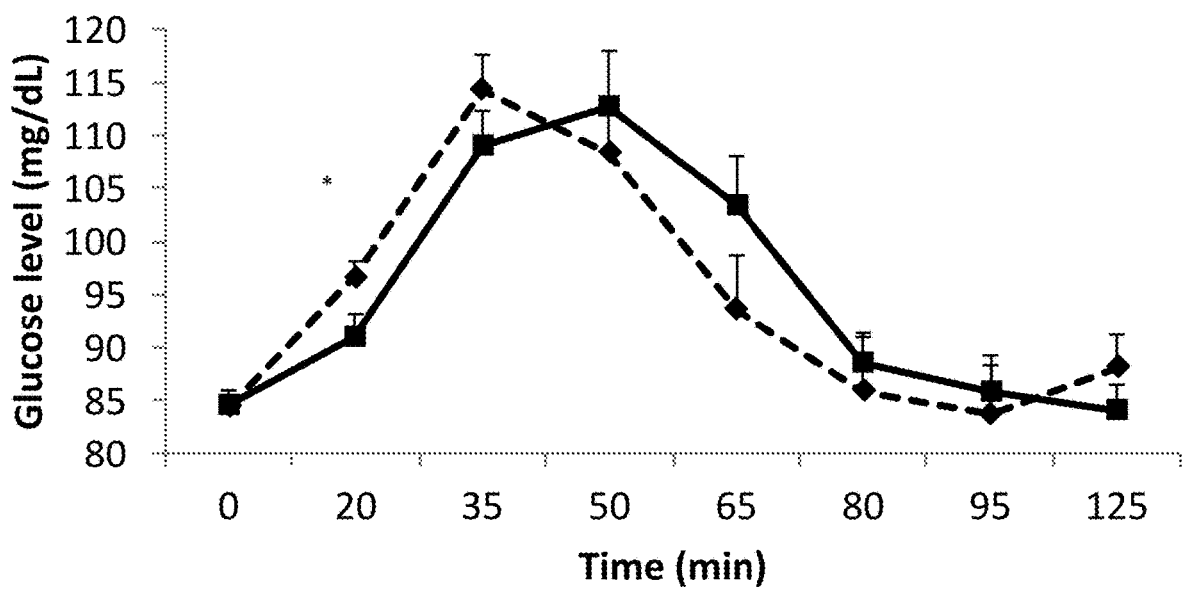
FIG. 17 shows blood glucose concentrations (mg/dL) in healthy subjects following consumption of placebo with 150 g bread (dashed line, diamonds) or 100 g bread (solid line, squares). *p<0.05; **p<0.01
Figure 18:
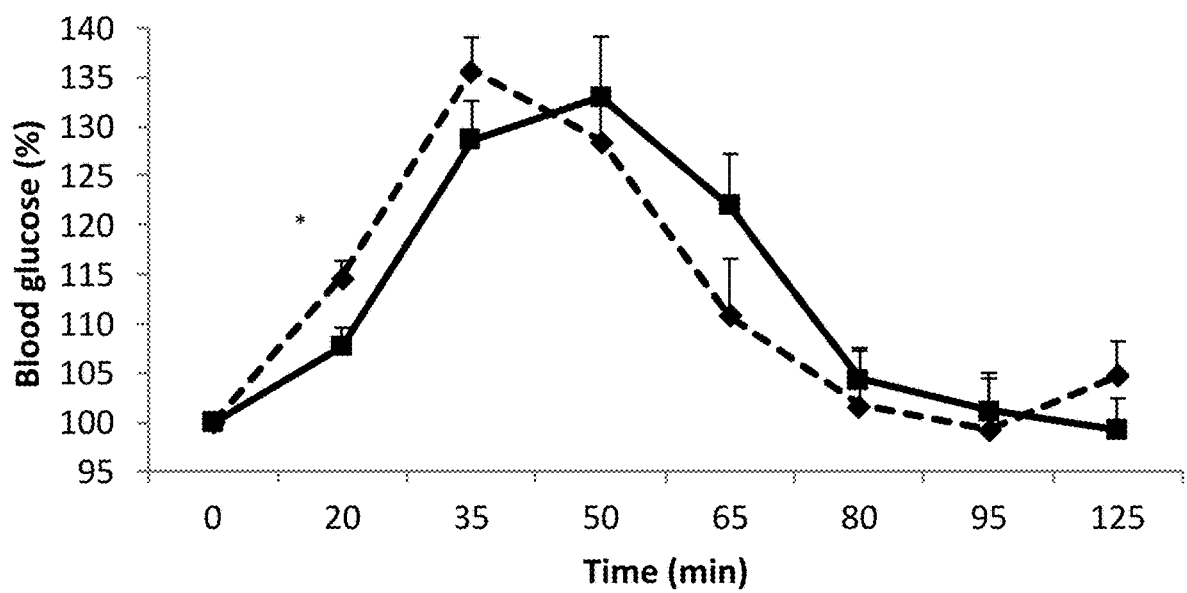
FIG. 18 shows the relative concentrations of blood glucose corresponding to FIG. 17.

Placebo products (IV and XVIII) were consumed with 100 g wheat bread or 150 g bread, respectively (FIG. 17). As expected, after 20 minutes of the study a significantly higher glucose level was observed after ingesting 150 g of bread (+ placebo XVIII) when compared to 100 g of bread (+ placebo IV) (96.6±2.1 and 91.0±1.5 mg/dL, respectively, p=0.04). Analysis of the percentage changes in glucose levels (FIG. 18) showed a corresponding increase in glucose levels 20 minutes after taking the 150 g bread meal (+ placebo XVIII) when compared to 100 g of bread (+ placebo IV) (114.6±2.0 vs. 107.6±1.8%, respectively, p=0.01).

SUBSTUDY 8—Products: IV-Placebo, XX-Placebo.

Placebo products (IV and XX) were consumed with 100 g wheat bread or 150 g bread, respectively (FIG. 17). As expected, after 20 minutes of the study a significantly higher glucose level was observed after ingesting 150 g of bread (+ placebo XX) when compared to 100 g of bread (+ placebo IV) (100.6±2.3 and 91.0±1.5 mg/dL, respectively, p=0.002). Analysis of the percentage changes in glucose levels (FIG. 18) shows a corresponding increase in glucose levels 20 minutes after taking the 150 g bread meal (+ placebo XX) when compared to 100 g of bread (+ placebo IV) (117.3±2.0 vs. 107.6±1.8%, respectively, p=0.001).

SUBSTUDY 9—Products: I-white mulberry extract (600 mg), XVII-white mulberry extract (600 mg)+ green coffee extract (400 mg)+ white kidney bean extract (1,200 mg).

Figure 19A:
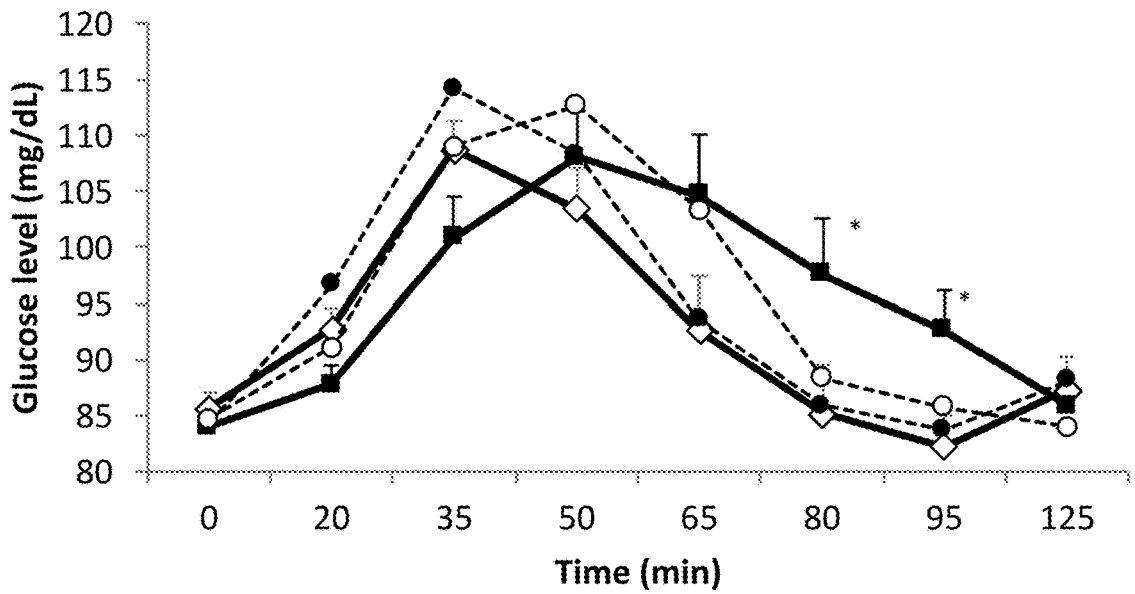
FIGS. 19A and 19B show blood glucose concentrations (mg/dL; 19A) and relative concentrations (%; 19B) in healthy subjects following consumption of white mulberry extract with 100 g bread (squares, solid line), a combination of white mulberry, green coffee and white kidney bean extracts with 150 g bread (empty diamonds, solid line), placebo with 100 g bread (solid circles, dashed line) and placebo with 150 g bread (empty circles, dashed line). *p<0.05; **p<0.01.
Figure 19B:
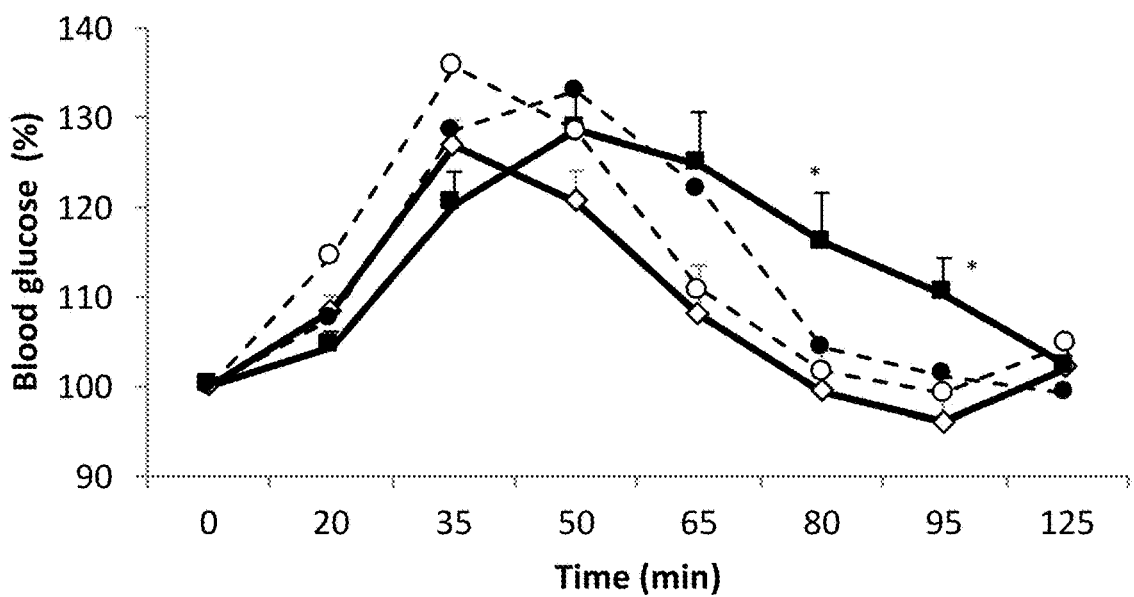

Glucose levels overtime following consumption of bread and products I (with 100 g bread), XVII (with 150 g bread) or placebo are presented in FIG. 19A, as follows: white mulberry extract (FIG. 19A; squares on a solid line) and a combination of this extract with green coffee and white kidney bean extracts (FIG. 19A; empty diamonds on a solid line) consumed with 100 g wheat bread and 150 g bread, respectively. Control subjects consumed placebo with 100 g wheat bread or 150 g bread (FIG. 19A; solid or empty circles on dashed lines, respectively). The average glucose levels after taking the combination of products (XVII) were lower compared to those levels after taking the white mulberry preparation (I) alone. In minute 65 of the experiment blood glucose levels after administration of XVII and I were 92.6±5.4 and. 104.7±4.9 mg/dL respectively (p=0.057). After 80 minutes of the study the corresponding values were 85.2±5.0 vs. 97.6±4.9 mg/dL (p=0.04) and after 95 minutes of the study the blood glucose values were 82.2±3.6 and 92.6±2.8 mg/dL for mulberry extract I and combination XVII respectively (p=0.03). The relative change in glucose levels (FIG. 19B) indicates that after 50 minutes the increase in glucose level is less pronounced for combination XVII compared to white mulberry extract, as follows: 120.7±4.4 vs. 128.6±3.4% (p=0.08, 50 min.); 108.0±5.8 vs. 124.8±5.5% (p=0.045, 65 min.); 99.5±5.5 vs. 116.1±4.5% (p=0.03, 80 min.); and 96.1±4.0 vs. 110.3±3.0%, (p=0.008, 95 min.), respectively.

At the 20 and 35 minutes time point, blood glucose levels seemed to be higher after taking combination XVII vs. mulberry extract I (92.8±1.8 vs. 87.7±1.8 mg/dL respectively, p=0.055; and 108.8±3.6 vs. 100.9±2.5 mg/dL respectively, p=0.09). It is believed that this increase was a result of the higher amount of carbohydrates provided in the meal (150 g vs. 100 g bread). Nevertheless, despite the higher amount of carbohydrates, during 50 to 95 minutes of experiment lower glucose levels were observed in the combination group compared to the corresponding levels after taking an individual extract, highlighting the advantage of the combination over the individual mulberry extract.

SUBSTUDY 10—Products: I-white mulberry extract (600 mg), XIX-white mulberry extract (600 mg)+ green coffee extract (400 mg)+ white kidney bean extract (1,200 mg)+ insulin (2000 mg)+ glucomannan (3000 mg).

Figure 20A:
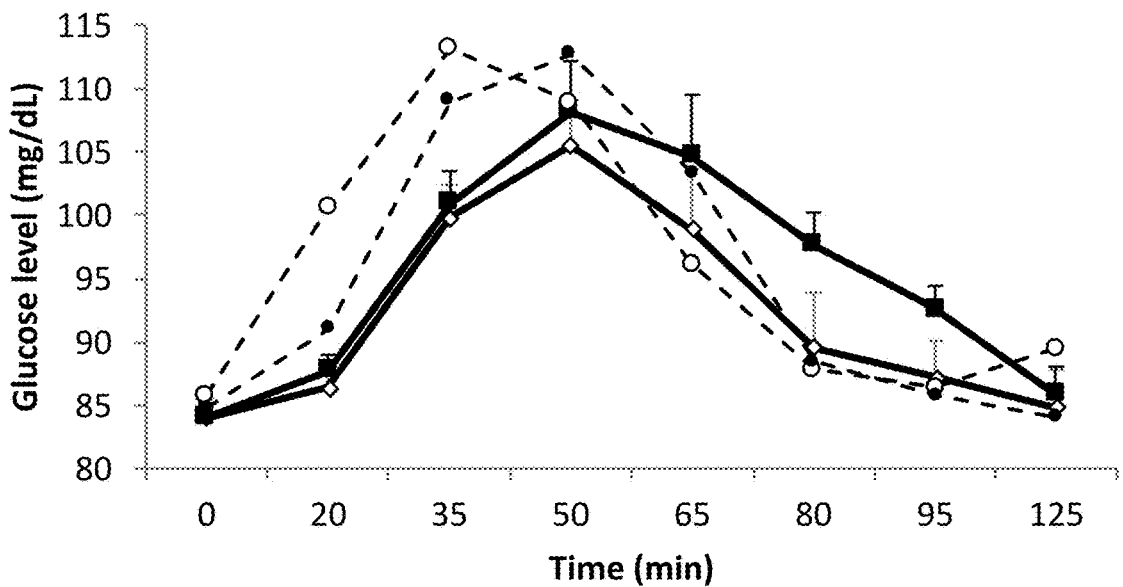
FIGS. 20A and 20B show blood glucose concentrations (mg/dL; 20A) and relative concentrations (%; 20B) in healthy subjects following consumption of white mulberry extract with 100 g bread (squares, solid line), a combination of white mulberry, green coffee and white kidney bean extracts with 150 g bread (empty diamonds, solid line), placebo with 100 g bread (solid circles, dashed line) and placebo with 150 g bread (empty circles, dashed line). *p<0.05; **p<0.01.

Glucose levels overtime following consumption of bread and products I (with 100 g bread), XIX (with 150 g bread) or placebo are presented in FIG. 20A, as follows: white mulberry extract (FIG. 20A; squares, solid line) and a combination of this extract with green coffee and white kidney bean extracts, insulin and glucomannan (FIG. 20A; empty diamonds, solid line) consumed with 100 g wheat bread and 150 g bread, respectively. Control subjects consumed placebo with 100 g wheat bread or 150 g bread (FIG. 20A; dashed lines, solid or empty circles, respectively). The average blood glucose level did not show substantial differences after taking the white mulberry preparation or the combination product with fiber. However, as noted with respect to the previous substudies, white mulberry extract (product I) was consumed along with a lower amount of carbohydrates-100 g of bread versus 150 g of wheat bread consumed with the combination product. Thus, the results in fact indicate that the combination product XIX is superior over the single extract product, as it resulted with similar glucose level despite the additional 50 g of bread. This conclusion is further supported by the trend observed after 80 and 95 minutes of the study, where combination XIX resulted with lower glucose levels compared to the individual extract, as follows: 80 minutes—89.6±2.6 (product I, 100 g bread) vs. 97.6±4.3 mg/dL (product XIX, 150 g bread)

(p=0.12); 95 minutes −87.3±1.8 (product I, 100 g bread) vs. 92.6±2.8 mg/dL (product XIX, 150 g bread) (p=0.13).

Figure 20B:
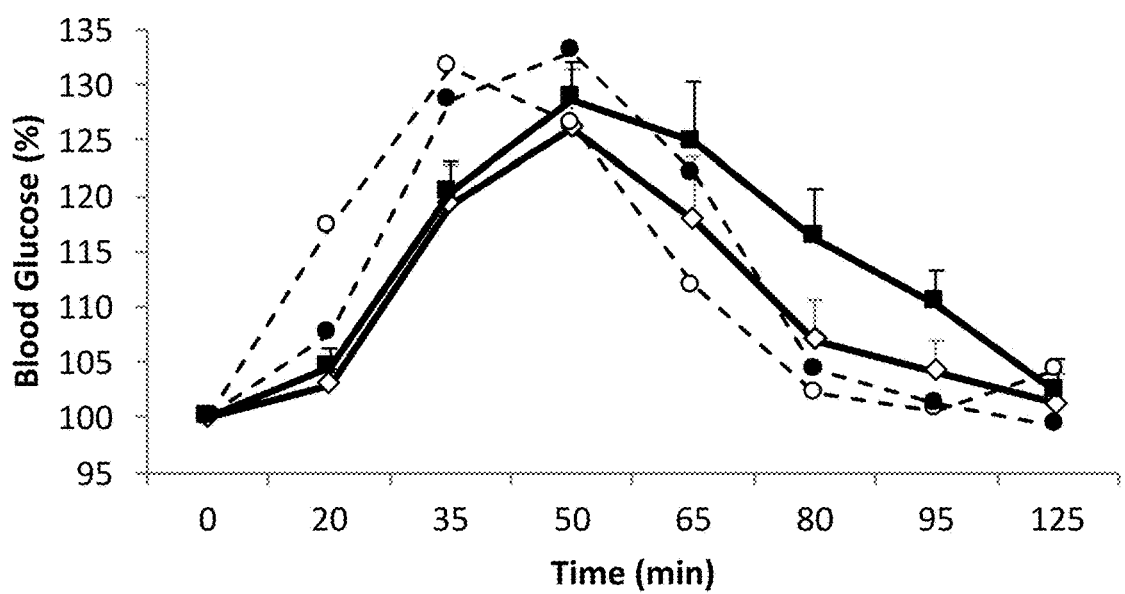

The corresponding relative changes in glucose levels (FIG. 20B) showed a similar trend towards a smaller percentage increase in average glucose levels between consumption of combination XIX versus the mulberry extract: 107.0±3.6 (XIX and 150 g of bread, 80 min.) vs. 116.1±4.5% (I and 100 g of bread, 80 min.) (p=0.12) and 104.2±2.7 (XIX and 150 g of bread, 95 min.) vs. 110.3±3.0% (I and 100 g of bread, 95 min.) (p=0.14).

SUBSTUDY 11—Products: VI-white kidney bean extract (1,200 mg), XVII-white mulberry extract (600 mg)+ green coffee extract (400 mg)+ white kidney bean extract (1,200 mg).

Figure 21A:
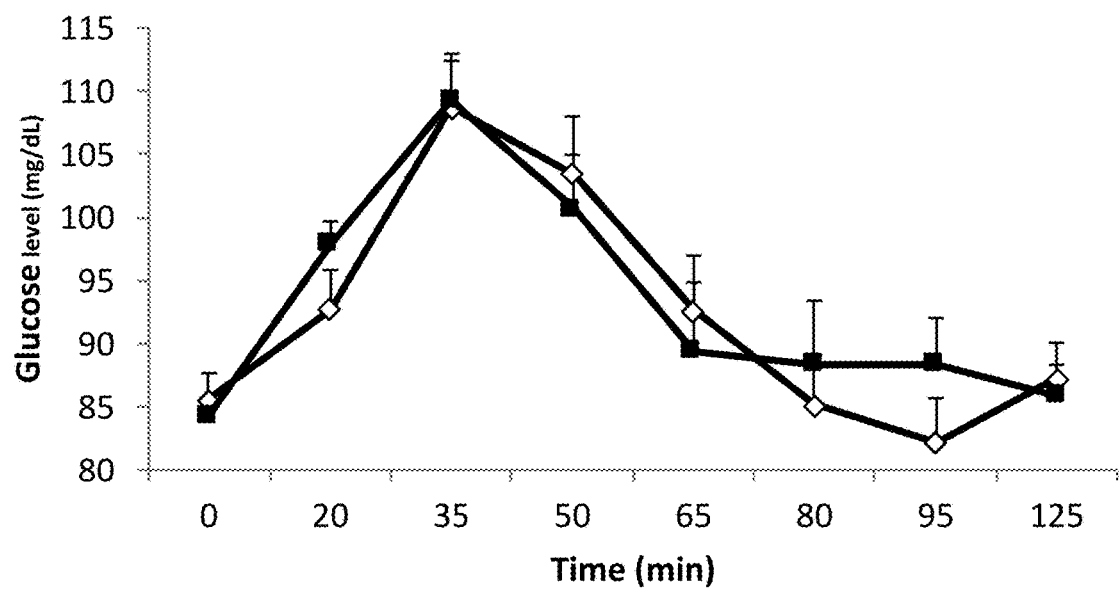
FIGS. 21A and 21B show blood glucose concentrations (mg/dL; 21A) and relative concentrations (%; 21B) in healthy subjects following consumption of 150 g bread and: white kidney bean extract (squares, solid line) or a combination of white kidney bean, white mulberry and green coffee extracts (empty diamonds, solid line).
Figure 21B:
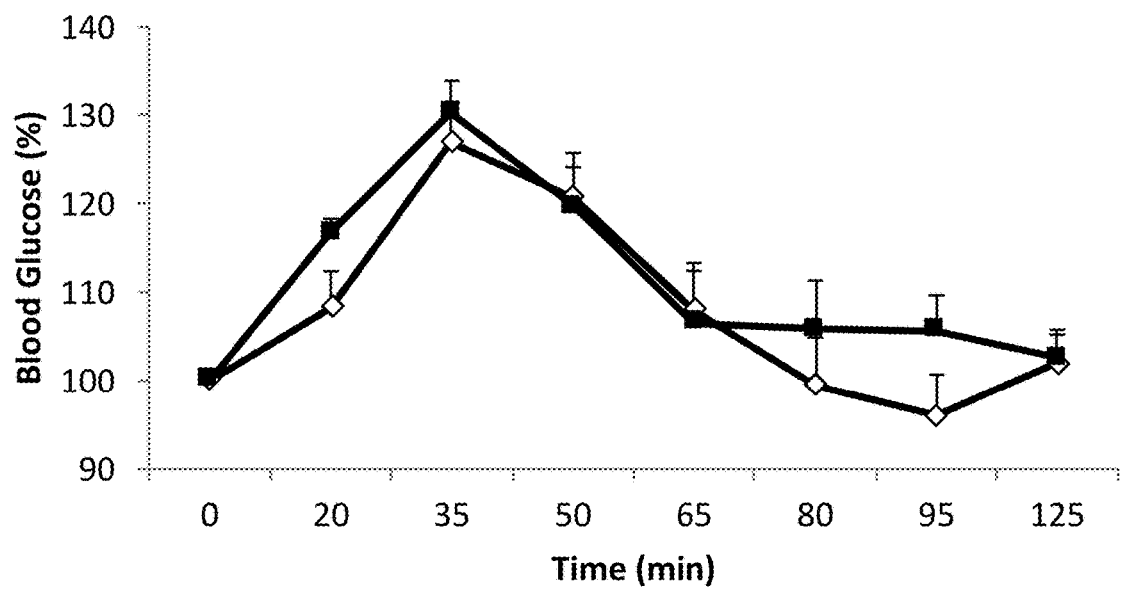

Glucose levels overtime following consumption of 150 g bread and products VI or XVII are presented in FIG. 21A, as follows: white kidney bean extract (FIG. 21A; squares, solid line) and a combination of this extract with green coffee and white mulberry extracts (FIG. 21A; empty diamonds, solid line). A trend (p=0.16) towards lower glucose levels after taking combination XVII was observed after 20 minutes compared to bean extract VI-92.8±1.8 vs. 97.9±3.0 mg/dL, respectively. The corresponding relative changes (FIG. 21B) showed tendency towards increase in glucose levels after consuming the combination product XVII compared to the single extract (white kidney bean extract, product VI) after 20 minutes of the study (108.4±1.6 vs. 116.7±4.0%, respectively, p=0.13) and after 95 minutes of the study (96.1±4.0 vs. 105.6±4.6%, respectively, p=0.13).

SUBSTUDY 12—Products: Products: VI-white kidney bean extract (1,200 mg), XIX-white mulberry extract (600 mg)+ green coffee extract (400 mg)+ white kidney bean extract (1,200 mg)+ insulin (2000 mg)+ glucomannan (3000 mg).

Figure 22A:
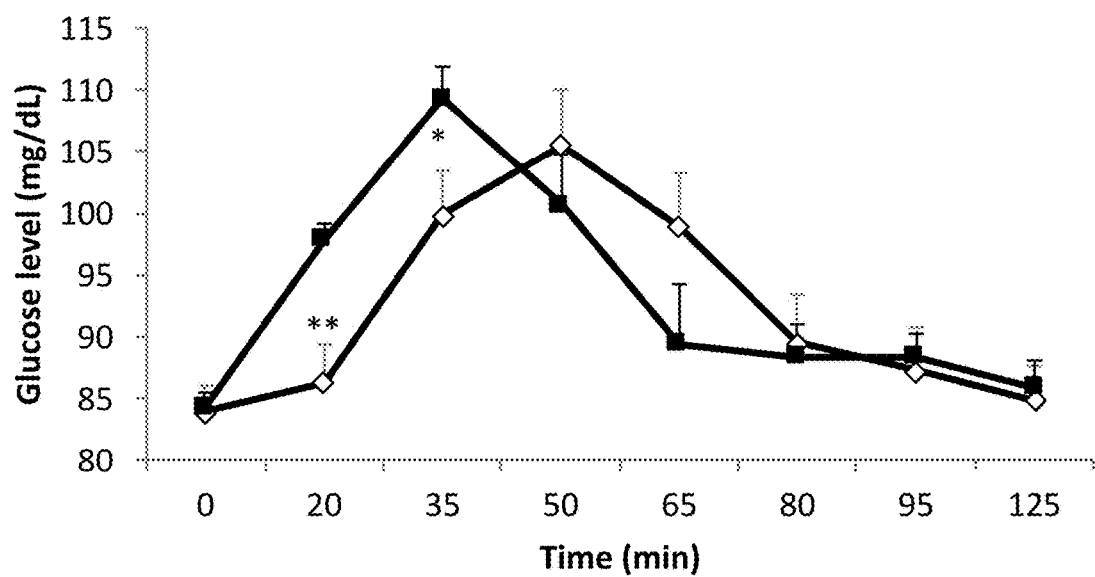
FIGS. 22A and 22B show blood glucose concentrations (mg/dL; 22A) and relative concentrations (%; 22B) in healthy subjects following consumption of 150 g bread and: white kidney bean extract (squares, solid line) or a combination of white kidney bean, white mulberry and green coffee extracts, insulin and glucomannan (empty diamonds, solid line). *p<0.05; **p<0.01.
Figure 22B:
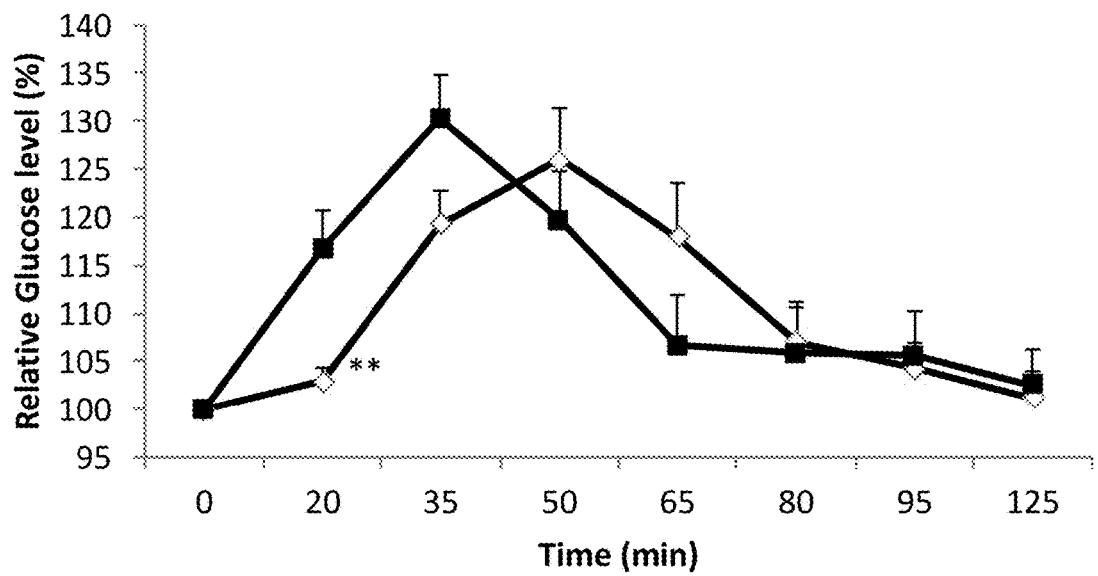

Glucose levels overtime following consumption of 150 g bread and products VI or XIX are presented in FIG. 22A, as follows: white kidney bean extract (FIG. 22A; squares, solid line) and a combination of this extract with green coffee and white mulberry extracts, insulin and glucomannan (FIG. 22A; empty diamonds, solid line). Average glucose levels were substantially lower after taking the combination of products with fiber (product XIX) compared to bean extract alone (product VI) after 20 minutes of the study (86.3±3.6 vs. 97.9±3.0 mg/dL, respectively, p=0.002) and after 35 minutes of the study (99.8±2.6 vs. 109.3±3.6 mg/dL, respectively, p=0.04). The corresponding relative increase in glucose levels (FIG. 22B) was substantially smaller after taking preparation XIX compared to the extract VI after 20 minutes of the study (102.9±1.4 vs. 116.7±4.0%, respectively, p=0.002).

SUBSTUDY 13—Products: VII-green coffee extract (400 mg), XVII-white mulberry extract (600 mg)+ green coffee extract (400 mg)+ white kidney bean extract (1,200 mg).

Figure 23A:
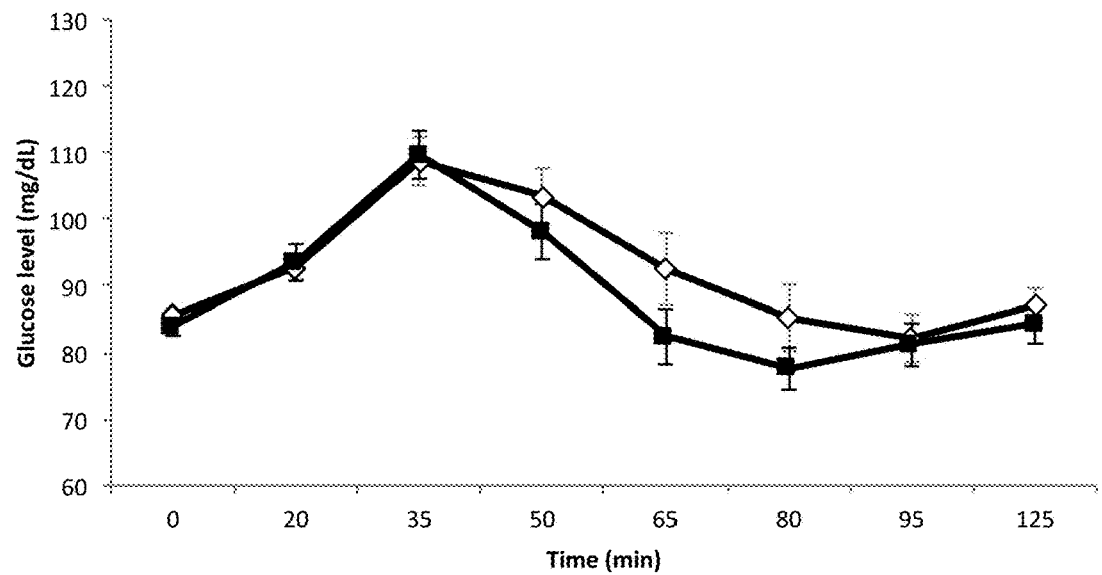
FIGS. 23A and 23B show blood glucose concentrations (mg/dL; 21A) and relative concentrations (%; 21B) in healthy subjects following consumption of 150 g bread and: green coffee extract (squares, solid line) or a combination of white kidney bean, white mulberry and green coffee extracts (empty diamonds, solid line).
Figure 23B:
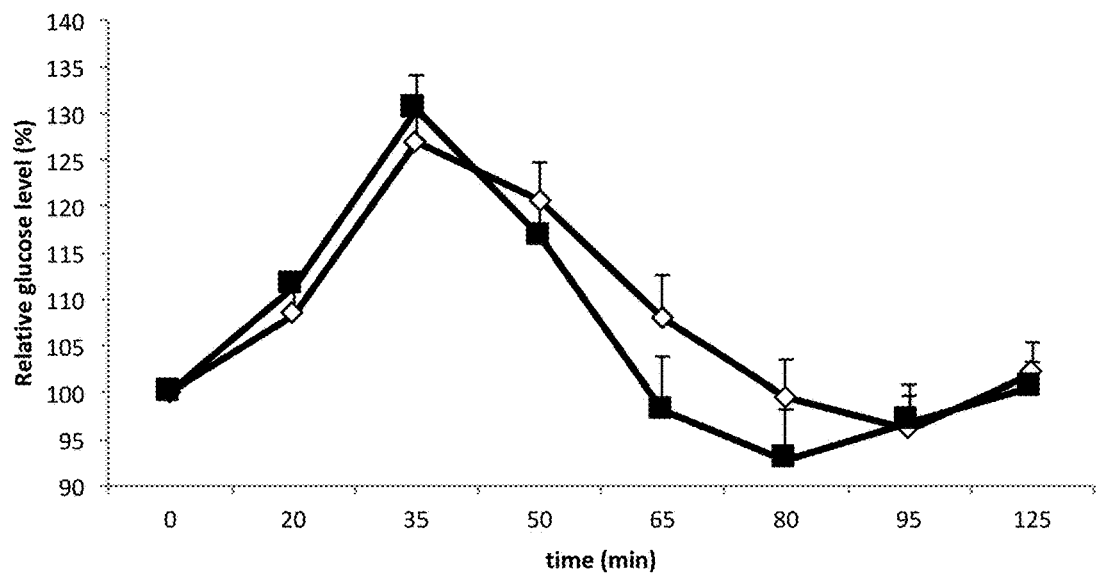

Glucose absolute and relative levels overtime following consumption of 150 g bread and products VII or XVII are presented in FIGS. 23A and 23B, respectively, as follows: green coffee extract (FIG. 23A; squares, solid line) and a combination of this extract with green coffee and white kidney bean extracts (FIG. 23A; empty diamonds, solid line). No significant differences were observed following consumption of the single extract (product VII) compared to the combination (product XVII).

SUBSTUDY 14—Products: Products: VII-green coffee extract (400 mg), XIX-white mulberry extract (600 mg)+ green coffee extract (400 mg)+ white kidney bean extract (1,200 mg)+ insulin (2,000 mg)+ glucomannan (3,000 mg).

Figure 24A:
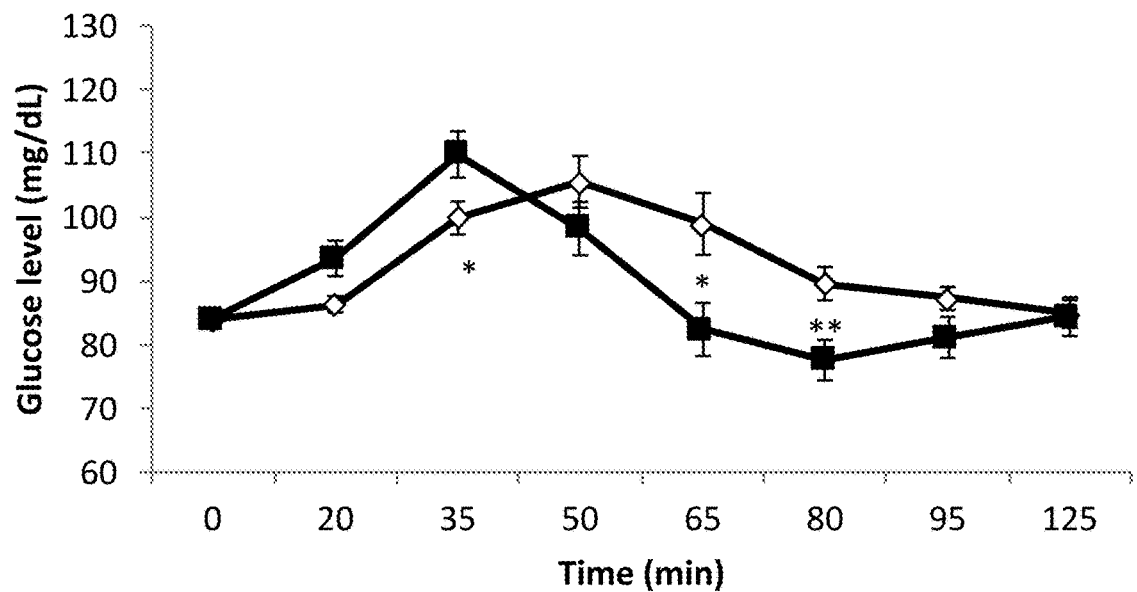
FIGS. 24A and 24B show blood glucose concentrations (mg/dL; 24A) and relative concentrations (%; 24B) in healthy subjects following consumption of 150 g bread and: green coffee extract (squares, solid line) or a combination of white kidney bean, white mulberry and green coffee extracts, insulin and glucomannan (empty diamonds, solid line). *p<0.05; **p<0.01.
Figure 24B:
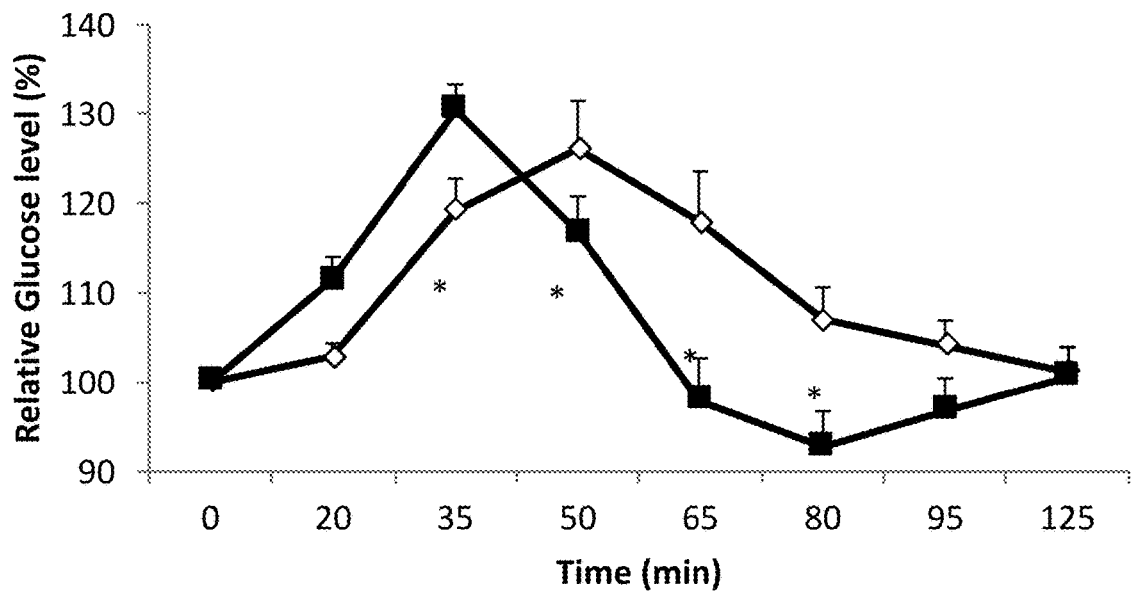

Glucose absolute and relative levels overtime following consumption of 150 g bread and products VII or XIX are presented in FIGS. 24A and 24B, respectively, as follows: green coffee extract (FIG. 24A; squares, solid line) and a combination of this extract with green coffee and white kidney bean extracts, insulin and glucomannan (FIG. 24A; empty diamonds, solid line). As presented in FIG. 23A, the combination product XIX was more efficient than extract VII in preventing blood glucose increase during the first postprandial phase prior to their return to normal values (i.e. during the initial 35 minutes). The values of glucose in the blood following 20 and 35 minutes after consuming combination XIX and single extract VII, respectively, are as follows: glucose levels and were as follows: 86.3±1.3 vs. 93.5±2.8 mg/dL respectively (p=0.052, 20 min.) and 99.8±2.6 vs. 109.8±3.6 mg/dL respectively (p=0.03, 35 min.). In the late postprandial phase blood glucose levels were lower in the single product group. This phenomenon may be attributed to an excessive insulin burst corresponding to the glucose level burst during the first postprandial phase in the single product group. The corresponding relative changes (FIG. 24B) also demonstrated a significantly smaller increase in glucose levels following consumption of the combination product XIX during the 20 and 35 minutes of the study compared to the coffee extract, as follows: 102.9±1.4 (extract VII) vs. 111.4±2.6% (combination XIX) after 20 minutes (p=0.02) and 119.2±3.5 (extract VII) vs. 130.4±2.9% (combination XIX) after 35 minutes (p=0.02).

SUBSTUDY 15—Products: Products: XIII-insulin+glucomannan (2+3 g), XIX-white mulberry extract (600 mg)+ green coffee extract (400 mg)+ white kidney bean extract (1,200 mg)+ insulin (2,000 mg)+ glucomannan (3,000 mg).

Figure 25A:
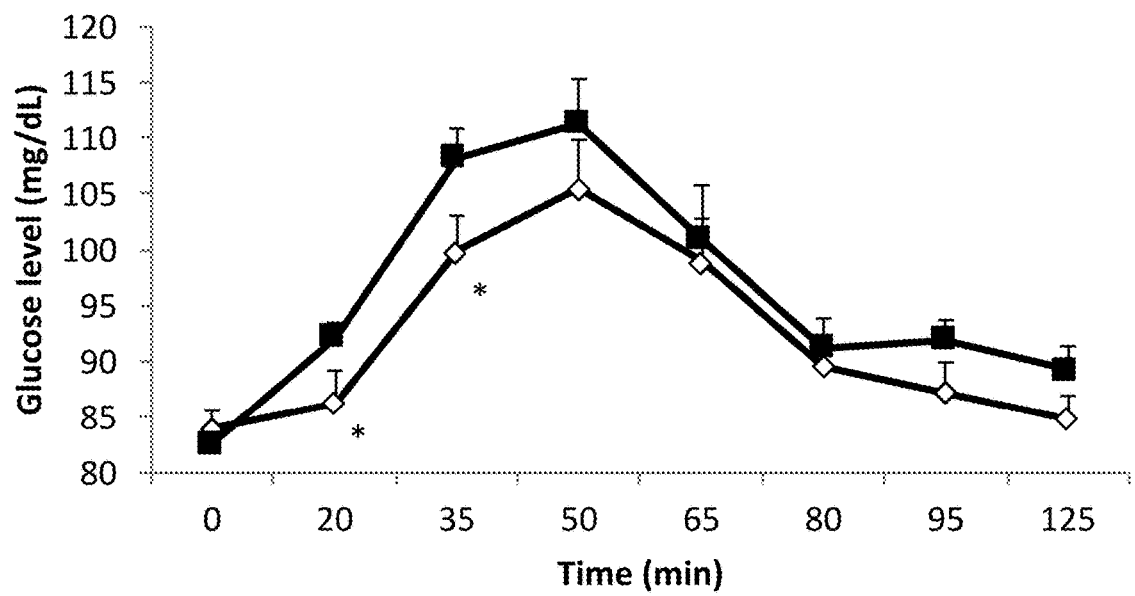
FIGS. 25A and 25B show blood glucose concentrations (mg/dL; 25A) and relative concentrations (%; 25B) in healthy subjects following consumption of 150 g bread and: inulin and glucomannan (squares, solid line) or a combination of white kidney bean, white mulberry and green coffee extracts, insulin and glucomannan (empty diamonds, solid line). *p<0.05; **p<0.01.
Figure 25B:
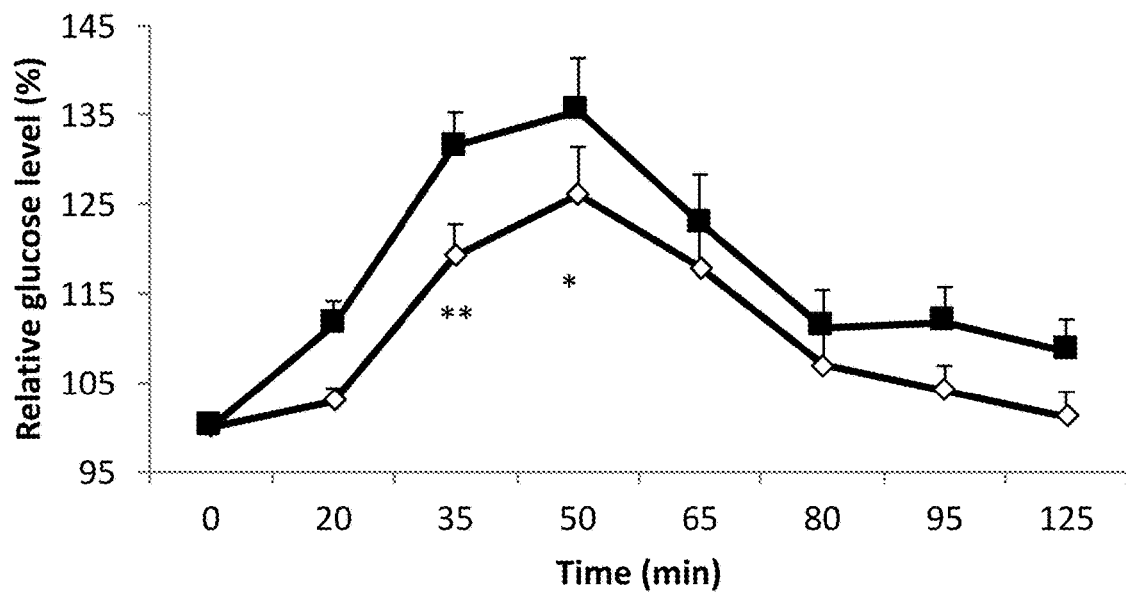

Glucose absolute and relative levels overtime following consumption of 150 g bread and products XIII or XIX are presented in FIGS. 25A and 25B, respectively, as follows: insulin and glucomannan (FIG. 25A; squares, solid line) and a combination of insulin and glucomannan with white kidney bean, white mulberry and green coffee extracts (FIG. 25A; empty diamonds, solid line). Average glucose levels were lower following consumption of the combination of extracts with fiber (product XIX) compared to the fiber alone (product XIII) after 20 minutes of the study: 86.3±1.3 vs. 92.2±2.8 mg/dL, respectively (p=0.04951) and after 35 minutes of the study: 99.8±2.6 vs. 108.3±3.2 mg/dL respectively (p=0.049). The corresponding relative increase (FIG. 25B) showed a similar trend: at 20 minutes—102.9±1.4 vs. 111.6±2.6%, respectively (p=0.007); at 35 minutes—119.2±3.5 vs. 131.4±3.9%, respectively (p=0.03). This trend was also witnessed after 95 minutes of the study: 104.2±2.7 (combination XIX) vs. 111.8±3.9% (fiber XIII) (p=0.12) and after 125 minutes of the study: 101.2±2.8 (combination XIX) vs. 108.7±3.5% (fiber XIII) (p=0.10).

Example 9: The Effect of Optimized Combinations after Consumption of Selected Meals—Clinical Studies The effects of the combination of white mulberry extract, white kidney bean extract and green coffee (product XVII in Example 7, substudy 5) on human blood glucose levels were tested in an experiment conducted with volunteers with BMI ranging from 22.99 to 29.99 kg/m$^2$. Each of the study groups consisted of 30 healthy subjects. During the experimental period, the subjects were administered study test product XVII: white mulberry extract (600 mg)+ green coffee extract (400 mg)+ white kidney bean extract (1,200 mg) or placebo. Thereafter the participants received a meal according to the description mentioned below, for each substudy: Substudy 16—breakfast flakes meal with vanilla milk; Substudy 17—a blueberry muffin and a blueberry drinking yoghurt; Substudy 18-pasta with cheese sauce and Substudy 19—Coke-type beverage (400 ml, Coca-Cola®) and Puffcorn™.

SUBSTUDY 16—Breakfast flakes (50 g, Cheerios, Nestle®) with vanilla milk (400 ml)

Figure 26A:
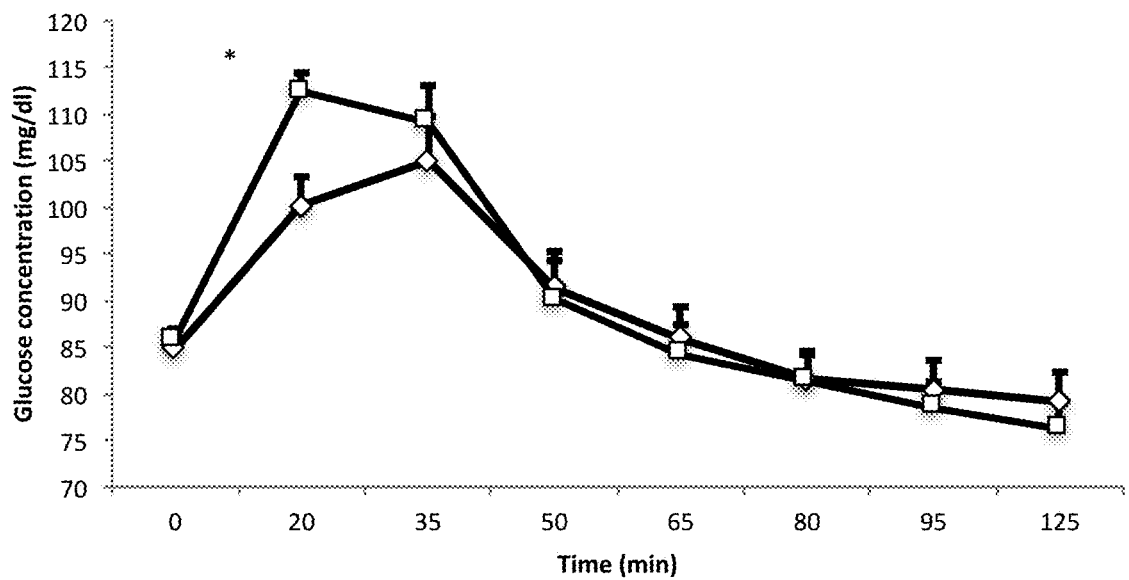
FIGS. 26A and 26B show blood glucose concentrations (mg/dL; 26A) and concentrations relative to fasting at t=0 (%; 26B) in healthy subjects following consumption of a combination of white kidney bean, white mulberry and green coffee extracts (diamonds) or placebo (squares) prior to a meal of breakfast flakes with vanilla milk. *p<0.05; **p<0.01.
Figure 26B:
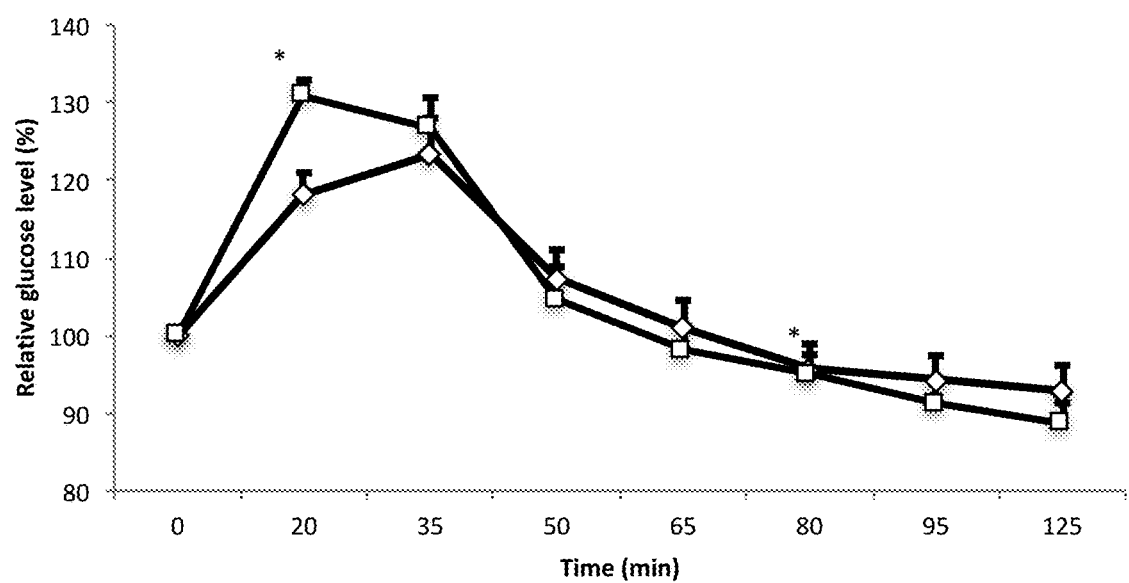

FIGS. 26A and 26B present glucose concentration (mg/dL) and glucose amounts relative to fasting (t=0; %), respectively, following consumption of the tested combination (Product XVII; diamonds) or placebo (squares). Significantly (p=0.0002) lower levels of glucose were observed 20 minutes after food consumption following consumption of extracts combination XVII relative to placebo: 110.2±2.0 vs. 112.5±3.1 mg/dl, respectively.

A similar trend was observed in glucose amounts relative to fasting (FIG. 26B): 118.2±2.1 vs. 130.8±2.8% for the tested product and the placebo, respectively (p=0.00002, 20 min.). Thus, at 20 minutes after the meal, the tested product significantly suppressed glucose surge, relative to placebo. This trend was maintained at 35 minutes.

Figure 27A:
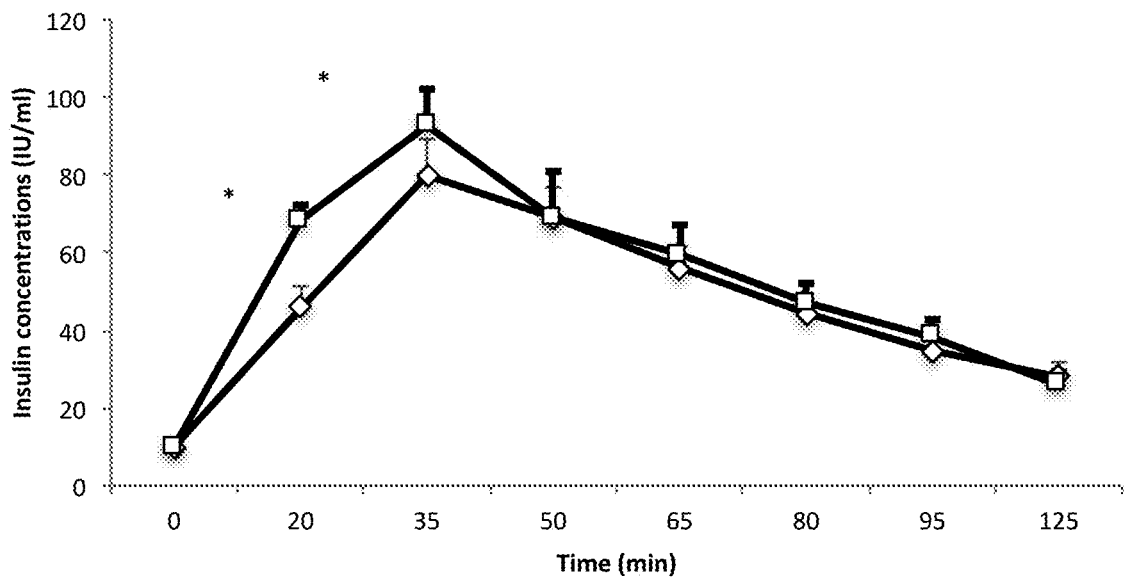
FIGS. 27A and 27B show insulin concentrations (IU/ml; 27A) and concentrations relative to fasting at t=0 (%; 27B) in healthy subjects following consumption of a combination of white kidney bean, white mulberry and green coffee extracts (diamonds) or placebo (squares) prior to a meal of breakfast flakes with vanilla milk. *p<0.05; **p<0.01.

Insulin levels were lower upon administration of combination XVII compared to placebo (FIG. 27A) in min. 20: 45.9±4.0 vs. 68.2±5.5 IU/ml, respectively, p=0.0002 and in min. 35: 79.9±9.4 vs. 92.7±9.3 IU/ml, respectively, p=0.037. A significant lower value of the area under the curve for insulin concentrations was also witnessed after ingesting the tested product vs. placebo: 5836.5±585.4 vs. 6578.4±454.8 respectively p=0.04).

Figure 27B:
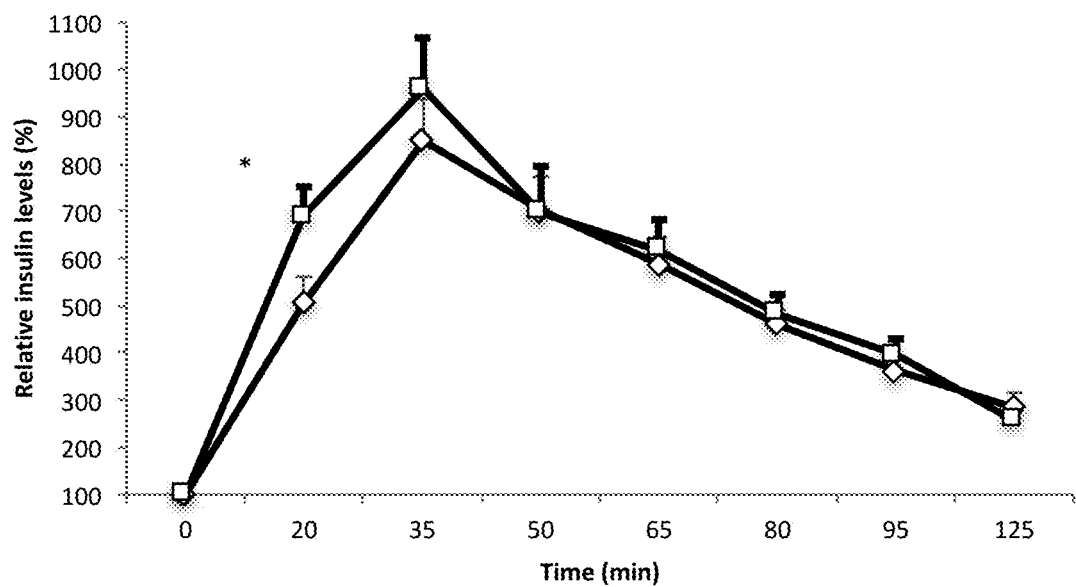

A similar trend was observed for the relative (to fasting; t=0) levels of insulin (FIG. 27B): 506.8±62.1 vs. 689.6±54.2% (p=0.005, 20 min.) and 848.9±108.5 vs. 958.7±89.3% (p=0.099, 35 min.) for product XVII and placebo, respectively.

SUBSTUDY 17—Blueberry muffin (Starbucks, Poland) and a blueberry drinking yoghurt (300 g, Activia, Poland)

Figure 28A:
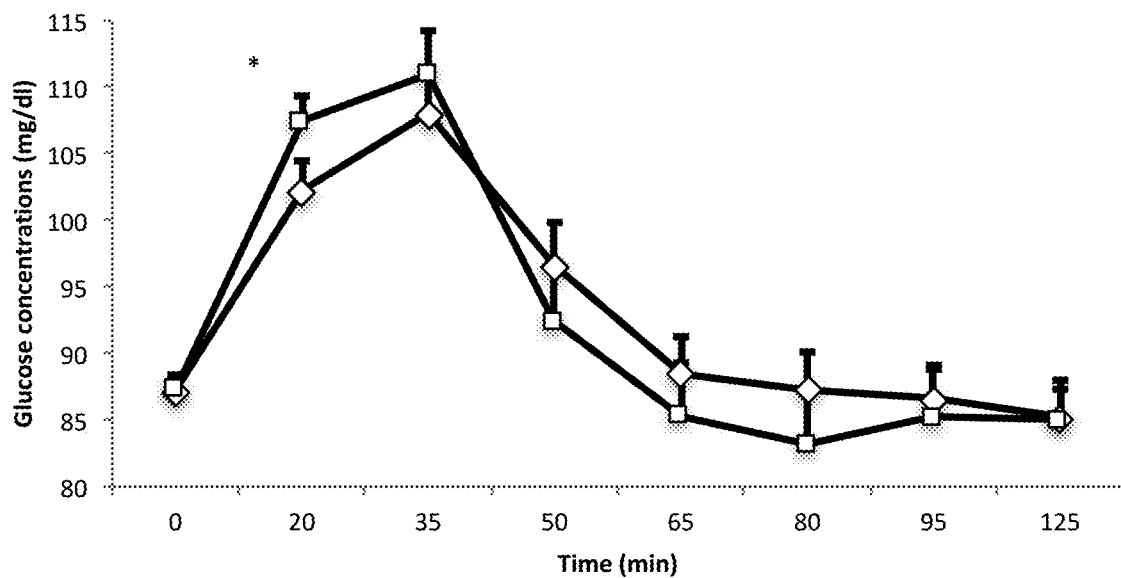
FIGS. 28A and 28B show blood glucose concentrations (mg/dL; 28A) and concentrations relative to fasting at t=0 (%; 28B) in healthy subjects following consumption of a combination of white kidney bean, white mulberry and green coffee extracts (diamonds) or placebo (squares) prior to a meal of blueberry muffin and blueberry yogurt. *p<0.05; **p<0.01.
Figure 28B:
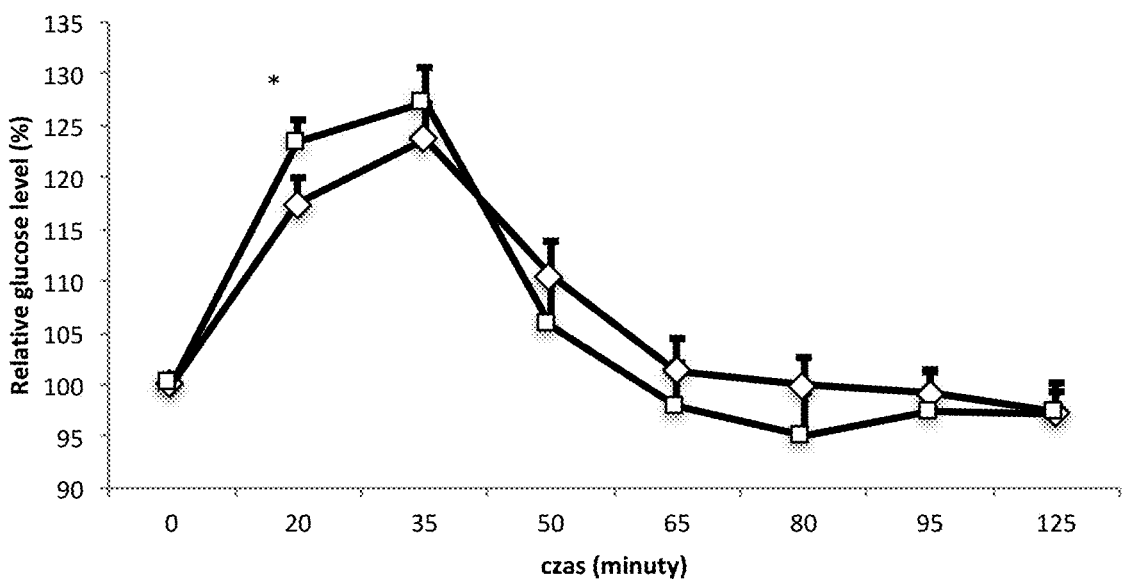

FIGS. 28A and 28B present glucose concentration (mg/dL) and glucose amounts relative to fasting (t=0; %), respectively, following consumption of the tested combination (Product XVII; diamonds) or placebo (squares) prior to a meal of blueberry muffin and blueberry yogurt. In min. 20 of this substudy significantly (p=0.005) lower levels of glucose were observed after consumption product XVII: 102.2±1.9 mg/dl compared the corresponding levels after consumption of placebo 107.5±2.2 mg/dl (FIG. 28A). Furthermore, percentage increase in glucose concentrations after ingesting the tested product was significantly lower in comparison with control: 117.4±2.3 vs. 123.3±2.6% respectively (p=0.003, 20 min.) (FIG. 28B).

Figure 29A:
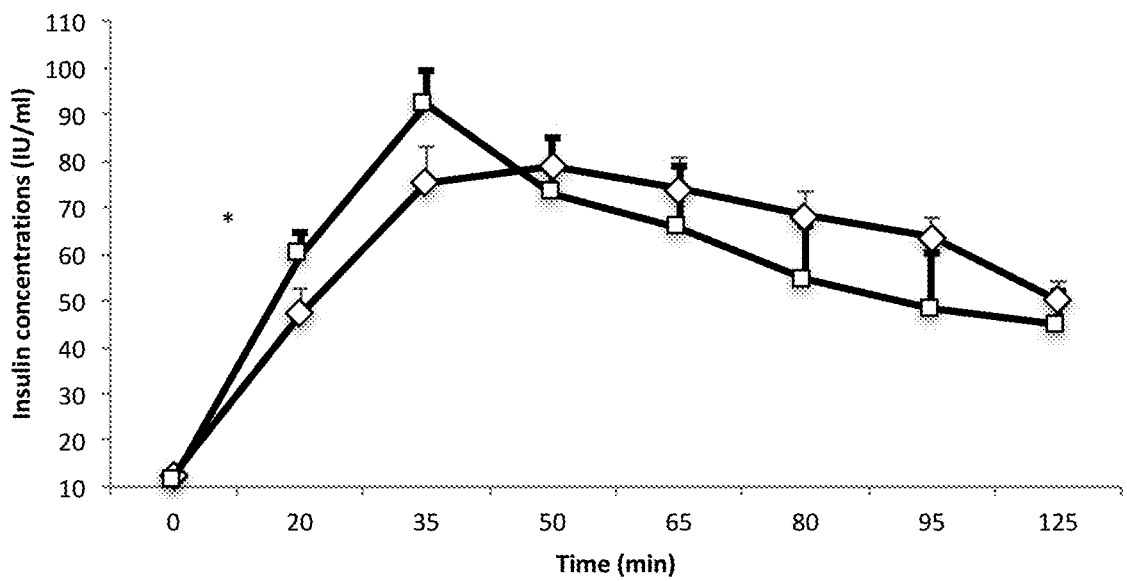
FIGS. 29A and 29B show insulin concentrations (IU/ml; 29A) and concentrations relative to fasting at t=0 (%; 29B) in healthy subjects following consumption of a combination of white kidney bean, white mulberry and green coffee extracts (diamonds) or placebo (squares) prior to a meal of blueberry muffin and blueberry yogurt. *p<0.05; **p<0.01.
Figure 29B:
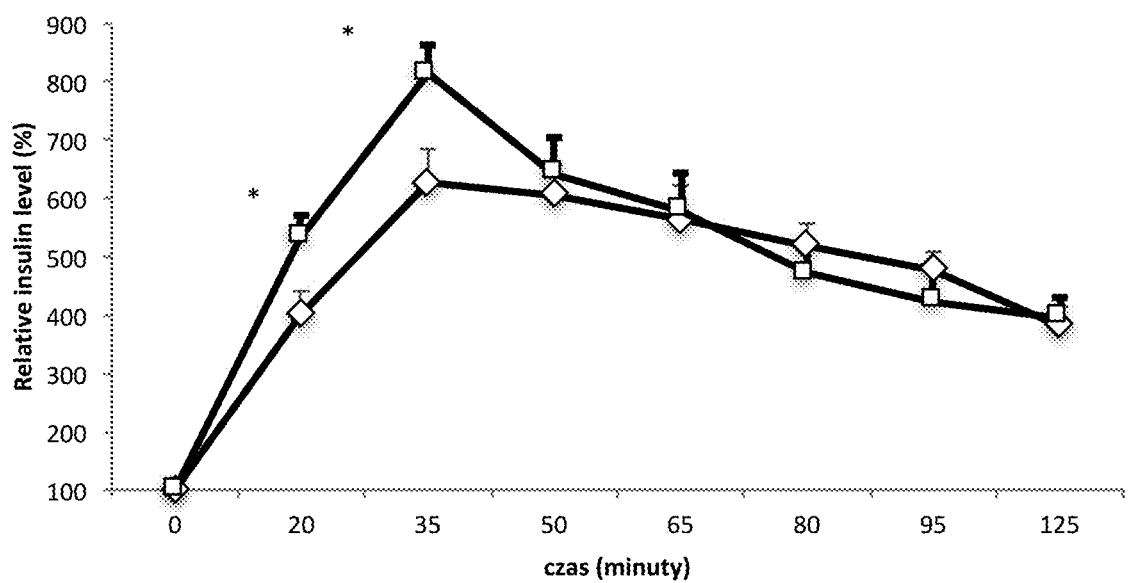

Insulin levels were also lower upon administration of combination XVII vs. control-in min. 20: 47.3±4.7 vs. 59.9±5.3 IU/ml, respectively, p=0.01 and in min. 35: 75.5±7.3 vs. 92.1±7.5 IU/ml, respectively, p=0.069, (FIG. 29A). The percentage increase in insulin concentrations in comparison after taking product XVII was significantly lower compared with placebo: 401.4±38.3 vs. 532.7±39.6% (p=0.0002, 20 min.) and 627.2±48.4 vs. 815.0±57.8% respectively (p=0.01, 35 min.) (FIG. 29B).

SUBSTUDY 18—Pasta with cheese sauce (58 g, Macaroni&Cheese Dinner, KRAFT®)

Figure 30A:
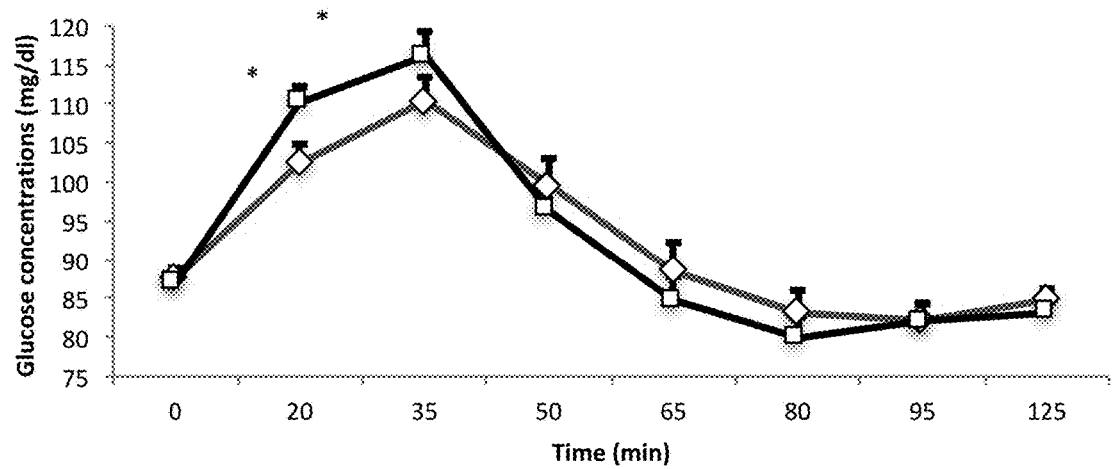
FIGS. 30A and 30B show blood glucose concentrations (mg/dL; 30A) and concentrations relative to fasting at t=0 (%; 30B) in healthy subjects following consumption of a combination of white kidney bean, white mulberry and green coffee extracts (diamonds) or placebo (squares) prior to a meal of pasta and cheese. *p<0.05; **p<0.01.
Figure 30B:
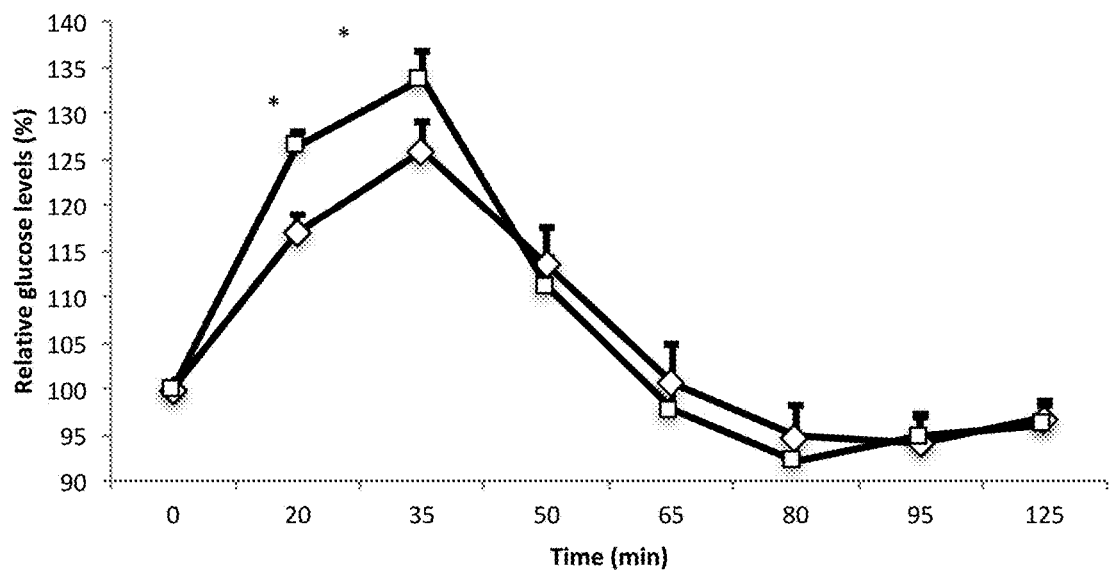

FIGS. 30A and 30B present glucose concentration (mg/dL) and glucose amounts relative to fasting (t=0; %), respectively, following consumption of the tested combination (Product XVII; diamonds) or placebo (squares) prior to a meal of pasta and cheese. In this sub study significantly (p=0.0005) lower levels of glucose were determined after consumption of the meal upon administration of extract combination XVII compared with control, in min. 20: 102.5±2.0 vs. 110.3±2.4 mg/dl respectively and in min 35: 110.4±3.1 vs. 116.2±3.0 mg/dl respectively (FIG. 30A). Moreover, percentage increase in glucose concentrations after ingesting the tested product was significantly lower in comparison with control: 117.0±1.6 (product XVII) vs. 126.4±2.0% (placebo), (p=0.00007, 20 min.) and 126.0±3.0 (product XVII) vs. 133.8±3.1% (placebo), (p=0.03, 35 min.), (FIG. 30B).

Figure 31A:
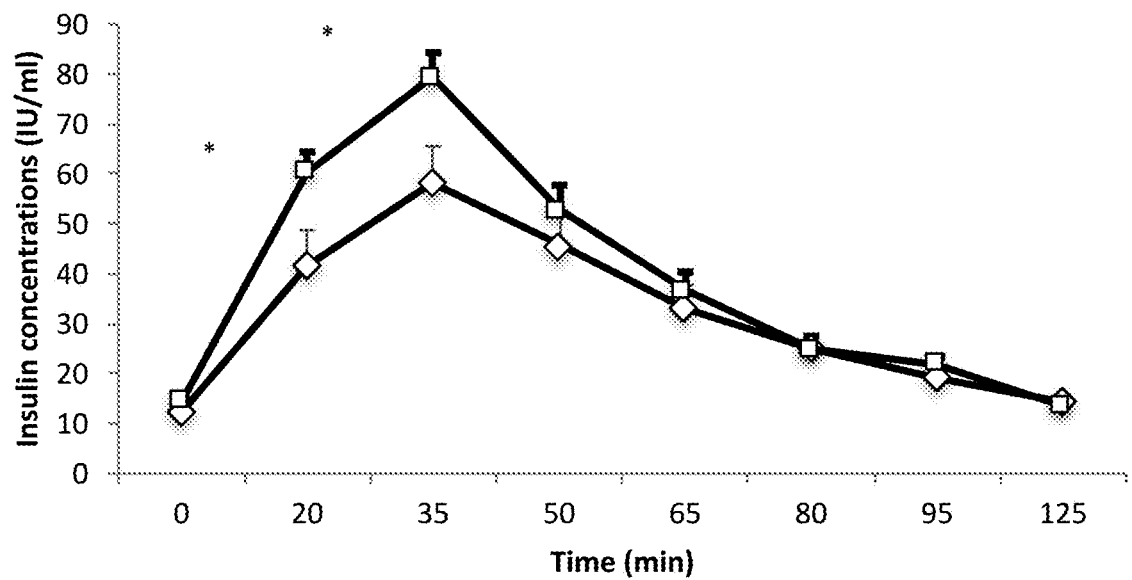
FIGS. 31A and 31B show insulin concentrations (IU/ml; 31A) and concentrations relative to fasting at t=0 (%; 31B) in healthy subjects following consumption of a combination of white kidney bean, white mulberry and green coffee extracts (diamonds) or placebo (squares) prior to a meal of pasta and cheese. *p<0.05; **p<0.01.
Figure 31B:
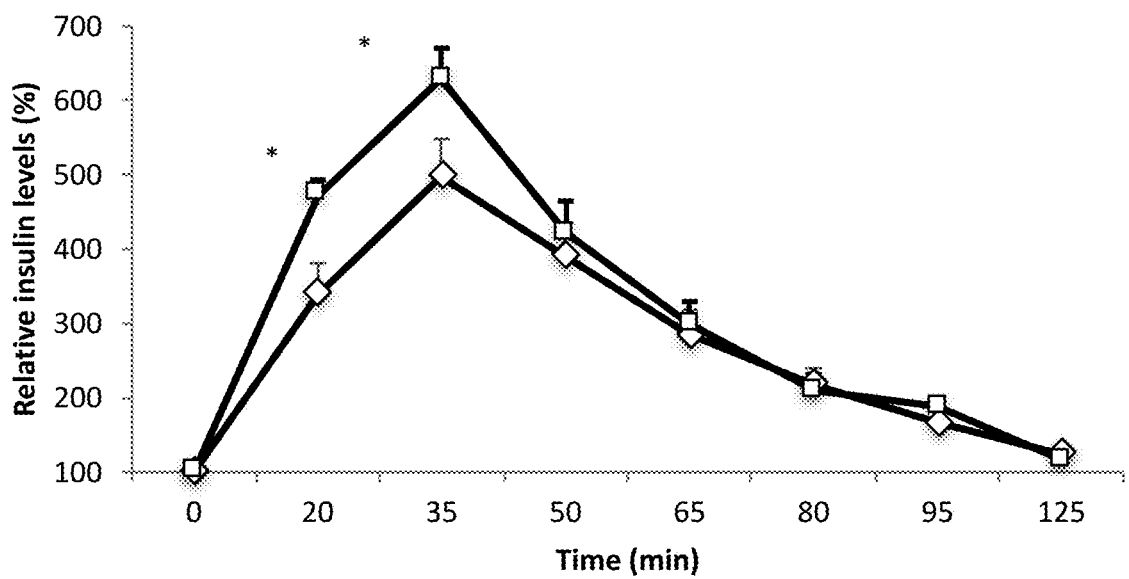

Insulin levels were also lower upon administration of combination XVII vs. control-in min. 20: 41.8±3.9 vs. 60.5±7.0 IU/ml, respectively (p=0.008), and in min. 35: 58.2±4.8 vs. 79.4±7.4 IU/ml, respectively, p=0.001 (FIG. 31A). A significant lower value of the area under the curve for insulin concentrations was also witnessed after ingesting the tested product vs. placebo: 3938.1±285.1 vs. 4802.8±380.0 respectively p=0.005), (FIG. 31A). The percentage increase in insulin concentrations in comparison after taking product XVII was significantly lower compared with placebo: 339.9±21.5 vs. 472.1±41.4% (p=0.005, 20 min.) and 497.7±41.3 vs. 629.5±50.8% respectively (p=0.002, 35 min.) (FIG. 31B).

SUBSTUDY 19—Coke-type beverage (400 ml, Coca-Cola®) and Puffcorn™ (50 g, Flips™)

Figure 32A:
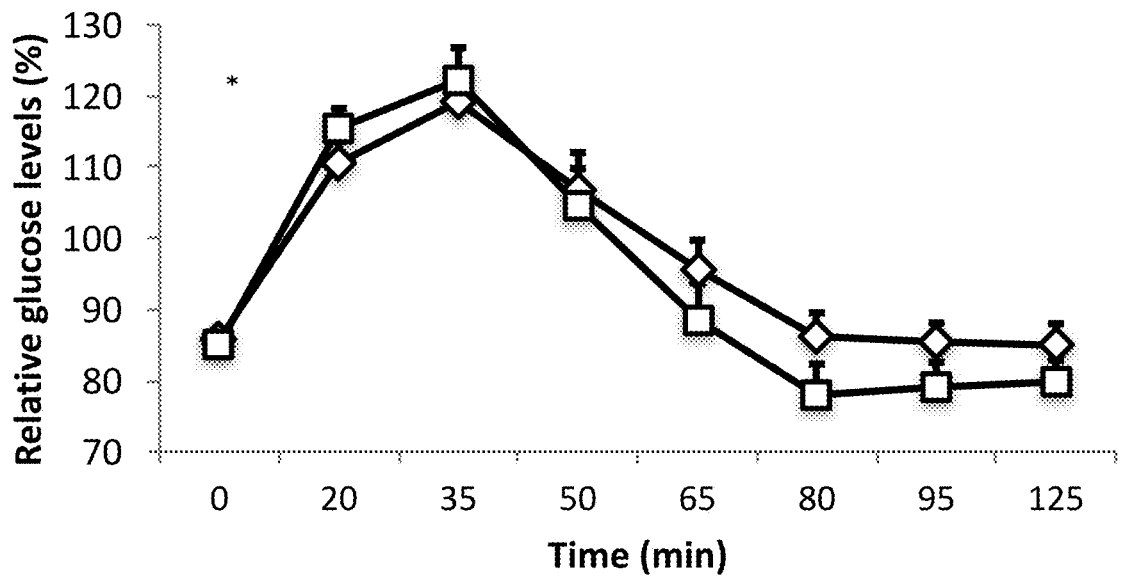
FIGS. 32A and 32B show blood glucose concentrations (mg/dL; 32A) and concentrations relative to fasting at t=0 (%; 32B) in healthy subjects following consumption of a combination of white kidney bean, white mulberry and green coffee extracts (diamonds) or placebo (squares) prior to a meal of Coca Cola® and Puffcorn™. *p<0.05; **p<0.01.
Figure 32B:
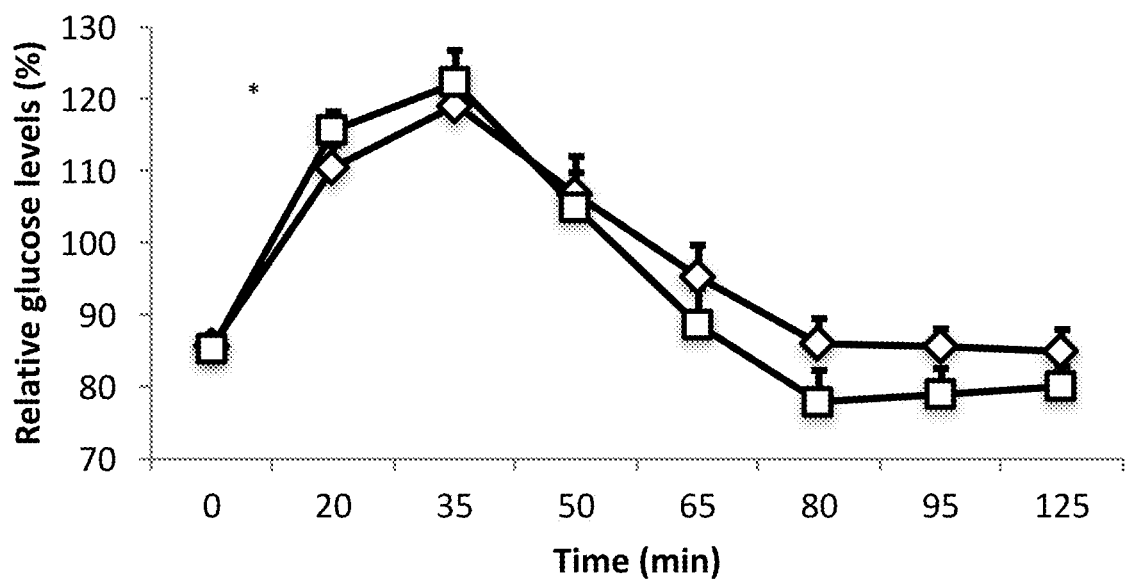

FIGS. 32A and 32B present glucose concentration (mg/dL) and glucose amounts relative to fasting (t=0; %), respectively, following consumption of the tested combination (Product XVII; diamonds) or placebo (squares) prior to consuming Coca Cola and Puffcorn™. In this substudy significantly lower glucose concentration (p=0.04) was observed 20 minutes after ingestion of the study product compared to placebo (110.6±2.7 vs. 115.6±3.0 mg/dl, respectively). An opposite tendency towards lower glucose concentrations upon taking placebo vs. the studied product was noted in minute 65 (88.6±4.3 vs. 95.4±5.1 mg/dl respectively, p=0.09) and minute 95 (85.6±3.6 vs. 79.0±2.5 mg/dl respectively, p=0.06). The overall profile of glucose in subjects receiving the product is smooth compared to the peaks and troughs of glucose in the blood of the placebo patients. Without being bound by any theory or mechanism, the hypoglycemic episodes (exceptionally low blood glucose) at minute 65 of the placebo group is most likely associated with the high insulin secretion after the high glycemic index meal. The preventive effect of the product on hypoglycemia is shown for example, by the following extreme glucose concentration incidents: 49.5 (placebo) vs. 62.5 mg/dl (product XVII, min. 65); and 33.0 (placebo) vs. 51.0 mg/dl (product XVII, min. 80).

The surge and drop (%) in glucose concentrations relative to fasting values (FIG. 32B) were again significantly smaller after ingestion of the study product compared to placebo: 129.0±2.7 vs. 136.0±3.3% respectively (p=0.009). Thus, the relative values also reflected the preventive effect of the product on excess glucose surge and glucose drop, which renders it suitable for treating or preventing hyperglycemia and hypoglycemia and/or maintaining balanced blood sugar concentrations.

Figure 33A:
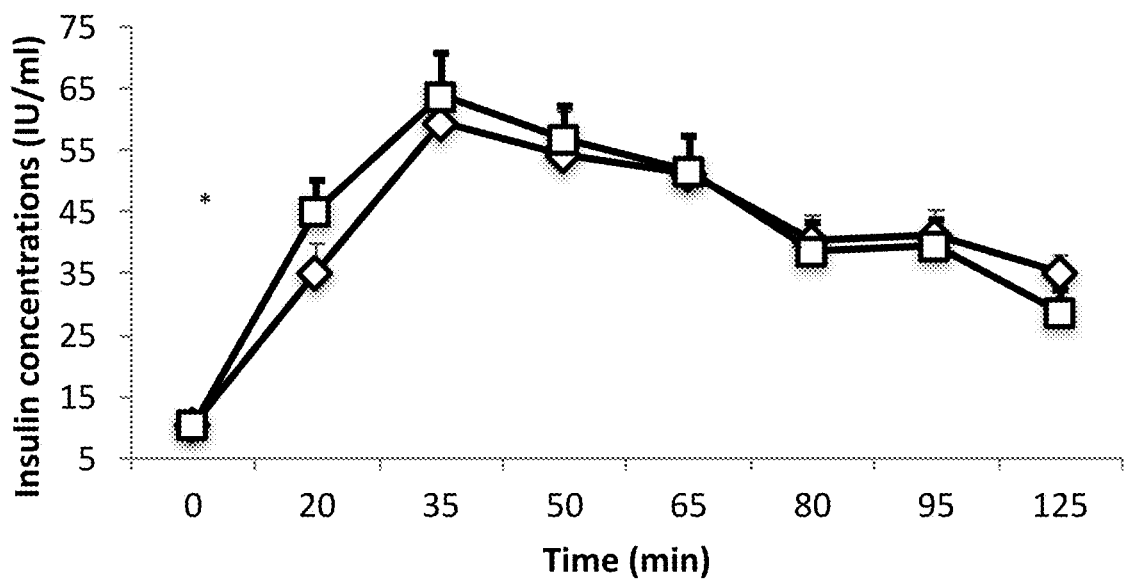
FIGS. 33A and 33B show insulin concentrations (IU/ml; 33A) and concentrations relative to fasting at t=0 (%; 33B) in healthy subjects following consumption of a combination of white kidney bean, white mulberry and green coffee extracts (diamonds) or placebo (squares) prior to a meal of Coca Cola and Puffcorn™. *p<0.05; **p<0.01.
Figure 33B:
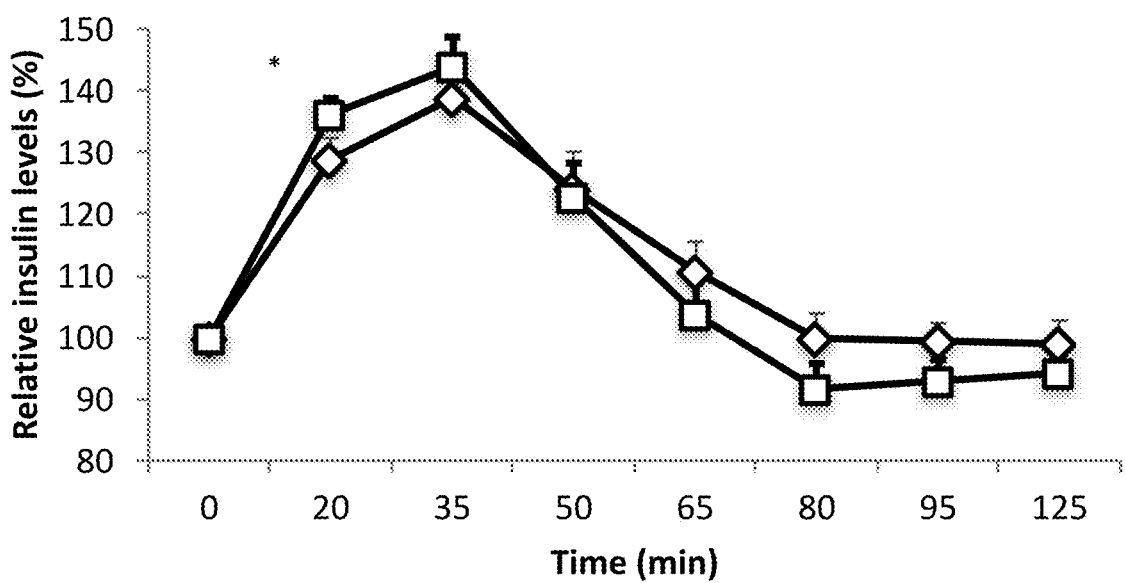

Insulin concentrations (FIG. 33A) were also significantly lower after taking product XVII vs. placebo 35.2±4.7 vs. 45.3±4.7 IU/ml respectively (20 min., p=0.002). Similarly, the rate of increase (%) in insulin concentration compared to fasting values (FIG. 33B) was significantly smaller after ingestion of the study product vs. placebo: 342.2±40.2 vs. 447.7±40.0%, (min. 20, p=0.003), providing further indications that the product exerts a preventive effect on hypoglycemia.

Example 10: The Effect of Optimized Combinations on Hypoglycemia—Clinical Studies The effects of the combination of white mulberry extract, white kidney bean extract and green coffee (product XVII in Example 7, substudy 5) on hypoglycemia were tested in an experiment conducted with volunteers with BMI ranging from 22.99 to 29.99 kg/m$^2$. Each of the study groups consisted of 30 healthy subjects. During the experimental period subjects were administered study test product XVII: white mulberry extract (600 mg)+ green coffee extract (400 mg)+ white kidney bean extract (1,200 mg) or placebo. Thereafter the participants received a meal according to the description mentioned below, for each substudy: Substudy 20—Coca Cola and Puffcorn™; and Substudy 21—pasta with cheese sauce.

SUBSTUDY 20—Coke-type beverage (400 ml, Coca-Cola®) and Puffcorn™ (50 g, Flips™)

In this substudy total hypoglycemia incidents were reduced by almost a half (<70 mg/dl), upon ingestion of product XVII compared to placebo (20 vs. 39, respectively, p=0.011). With the hypoglycemia reference point set at <65 mg/dl, 11 hypoglycemia episodes occurred compared to 26 after placebo (p=0.015), and with the reference point at <60 mg/dl there were three times less episodes of hypoglycemia compared to placebo (respectively, 5 vs. 15, p=0.037).

In minute 50 of the study no glycemia <70 mg/dl was observed upon taking product XVII vs. 5 hypoglycemia episodes after taking the placebo (<70 mg/dl, p=0.052). This trend maintained also in minute 65 when only 3 episodes of hypoglycemia were observed for XVII compared to 9 episodes in the placebo (<70 mg/dl, p=0.10). Similar tendencies were observed with regard to <65 mg/dl blood glucose incidents, for example, at minute 65 only one hypoglycemic episode was observed after ingestion of the study product compared to 8 episodes after placebo (p=0.026). With the hypoglycemia reference point set at <60 mg/dl, no hypoglycemic episodes were observed at minute 65 after ingestion of the study product versus 5 episodes after placebo (p=0.052).

SUBSTUDY 21—Pasta with Cheese Sauce (58 g, Macaroni & Cheese Dinner, KRAFT®)

In this substudy total observed hypoglycemia incidents were again greatly reduced upon ingestion of product XVII vs, placebo (2 vs. 7 incidents respectively, <70 mg/dl, p=0.145). In addition, 65 minutes after taking the study product 2 episodes of glycemia <60 mg/dl were observed versus 8 episodes after placebo (p=0.105).

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. An oral dosage form comprising mulberry extract, green coffee bean extract, and white kidney bean extract as the nutraceutically active component and a nutraceutically acceptable carrier, wherein the oral dosage form is configured to be applied for reducing blood glucose levels.

2. The oral dosage form of claim 1, wherein the nutraceutically active component is consisting of green coffee bean extract, white kidney bean extract and mulberry extract.

3. The oral dosage form of claim 1, wherein the mulberry extract is an extract of white mulberry leaves.

4. The oral dosage form of claim 1, further comprising a dietary fiber.

5. The oral dosage form of claim 1, further comprising arabinose.

6. The oral dosage form of claim 1, further comprising thylakoids.

7. A method for reducing blood glucose levels in a subject in need thereof, the method comprising administering to the subject an oral dosage form comprising mulberry extract, green coffee bean extract and white kidney bean extract as the nutraceutically active component.

8. The method of claim 7, wherein said subject is afflicted with a disease or disorder selected from the group consisting of diabetes, obesity, hypercholesterolemia, hyperglycemia, postprandial hyperglycemia and hyperlipidemia.

9. The method of claim 7, for treating prediabetes and diabetes.

10. The method of claim 7, for inducing satiety.

11. The method of claim 7, wherein the oral dosage form is administered prior to intake of a meal.

12. The method of claim 7, wherein the nutraceutically active component is consisting of green coffee bean extract, white kidney bean extract and mulberry extract.

13. The method of claim 7, wherein the oral dosage form further comprises a dietary fiber.

14. The method of claim 7, wherein the oral dosage form further comprises arabinose.

15. A method for weight management in a subject in need thereof, comprising administering to the subject an oral dosage form comprising mulberry extract, green coffee bean extract, white kidney bean extract as the nutraceutically active component and a nutraceutically acceptable carrier.

16. The method of claim 15, wherein said subject is afflicted with at least one disease or disorder selected from the group consisting of diabetes, obesity, hypercholesterolemia and hyperlipidemia and metabolic syndrome.

17. The method of claim 15, wherein the oral dosage form is administered prior to intake of a meal.

18. The method of claim 15, wherein the oral dosage form further comprises a dietary fiber.

* * * * *